(12) United States Patent
Hashizume et al.

(10) Patent No.: US 7,442,801 B2
(45) Date of Patent: Oct. 28, 2008

(54) PYRAZOLE COMPOUND

(75) Inventors: Masaya Hashizume, Toyonaka (JP); Noriyasu Sakamoto, Toyonaka (JP); Hayato Takyo, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 532 days.

(21) Appl. No.: 10/545,066

(22) PCT Filed: Feb. 3, 2004

(86) PCT No.: PCT/JP2004/001071

§ 371 (c)(1), (2), (4) Date: Aug. 9, 2005

(87) PCT Pub. No.: WO2004/085405

PCT Pub. Date: Oct. 7, 2004

(65) Prior Publication Data

US 2006/0142367 A1 Jun. 29, 2006

(30) Foreign Application Priority Data

Mar. 25, 2003 (JP) .............................. 2003-082385

(51) Int. Cl.
*C07D 231/00* (2006.01)
*A01N 25/32* (2006.01)

(52) U.S. Cl. .................... 548/374.1; 504/106

(58) Field of Classification Search ............. None
See application file for complete search history.

(56) References Cited

U.S. PATENT DOCUMENTS 4,843,068 A    6/1989   Hamaguchi et al.

FOREIGN PATENT DOCUMENTS

| CN | 1188764 A | 7/1998 |
|---|---|---|
| EP | 0 648 729 A1 | 4/1995 |
| JP | 62-53970 A | 3/1987 |
| JP | 8-208551 A | 8/1996 |
| JP | 2001-354659 A | 12/2001 |
| WO | WO-00/71536 A1 | 11/2000 |
| WO | WO-02/50042 A2 | 6/2002 |

*Primary Examiner*—Kamal Saeed
*Assistant Examiner*—Sun Jae Y Loewe
(74) *Attorney, Agent, or Firm*—Birch, Stewart, Kolasch & Birch, LLP

(57) ABSTRACT

A pyrazole compound of formula (a):

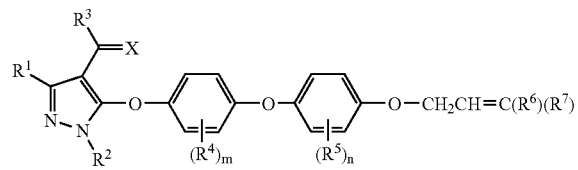

(a)

wherein $R^1$ represents C1-C4 alkyl or trifluoromethyl, $R^2$ represents C1-C4 alkyl, $R^3$ represents hydrogen or C1-C6 alkyl; $R^4$ represents halogen and so on, m represents 0 to 4 integer; $R^5$ represents halogen and so on, n represents 0 to 4 integer; $R^6$ and $R^7$ are same or different and represents hydrogen, halogen or methyl; X represents oxygen or $R^8O-N$; $R^8$ represents hydrogen, C1-C6 alkyl and the like;

has an excellent controlling activity against noxious arthropods.

14 Claims, No Drawings

PYRAZOLE COMPOUND

TECHNICAL FIELD

The present invention relates to pyrazole compounds, intermediate compounds thereof and a control method of noxious arthropods by using them.

BACKGROUND ART

A certain type of pyrazole compounds is known as an active ingredient of pesticides and acaricides. See U.S. Pat. No. 4,843,068.

However, noxious arthropods controlling activity of these pyrazole compounds is not enough in some cases, and therefore a novel compound having a noxious arthropods controlling activity is desired.

DISCLOSURE OF INVENTION

The present invention provides a pyrazole compound (hereinafter, referred as the compound of the present invention) of formula (a):

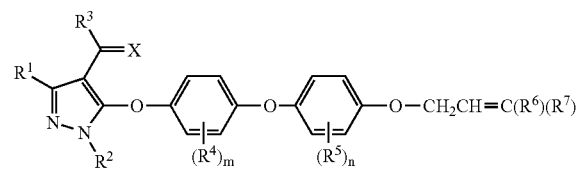

(a)

wherein $R^1$ represents C1-C4 alkyl or trifluoromethyl, $R^2$ represents C1-C4 alkyl, $R^3$ represents hydrogen or C1-C6 alkyl; $R^4$ represents halogen, C1-C3 alkyl, C1-C3 alkoxy, C1-C3 haloalkyl or C1-C3 haloalkoxy, m represents 0 to 4 integer, each of $R^4$s is same or different when m is 2 to 4 integer; $R^5$ represents halogen, C1-C3 alkyl, C1-C3 alkoxy, C1-C3 haloalkyl or C1-C3 haloalkoxy, n represents 0 to 4 integer, each of $R^5$s is same or different when n is 2 to 4 integer; $R^6$ and $R^7$ are same or different and represents hydrogen, halogen or methyl, X represents oxygen or $R^8O$—N; $R^8$ represents hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (wherein the benzyl may be substituted with halogen, C1-C4 alkyl, C1-C4 alkoxy, C2-C5 alkoxycarbonyl, trifluoromethyl or trifluoromethoxy);
a noxious arthropods controlling composition comprising the compound of the present invention; and a method for controlling noxious arthropods characterized by applying an effective amount of the compound of the present invention to noxious arthropods or habitat of noxious arthropods.

Furthermore, the present invention also provides a compound of formula (b):

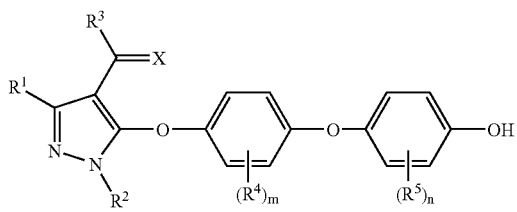

(b)

wherein $R^1$ represents C1-C4 alkyl or trifluoromethyl, $R^2$ represents C1-C4 alkyl, $R^3$ represents hydrogen or C1-C6 alkyl; $R^4$ represents halogen, C1-C3 alkyl, C1-C3 alkoxy or trifluoromethyl, m represents 0 to 4 integer, each of $R^4$s is same or different when m is 2 to 4 integer; $R^5$ represents halogen, C1-C3 alkyl, C1-C3 alkoxy or trifluoromethyl, n represents 0 to 4 integer, each of $R^5$s is same or different when n is 2 to 4 integer; X represents oxygen or by $R^8O$—N; $R^8$ represents hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (wherein the benzyl may be substituted with halogen, C1-C4 alkyl, C1-C4 alkoxy, C2-C5 alkoxycarbonyl, trifluoromethyl or trifluoro methoxy); which is useful as an intermediate of the compound of the present invention.

In the compound of the present invention, each substituent represented by $R^1$, $R^2$, $R^3$, $R^4$, $R^5$, $R^6$, $R^7$ or $R^8$ is exemplified the following substituents concretely.

The C1-C4 alkyl represented by $R^1$ is methyl, ethyl, propyl, isopropyl, butyl, isobutyl, sec-butyl and tert-butyl.

The C1-C4 alkyl represented by $R^2$ is methyl, ethyl, propyl, isopropyl, butyl, isobutyl, sec-butyl and tert-butyl.

The C1-C6 alkyl represented by $R^3$ includes methyl, ethyl, propyl, isopropyl, butyl, isobutyl, sec-butyl, tert-butyl, pentyl, 3-methylbutyl, 2,2-dimethylpropyl, 1,1-dimethylpropyl, 1-ethylpropyl, hexyl, 5-methylpentyl, 2-ethylbutyl, 3-methylpentyl and 1,3-dimethylbutyl.

The halogen represented by $R^4$ and $R^5$ is a fluorine, chlorine, bromine and iodine;
the C1-C3 alkyl includes methyl, ethyl, propyl and isopropyl;
the C1-C3 alkoxy includes methoxy, ethoxy, propoxy and isopropoxy;
the C1-C3 haloalkyl includes trifluoromethyl, 2-fluoroethyl, 2,2,2-trifluoroethyl, 3,3,3-trifluoropropyl, 2-chloroethyl and 3-bromopropyl;
the C1-C3 haloalkoxy includes trifluoroalkoxy, 2,2,2-trifluoroethoxy and 3,3,3-trifluoropropoxy.

The halogen represented by $R^6$ is a fluorine, chlorine, bromine and iodine.

The halogen represented by $R^7$ is a fluorine, chlorine, bromine and iodine.

The C1-C6 alkyl represented by $R^8$ includes methyl, ethyl, propyl, isopropyl, butyl, isobutyl, sec-butyl, tert-butyl, pentyl, neopentyl, tert-pentyl,
1-methylbutyl, 1,2-dimethylpropyl and hexyl;
the C1-C6 haloalkyl includes fluoromethyl, 2-fluoroethyl, 2,2,2-trifluoroethyl, 3,3,3-trifluoropropyl, 4,4,4-trifluorobutyl, 5,5,5-trifluoropentyl, 2-chloroethyl, 3-chloropropyl, 3-bromopropyl, 4-chlorobutyl, 4-bromobutyl, 4-chloropentyl and 4-bromopentyl;
the C3-C6 alkenyl includes allyl, 2-methyl-2-propenyl, 3-methyl-2-butenyl, 2-butenyl, 3-butenyl, 2-pentenyl, 3-pentenyl, 2-hexenyl and 3-hexenyl;
the C3-C6 haloalkenyl includes 3-chloro-2-propenyl, 3,3-dichloro-2-propenyl, 3-bromo-2-propenyl, 3,3-dibromo-2-propenyl, 2-chloro-2-propenyl, 2-bromo-2-propenyl, 2-fluoro-2-propenyl, 2,3-dichloro-2-propenyl, 2,3-dibromo-2-propenyl, 3-chloro-2-butenyl, 3-chloro-4,4,4-trifluoro-2-butenyl, 4-chloro-2-butenyl, butenyl, 4-bromo-2-butenyl and 2,3,3-trifluoro-2-propenyl;
the C3-C6 alkynyl includes 2-propynyl, 2-butynyl, 2-pentynyl, 3-butynyl and 1-methyl-2-propynyl;
the C3-C6 haloalkynyl includes 3-chloro-2-propynyl, 4-chloro-3-butynyl, 5-chloro-4-pentynyl, 6-chloro-5-hexynyl, 3-bromo-2-propynyl, 4-bromo-3-butynyl, 5-bromo-4-pentynyl and 6-bromo-5-hexynyl;
the C2-C5 cyano alkyl includes cyanomethyl, 2-cyanoethyl, 3-cyanopropyl and 4-cyanobutyl;
the benzyl optionally substituted with halogen, C1-C4 alkyl, C1-C4 alkoxy, C2-C5 alkoxycarbonyl, trifluoromethyl or trifluoromethoxy includes benzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2,3-dichlorobenzyl, 3,5-dichlorobenzyl, 2,4-dichlorobenzyl, 2-methylbenzyl, 3-methylbenzyl, 4-methylbenzyl, 2,3-dimethylbenzyl, 3,5-dimethylbenzyl, 2,4-dimethylbenzyl, 2-methoxybenzyl, 3-methoxybenzyl, 4-methoxybenzyl, 2,3-dimethoxybenzyl, 3,5-dimethoxybenzyl, 2,4-dimethoxybenzyl, 4-methoxycarbonylbenzyl, 4-ethoxycarbonylbenzyl, 4-propoxycarbonylbenzyl, 4-trifluoromethylbenzyl and 4-trifluoromethoxybenzyl.

The embodiments of the compound of the present invention are exemplified as follows:

the pyrazole compound wherein $R^1$ is methyl in the formula (a);

the pyrazole compound wherein $R^1$ is ethyl in the formula (a);

the pyrazole compound wherein $R^1$ is trifluoromethyl in the formula (a);

the pyrazole compound wherein $R^2$ is methyl in the formula (a);

the pyrazole compound wherein $R^3$ is hydrogen in the formula (a);

the pyrazole compound wherein $R^3$ is methyl in the formula (a);

the pyrazole compound wherein m is 0 in the formula (a);

the pyrazole compound wherein n is 0 in the formula (a);

the pyrazole compound wherein $R^6$ is chlorine in the formula (a);

the pyrazole compound wherein $R^6$ and $R^7$ are chlorine in the formula (a);

the pyrazole compound wherein $R^1$ is methyl, and $R^2$ is methyl in the formula (a);

the pyrazole compound wherein $R^1$ is ethyl, and $R^2$ is methyl in the formula (a);

the pyrazole compound wherein $R^1$ is trifluoromethyl, and $R^2$ is methyl in the formula (a);

the pyrazole compound wherein $R^1$ is methyl, and $R^6$ is chlorine in the formula (a);

the pyrazole compound wherein $R^1$ is ethyl, and $R^6$ is chlorine in the formula (a);

the pyrazole compound wherein $R^1$ is trifluoromethyl, and $R^6$ is chlorine in the formula (a);

the pyrazole compound wherein $R^1$ is methyl, and $R^6$ and $R^7$ are chlorine in the formula (a);

the pyrazole compound wherein $R^1$ is ethyl, and $R^6$ and $R^7$ are chlorine in the formula (a);

the pyrazole compound wherein $R^1$ is trifluoromethyl, and $R^6$ and $R^7$ are chlorine in the formula (a);

the pyrazole compound wherein $R^1$ is methyl, $R^2$ is methyl, and $R^6$ is chlorine in the formula (a);

the pyrazole compound wherein $R^1$ is ethyl, $R^2$ is methyl, and $R^6$ is chlorine in the formula (a);

the pyrazole compound wherein $R^1$ is trifluoromethyl, $R^2$ is methyl, and $R^6$ is chlorine in the formula (a);

the pyrazole compound wherein $R^1$ is methyl, $R^2$ is methyl, and $R^6$ and $R^7$ are chlorine in the formula (a);

the pyrazole compound wherein $R^1$ is ethyl, $R^2$ is methyl, and $R^6$ and $R^7$ are chlorine in the formula (a);

the pyrazole compound wherein $R^1$ is trifluoromethyl, $R^2$ is methyl, and $R^6$ and $R^7$ are chlorine in the formula (a);

the pyrazole compound wherein $R^1$ is methyl, $R^2$ is methyl, $R^3$ is hydrogen, and $R^6$ and $R^7$ are chlorine in the formula (a);

the pyrazole compound wherein $R^1$ is ethyl, $R^2$ is methyl, $R^3$ is hydrogen atom, and $R^6$ and $R^7$ are chlorine in the formula (a);

the pyrazole compound wherein $R^1$ is trifluoromethyl, $R^2$ is methyl, $R^3$ is hydrogen atom, and $R^6$ and $R^7$ are chlorine in the formula (a);

the pyrazole compound wherein $R^1$ is methyl, $R^2$ is methyl, $R^3$ is methyl, and $R^6$ and $R^7$ are chlorine in the formula (a);

the pyrazole compound wherein $R^1$ is ethyl, $R^2$ is methyl, $R^3$ is methyl, and $R^6$ and $R^7$ are chlorine in the formula (a);

the pyrazole compound wherein $R^1$ is trifluoromethyl, $R^2$ is methyl, $R^3$ is methyl, and $R^6$ and $R^7$ are chlorine in the formula (a);

the pyrazole compound wherein $R^1$ is methyl, $R^2$ is methyl, m is 0, and n is 0 in the formula (a);

the pyrazole compound wherein $R^1$ is ethyl, $R^2$ is methyl, m is 0, and n is 0 in the formula (a);

the pyrazole compound wherein $R^1$ is trifluoromethyl, $R^2$ is methyl, m is 0, and n is 0 in the formula (a);

the pyrazole compound wherein $R^1$ is methyl, $R^2$ is methyl, m is 0, n is 0, and $R^6$ is chlorine in the formula (a);

the pyrazole compound wherein $R^1$ is ethyl, $R^2$ is methyl, m is 0, n is 0, and $R^6$ is chlorine in the formula (a);

the pyrazole compound wherein $R^1$ is trifluoromethyl, $R^2$ is methyl, m is 0, n is 0, and $R^6$ is chlorine in the formula (a);

the pyrazole compound wherein $R^2$ is methyl, and $R^6$ is chlorine in the formula (a);

the pyrazole compound wherein $R^2$ is methyl, and $R^6$ and $R^7$ are chlorine in the formula (a);

the pyrazole compound wherein $R^2$ is methyl, m is 0, and n is 0 in the formula (a);

the pyrazole compound wherein $R^2$ is methyl, m is 0, n is 0, and $R^6$ is chlorine in the formula (a);

the pyrazole compound wherein $R^2$ is methyl, m is 0, n is 0, and $R^6$ and $R^7$ are chlorine in the formula (a);

the pyrazole compound wherein m is 0, and n is 0 in the formula (a);

the pyrazole compound wherein m is 0, n is 0, and $R^6$ is chlorine in the formula (a);

the pyrazole compound wherein m is 0, and n is 0, and $R^6$ and $R^7$ are chlorine in the formula (a);

the pyrazole compound wherein $R^3$ is hydrogen in the formula (a);

the pyrazole compound wherein $R^3$ is C1-C6 alkyl in the formula (a);

the pyrazole compound wherein X is $R^8O$—N; $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyanoalkyl or benzyl (wherein the benzyl may be substituted with halogen, C1-C4 alkyl, C1-C4 alkoxy, C2-C5 alkoxycarbonyl, trifluoromethyl or trifluoromethoxy) in the formula (a);

the pyrazole compound wherein X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl or C2-C5 cyanoalkyl in the formula (a);

the pyrazole compound wherein X is $R^8O$—N, and $R^8$ is benzyl (wherein the benzyl may be substituted with halogen, C1-C4 alkyl, C1-C4 alkoxy, C2-C5 alkoxycarbonyl, trifluoromethyl or trifluoromethoxy) in the formula (a);

the pyrazole compound wherein X is oxygen in the formula (a);

the pyrazole compound wherein $R^3$ is hydrogen, X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyanoalkyl or benzyl (wherein the benzyl may be substituted with halogen, C1-C4 alkyl, C1-C4 alkoxy, C2-C5 alkoxycarbonyl, trifluoromethyl or trifluoromethoxy) in the formula (a);

the pyrazole compound wherein $R^3$ is hydrogen, X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl or C2-C5 cyanoalkyl in the formula (a);

the pyrazole compound wherein $R^3$ is hydrogen, X is $R^8O$—N, and $R^8$ is benzyl (wherein the benzyl may be substituted with halogen, C1-C4 alkyl, C1-C4 alkoxy, C2-C5 alkoxycarbonyl, trifluoromethyl or trifluoromethoxy) in the formula (a);

the pyrazole compound wherein $R^3$ is hydrogen, and X is oxygen in the formula (a);

the pyrazole compound wherein $R^3$ is a hydrogen atom, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyanoalkyl or benzyl (the benzyl may be substituted with halogen, C1-C4 alkyl, C1-C4 alkoxy, C2-C5 alkoxycarbonyl, trifluoromethyl or trifluoromethoxy), $R^4$ and $R^5$ are halogen, C1-C3 alkyl, C1-C3 alkoxy or trifluoromethyl, and m and n are 0 to 2 integer in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl or C2-C5 cyanoalkyl, $R^4$ and $R^5$ are halogen, C1-C3 alkyl, C1-C3 alkoxy or trifluoromethyl, and m and n are 0 to 2 integer in the formula (a);

the pyrazole compound wherein $R^3$ is hydrogen, X is $R^8O$—N, $R^8$ is benzyl (the benzyl may be substituted with halogen, C1-C4 alkyl, C1-C4 alkoxy, C2-C5 alkoxycarbonyl, trifluoromethyl or trifluoromethoxy), $R^4$ and $R^5$ are halogen, C1-C3 alkyl, C1-C3 alkoxy or trifluoromethyl, and m and n are 0 to 2 integer in the formula (a);

the pyrazole compound wherein $R^3$ is hydrogen, X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl or C2-C5 cyanoalkyl, and $R^4$ and $R^5$ are hydrogen in the formula (a);

the pyrazole compound wherein $R^3$ is hydrogen, X is oxygen, and $R^4$ and $R^5$ are halogen, C1-C3 alkyl, C1-C3 alkoxy or trifluoromethyl, m and n are 0 to 2 integer in the formula (a);

the pyrazole compound wherein $R^3$ is hydrogen, $R^6$ is halogen, X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyanoalkyl or benzyl (the benzyl may be substituted with halogen, C1-C4 alkyl, C1-C4 alkoxy, C2-C5 alkoxycarbonyl, trifluoromethyl or trifluoromethoxy) in the formula (a);

the pyrazole compound wherein $R^3$ is hydrogen, $R^6$ is halogen, X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl or C2-C5 cyanoalkyl in the formula (a);

the pyrazole compound wherein $R^3$ is hydrogen, $R^6$ is halogen, X is $R^8O$—N, and $R^8$ is benzyl (the benzyl may be substituted with halogen, C1-C4 alkyl, C1-C4 alkoxy, C2-C5 alkoxycarbonyl, trifluoromethyl or trifluoromethoxy) in the formula (a);

the pyrazole compound wherein $R^3$ is hydrogen, $R^6$ is halogen, and X is oxygen in the formula (a);

the pyrazole compound wherein $R^3$ is hydrogen, $R^6$ and $R^7$ are halogen, X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyanoalkyl or benzyl (the benzyl may be substituted with halogen, C1-C4 alkyl, C1-C4 alkoxy, C2-C5 alkoxycarbonyl, trifluoromethyl or trifluoro methoxy) in the formula (a);

the pyrazole compound wherein $R^3$ is hydrogen, $R^6$ and $R^7$ are halogen, X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl or C2-C5 cyanoalkyl in the formula (a);

the pyrazole compound wherein $R^3$ is hydrogen, $R^6$ and $R^7$ are halogen, X is $R^8O$—N, and $R^8$ is benzyl (the benzyl may be substituted with halogen, a C1-C4 alkyl, C1-C4 alkoxy, C2-C5 alkoxycarbonyl, trifluoromethyl or trifluoro methoxy) in the formula (a);

the pyrazole compound wherein $R^3$ is hydrogen, $R^6$ and $R^7$ are halogen, and X is oxygen in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), and $R^1$ is methyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), and $R^1$ is ethyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), and $R^1$ is trifluoromethyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, a C1-C4 alkyl, C1-C4 alkoxy, C2-C5 alkoxycarbonyl, trifluoromethyl or trifluoro methoxy), and $R^2$ is methyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), and $R^3$ is hydrogen in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), and $R^3$ is methyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), and m is 0 in the formula (a);

the pyrazole compound wherein n is 0 in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), and $R^6$ is chlorine in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, a C1-C4 alkyl, C1-C4 alkoxy, C2-C5 alkoxycarbonyl, trifluoromethyl or trifluoro methoxy), and $R^6$ and $R^7$ are chlorine in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), $R^1$ is methyl, and $R^2$ is methyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), $R^1$ is ethyl, and $R^2$ is methyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano-alkyl or benzyl (the benzyl may be substituted with halogen, C1-C4 alkyl, C1-C4 alkoxy, C2-C5 alkoxycarbonyl, trifluoromethyl or trifluoro methoxy), $R^1$ is trifluoromethyl, and $R^2$ is methyl in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), $R^1$ is methyl, $R^2$ is methyl, $R^3$ is hydrogen, and $R^6$ and $R^7$ are chlorine in the formula (a);

the pyrazole compound wherein $R^1$ is ethyl, $R^2$ is methyl, $R^3$ is hydrogen, and $R^6$ and $R^7$ are chlorine in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), $R^1$ is trifluoromethyl, $R^2$ is methyl, $R^3$ is hydrogen, and $R^6$ and $R^7$ are chlorine in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), $R^1$ is methyl, $R^2$ is methyl, $R^3$ is methyl, and $R^6$ and $R^7$ are chlorine in the formula (a);

the pyrazole compound wherein $R^1$ is ethyl, $R^2$ is methyl, $R^3$ is methyl, and $R^6$ and $R^7$ are chlorine in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), $R^1$ is trifluoromethyl, $R^2$ is methyl, $R^3$ is methyl, and $R^6$ and $R^7$ are chlorine in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), m is 0, and n is 0 in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), m is 0, n is 0, and $R^6$ is chlorine in the formula (a);

the pyrazole compound wherein $R^3$ is hydrogen, X is $R^8O$—N, $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (the benzyl may be substituted with halogen, C1-C4 alkyl, C1-C4 alkoxy, C2-C5 alkoxycarbonyl, trifluoromethyl or trifluoro methoxy), m is 0, n is 0, and $R^6$ and $R^7$ are chlorine in the formula (a).

The compound of the present invention can be produced by the following method such as Production Method 1 to Production Method 4.

Production Method 1

The compound of the present invention is produced by making a compound of formula (b):

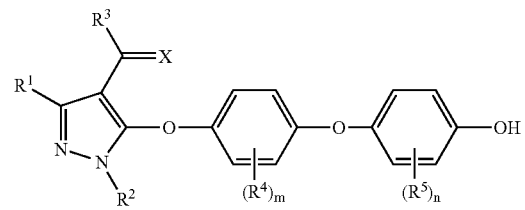

wherein $R^1$, $R^2$, $R^3$, $R^4$, $R^5$, X, m and n have the same meaning as described above;

react with a compound of formula (e):

$$L-CH_2CH=C(R^6)(R^7) \quad (e)$$

wherein $R^6$ and $R^7$ have the same meaning as described above, and L represents halogen (such as chlorine or bromine), methanesulfonyloxy, benzensulfonyloxy or toluenesulfonyloxy.

The reaction is carried out in the presence of a base usually in a solvent. The reaction temperature is usually −78 to 150° C., and the reaction period is 0.1 to 24 hours.

Examples of the solvent used for the reaction include ketones such as acetone, methyl ethyl ketone and so on; aromatic hydrocarbons such as toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as dichloromethane, chloroform, 1,2-dichloroethane, chlorobenzene, dichlorobenzene and so on; amides such as N,N-dimethylformamide, N,N-diethylacetamide and so on; nitrites such as acetonitrile and so on; dimethylsulfoxide; and the mixture thereof.

Examples of the base used for the reaction include inorganic base such as hydroxides of alkali metal or alkaline earth metal (for example sodium hydroxide, potassium hydroxide, calcium hydroxide and so on), hydrides of alkali metal or alkaline earth metal (for example sodium hydride, potassium hydride, calcium hydride and so on), sodium carbonate, potassium carbonate and so on; and organic base such as triethylamine and so on.

Based on one mole of the compound of the formula (b), 1 to 3 mole of the compound of formula (e) and 1 to 3 mole of the base are usually used.

After the reaction, the reaction mixture is poured into water, extracted with an organic solvent, the organic layer is dried and concentrated to give the compound of the present invention. Further, it is possible to purify the obtained the compound of the present invention by chromatography, recrystallization and so on.

Production Method 2

The compound of the present invention, wherein X is $R^8O$—N in the formula (a), is produced by making a compound of formula (c):

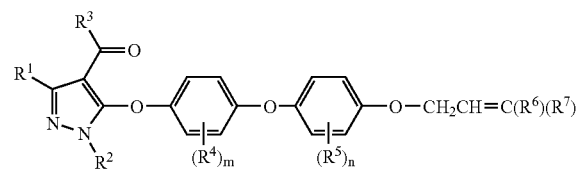

(c)

wherein $R^1$, $R^2$, $R^3$, $R^4$, $R^5$, $R^6$, $R^7$, X, m and n have the same meaning as described above;
react with a hydroxyl amine compound of formula (d):

$$R^8O-NH_2 \quad (d)$$

wherein $R^8$ has the same meaning as described above;
itself or the salt thereof, such as hydrochloric acid salt, sulfuric acid salt, nitric acid salt and so on.

The reaction is carried out in the presence of a base usually in a solvent. The reaction temperature is usually −78 to 150° C., and the reaction period is 0.1 to 24 hours.

Examples of the solvent used for the reaction include alcohol such as methanol, ethanol and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as dichloromethane, chloroform, 1,2-dichloroethane, chlorobenzene, dichlorobenzene and so on; amides such as N,N-dimethylformamide, N,N-diethylacetamide and so on; dimethylsulfoxide; water and the mixture thereof.

Examples of the base used for the reaction include inorganic base such as hydrides of alkali metal or alkaline earth metal (for example sodium hydride, potassium hydride, calcium hydride and so on), sodium carbonate, potassium carbonate and so on; and organic base such as triethylamine, pyridine and so on.

When excess of hydroxylamine compound of formula (d) itself is used, the base may not be needed.

Based on one mole of the compound of the formula (c), 1 to 3 mole of the hydroxyl amine compound of formula (d) itself or the acid thereof and 1 to 10 mole of the base are usually used.

After the reaction, the reaction mixture is poured into water, extracted with an organic solvent, the organic layer is dried and concentrated to give the compound of the present invention wherein X is $R^8O$—N in the formula (a). Further, it is possible to purify the obtained the compound of the present invention by chromatography, recrystallization and so on.

Production Method 3

The compound of the present invention, wherein X is $R^8O$—N in the formula (a), is produced by making a compound of formula (f):

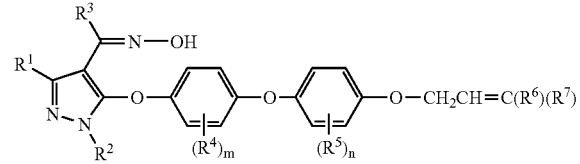

(f)

wherein $R^1$, $R^2$, $R^3$, $R^4$, $R^5$, $R^6$, $R^7$, m and n have the same meaning as described above;
react with a compound of formula (g):

$$L-R^8 \quad (g)$$

wherein $R^8$ has the same meaning as described above and L represents halogen (such as chlorine or bromine), methanesulfonyloxy, benzensulfonyloxy or toluenesulfonyloxy.

The reaction is carried out in the presence of a base usually in a solvent. The reaction temperature is usually −78 to 150° C., and the reaction period is 0.1 to 24 hours.

Examples of the solvent used for the reaction include ketones such as acetone, methyl ethyl ketone and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as chlorobenzene, dichlorobenzene and so on; amides such as N,N-dimethylformamide, N,N-diethylacetamide and so on; nitrites such as acetonitrile and so on; dimethylsulfoxide; and the mixture thereof.

Examples of the base used for the reaction include inorganic base such as hydroxides of alkali metal or alkaline earth metal (for example sodium hydroxide, potassium hydroxide, calcium hydroxide and so on), hydrides of alkali metal or alkaline earth metal (for example sodium hydride, potassium hydride, calcium hydride and so on), sodium carbonate, potassium carbonate and so on; and organic base such as triethylamine.

Based on one mole of the compound of the formula (f), 1 to 1.5 mole of the compound of formula (g) and 1 to 1.2 mole of the base are usually used.

After the reaction, the reaction mixture is poured into water, extracted with an organic solvent, the organic layer is dried and concentrated to give an objective compound wherein X is $R^8O$—N in the formula (a). Further, it is possible to purify the obtained the compound of the present invention by chromatography, recrystallization and so on.

Production Method 4

The compound of the present invention, wherein X is oxygen in the formula (a), is produced by making the compound of formula (h):

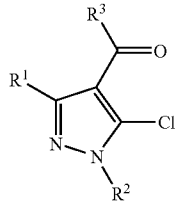

(h)

wherein $R^1$, $R^2$ and $R^3$ have the same meaning as described above;

react with a compound of formula (k):

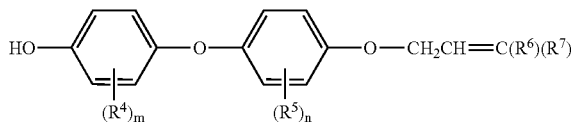

wherein $R^4$, $R^5$, $R^6$, $R^7$, m and n have the same meaning as described above.

The reaction is carried out in the presence of a base usually in a solvent. The reaction temperature is usually −78 to 150° C., and the reaction period is 0.1 to 24 hours.

Examples of the solvent used for the reaction include aromatic hydrocarbons such as toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; dimethylsulfoxide; and the mixture thereof.

Examples of the base used for the reaction include inorganic base such as hydroxides of alkali metal or alkaline earth metal (for example sodium hydroxide, potassium hydroxide, calcium hydroxide and so on), hydrides of alkali metal or alkaline earth metal (for example sodium hydride, potassium hydride, calcium hydride and so on), sodium carbonate, potassium carbonate and so on; and organic base such as triethylamine and so on.

Based on one mole of the compound of the formula (h), 0.5 to 3 mole of the compound of formula (k) and 1 to 3 mole of the base are usually used.

After the reaction, the reaction mixture is poured into water, extracted with an organic solvent, the organic layer is dried, and concentrated to give the compound of the present invention wherein X is oxygen in the formula (a). Further, it is possible to purify the obtained the compound of the present invention by chromatography, recrystallization and so on.

Next, the methods of producing the intermediates of the present invention are described following.

The compound of formula (b-2):

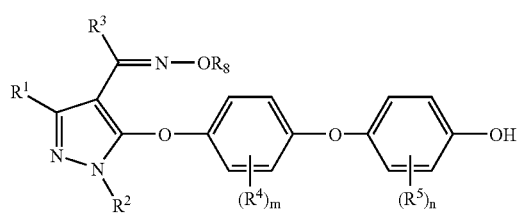

wherein $R^1$, $R^2$, $R^3$, $R^4$, $R^5$, $R^8$, m and n have the same meaning as described above;
for example, can be produced by making a compound of formula (b-1):

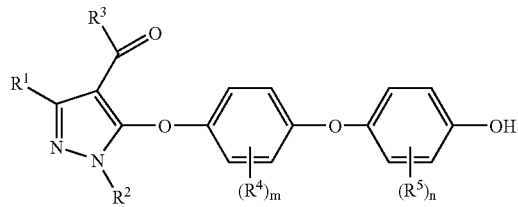

wherein $R^1$, $R^2$, $R^3$, $R^4$, $R^5$, m and n have the same meaning as described above;

react with the hydroxyl amine compound of formula (d) itself or the salt thereof, such as hydrochloric acid salt, sulfuric acid salt, nitric acid salt and so on.

The reaction is carried out in the presence of a base usually in a solvent. The reaction temperature is usually −78 to 150° C., and the reaction period is 0.1 to 24 hours.

Examples of the solvent used for the reaction include alcohol such as methanol, ethanol and so on; aromatic hydrocarbons such as benzene, toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; halogenated hydrocarbons such as dichloromethane, chloroform, 1,2-dichloroethane, chlorobenzene, dichlorobenzene and so on; amides such as N,N-dimethylformamide, N,N-diethylacetamide and so on; dimethylsulfoxide; water and the mixture thereof.

Examples of the base used for the reaction include inorganic base such as hydroxides of alkali metal or alkaline earth metal (for example sodium hydroxide, potassium hydroxide, calcium hydroxide and so on), hydrides of alkali metal or alkaline earth metal (for example sodium hydride, potassium hydride, calcium hydride and so on), sodium carbonate, potassium carbonate and so on; and organic base such as triethylamine and so on. When excess of the hydroxyl amine compound of formula (d) itself is used, the base may not be needed. Based on one mole of the compound of the formula (b-1), 1 to 3 mole of the hydroxyl amine compound of formula (d) itself or the salt thereof and 1 to 10 mole of the base are usually used.

After the reaction, the reaction mixture is poured into water, extracted with an organic solvent, the organic layer is dried and concentrated to give the compound of formula (b-2). Further, it is possible to purify the obtained the compound of formula (b-2) by chromatography, recrystallization and so on.

The compound of formula (b-1), for example, can be produced by making a the compound of formula (h) react with a compound of formula (i):

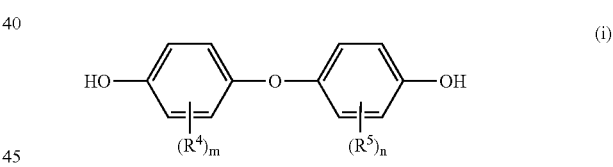

wherein $R^4$, $R^5$, m and n have the same meaning as described above.

The reaction is carried out in the presence of a base usually in a solvent. The reaction temperature is usually −78 to 150° C., and the reaction period is 0.1 to 24 hours.

Examples of the solvent used for the reaction include aromatic hydrocarbons such as toluene, xylene and so on; aliphatic hydrocarbons such as hexane, heptane and so on; ethers such as diethyl ether, tetrahydrofuran, 1,4-dioxane, 1,2-dimethoxyethane, 1,2-diethoxyethane and so on; amides such as N,N-dimethylformamide, N,N-diethylacetamide and so on; dimethylsulfoxide; and the mixture thereof.

Examples of the base used for the reaction include inorganic base such as hydroxides of alkali metal or alkaline earth metal (for example sodium hydroxide, potassium hydroxide, calcium hydroxide and so on), hydrides of alkali metal or alkaline earth metal (for example sodium hydride, potassium hydride, calcium hydride and so on), sodium carbonate, potassium carbonate and so on; and organic base such as triethylamine and so on.

Based on one mole of the compound of the formula (h), 0.5 to 3 mole of the compound of formula (i) and 1 to 3 mole of the base are usually used.

After the reaction, the reaction mixture is poured into water, extracted with an organic solvent, the organic layer is dried and concentrated to give the compound of formula (b-1). Further, it is possible to purify the obtained the compound of formula (b-1) by chromatography, recrystallization and so on.

The compound of formula (b-1) can be produced by protecting one of the two phenolic hydroxy groups in the compound of formula (i) with an appropriate protecting group (such as benzyl, tert butyldimethylsilyl and methoxymethyl), subjecting with the reaction described above, and removing the protecting group.

The compounds of the present invention are exemplified below.

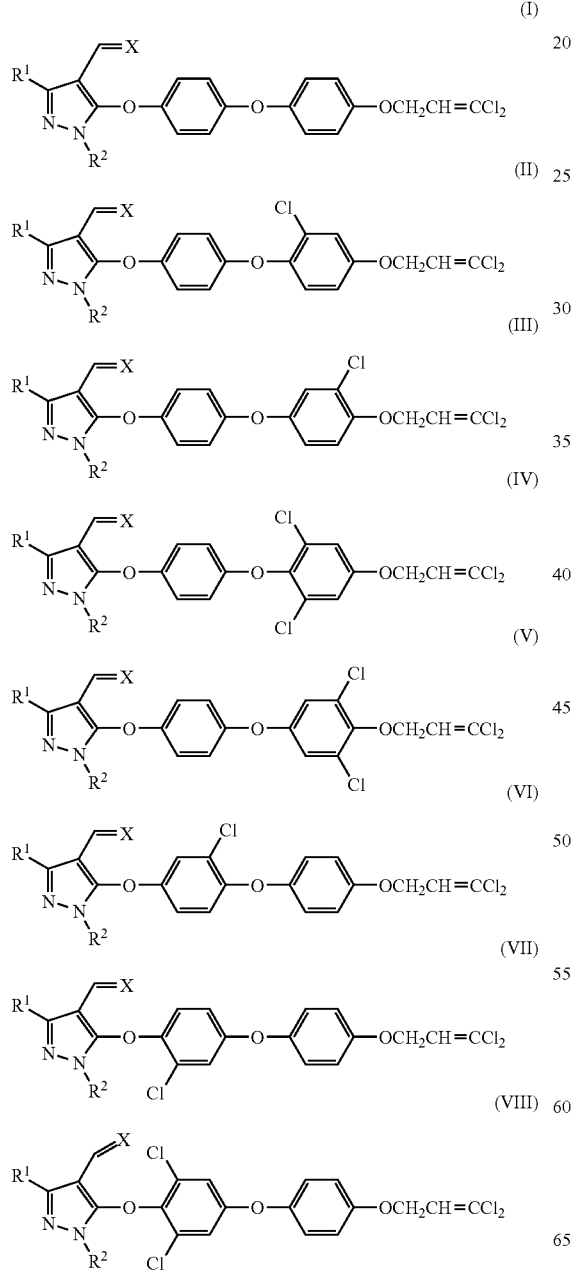

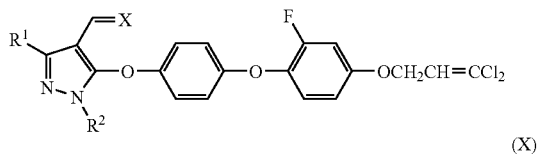

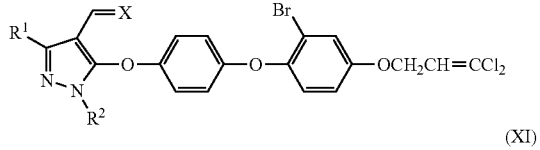

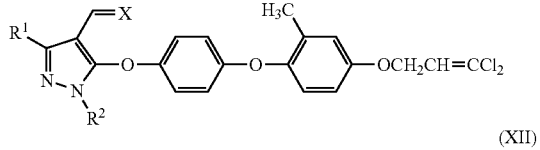

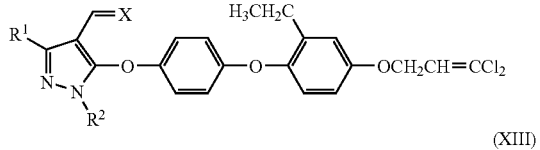

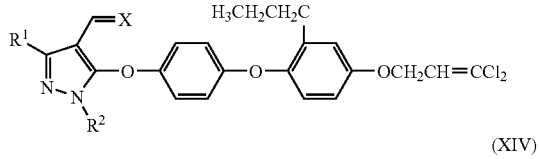

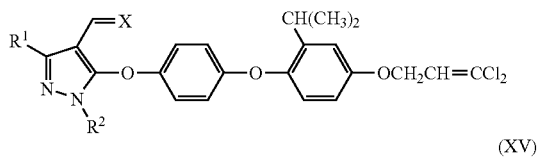

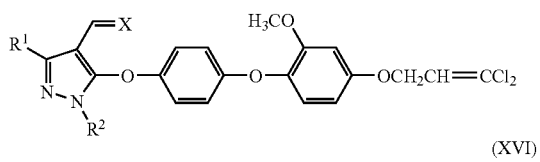

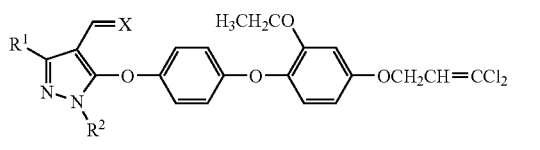

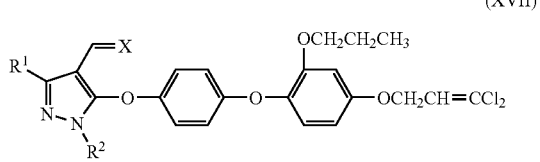

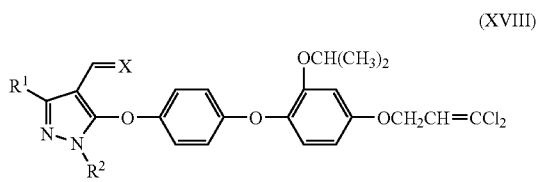

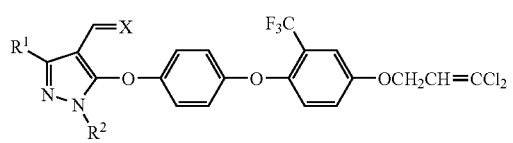
(XIX)
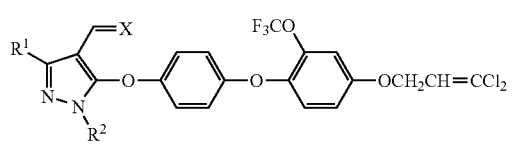
(XX)
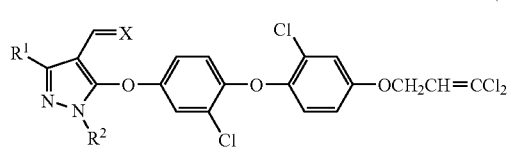
(XXI)
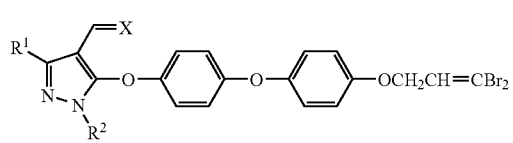
(XXII)
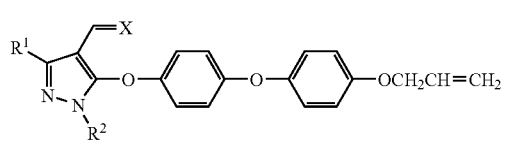
(XXIII)
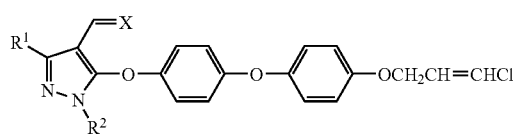
(XXIV)
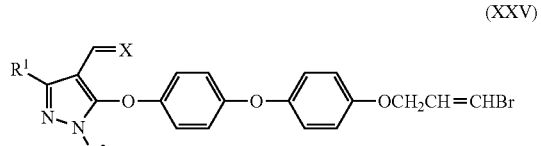
(XXV)
(XXVI)
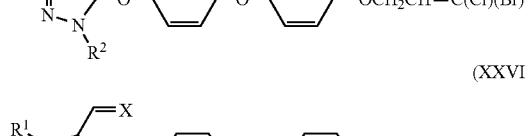
(XXVII)
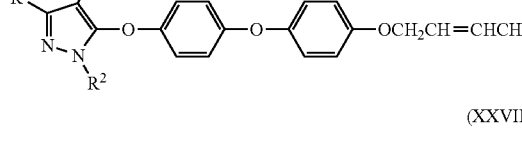
(XXVIII)
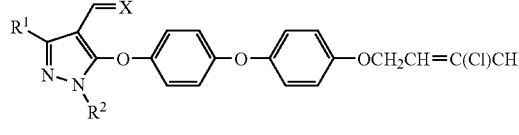
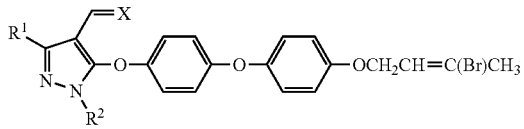
(XXIX)
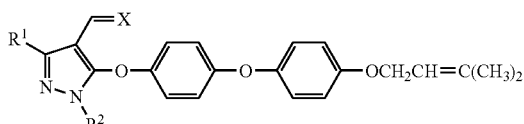
(XXX)
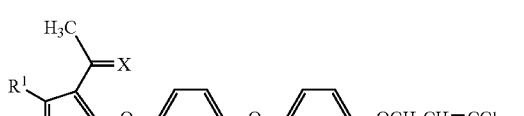
(XXXI)
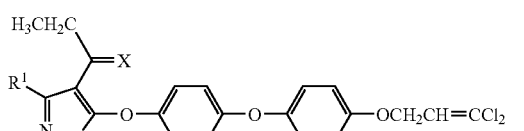
(XXXII)
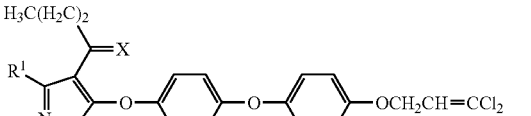
(XXXIII)
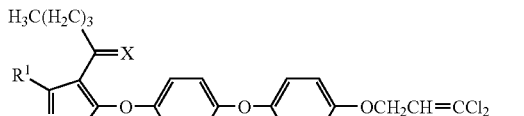
(XXXIV)
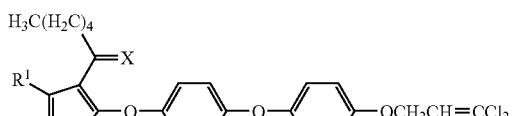
(XXXV)
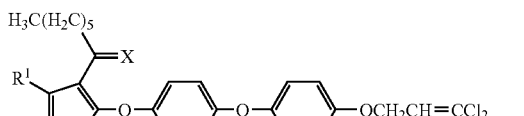
(XXXVI)
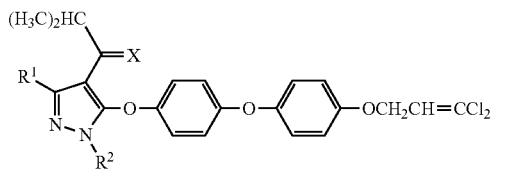
(XXXVII)

-continued
(XXXVIII)
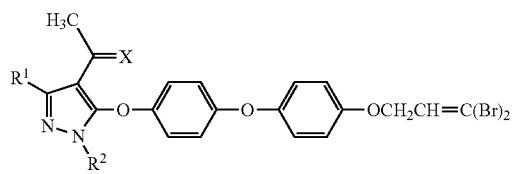
(XXXIX)
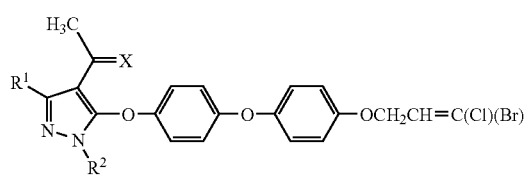
(XXXX)
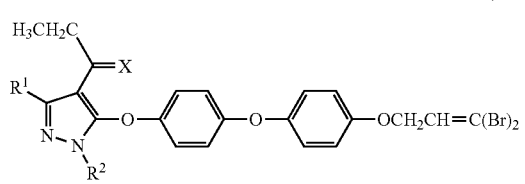
(XXXXI)
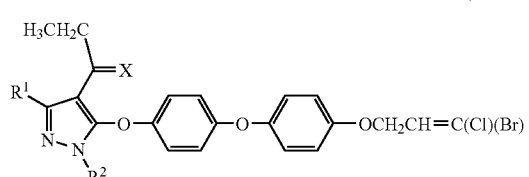
(XXXXII)
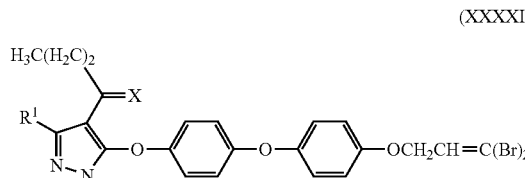
(XXXXIII)
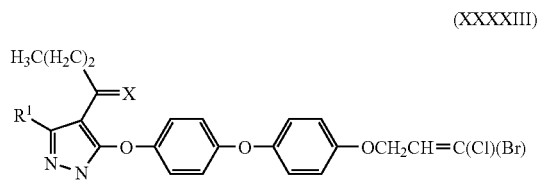
(XXXXIV)
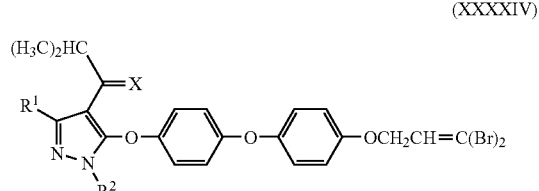
(XXXXV)
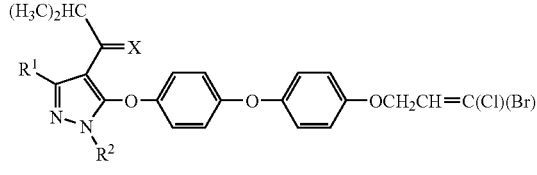
-continued
(XXXXVI)
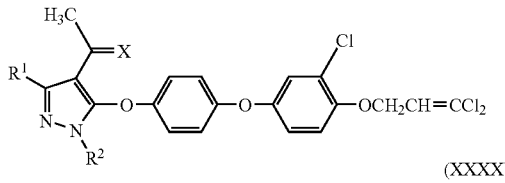
(XXXXVII)
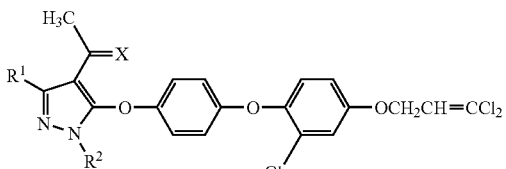
(XXXXVIII)
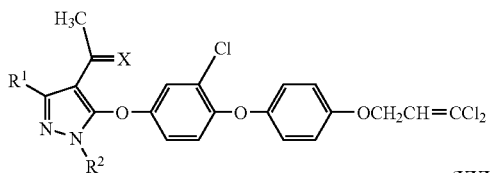
(XXXXIX)
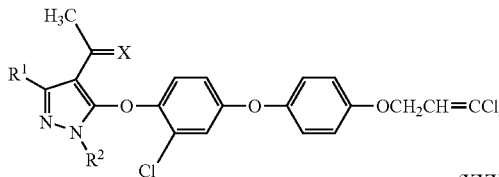
(XXXXX)
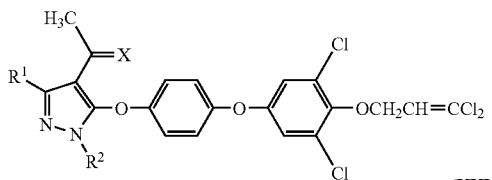
(XXXXXI)
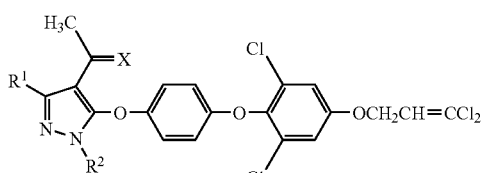
(XXXXXII)
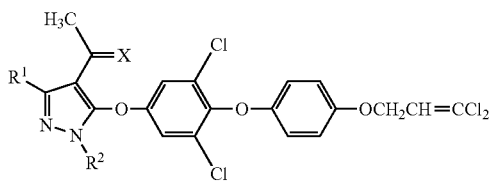
(XXXXXIII)
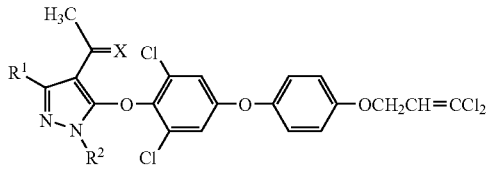
Each of $R^1$, $R^2$ and X in the formula (I) to (XXXXXIII) is any one of the combination described in Table 1 or Table 2.

TABLE 1

(X represents $R^8O-N$)

| $R^1$ | $R^2$ | $R^8$ |
|---|---|---|
| CH₃ | CH₃ | CH₃ |
| CH₃ | CH₃ | CH₃CH₂ |
| CH₃ | CH₃ | CH₃CH₂CH₂ |
| CH₃ | CH₃ | (CH₃)₂CH |
| CH₃ | CH₃ | CH₃CH₂CH₂CH₂ |
| CH₃ | CH₃ | CH₃CH₂—(CH₃)CH |
| CH₃ | CH₃ | (CH₃)₂CH—CH₂ |
| CH₃ | CH₃ | (CH₃)₃C |
| CH₃ | CH₃ | CH₃CH₂CH₂CH₂CH₂ |
| CH₃ | CH₃ | (CH₃)₂CH—CH₂CH₂ |
| CH₃ | CH₃ | (CH₃)₃C—CH₂ |
| CH₃ | CH₃ | CH₃CH₂CH₂—(CH₃)CH |
| CH₃ | CH₃ | (CH₃)₂CH—(CH₃)CH |
| CH₃ | CH₃ | CH₃CH₂CH₂CH₂CH₂CH₂ |
| CH₃ | CH₃ | CH₂F |
| CH₃ | CH₃ | CH₂F—CH₂ |
| CH₃ | CH₃ | CF₃CH₂ |
| CH₃ | CH₃ | CF₃CH₂CH₂ |
| CH₃ | CH₃ | CF₃CH₂CH₂CH₂ |
| CH₃ | CH₃ | CF₃CH₂CH₂CH₂CH₂ |
| CH₃ | CH₃ | CH₂Cl—CH₂CH₂ |
| CH₃ | CH₃ | CH₂Br—CH₂CH₂ |
| CH₃ | CH₃ | CH₂Cl—CH₂CH₂CH₂ |
| CH₃ | CH₃ | CH₂Br—CH₂CH₂CH₂ |
| CH₃ | CH₃ | CH₂Cl—CH₂CH₂CH₂CH₂ |
| CH₃ | CH₃ | CH₂Br—CH₂CH₂CH₂CH₂ |
| CH₃ | CH₃ | CH₂=CHCH₂ |
| CH₃ | CH₃ | CH₂=C(CH₃)—CH₂ |
| CH₃ | CH₃ | (CH₃)₂C=CHCH₂ |
| CH₃ | CH₃ | CH₃CH=CHCH₂ |
| CH₃ | CH₃ | CH₂=CHCH₂CH₂ |
| CH₃ | CH₃ | CH₃CH₂CH=CHCH₂ |
| CH₃ | CH₃ | CH₃CH=CHCH₂CH₂ |
| CH₃ | CH₃ | CH₃CH₂CH₂CH=CHCH₂ |
| CH₃ | CH₃ | CH₃CH₂CH=CHCH₂CH₂ |
| CH₃ | CH₃ | CHCl=CHCH₂ |
| CH₃ | CH₃ | CCl₂=CHCH₂ |
| CH₃ | CH₃ | CHBr=CHCH₂ |
| CH₃ | CH₃ | CBr₂=CHCH₂ |
| CH₃ | CH₃ | CH₂=CClCH₂ |
| CH₃ | CH₃ | CH₂=CBrCH₂ |
| CH₃ | CH₃ | CH₂=CFCH₂ |
| CH₃ | CH₃ | CHCl=CClCH₂ |
| CH₃ | CH₃ | CHBr=CBrCH₂ |
| CH₃ | CH₃ | CH₃CCl=CHCH₂ |
| CH₃ | CH₃ | CF₃CCl=CHCH₂ |
| CH₃ | CH₃ | CClH₂—CH=CHCH₂ |
| CH₃ | CH₃ | CBrH₂—CH=CHCH₂ |
| CH₃ | CH₃ | CF₂=CFCH₂ |
| CH₃ | CH₃ | CH≡CCH₂ |
| CH₃ | CH₃ | CH₃C≡CCH₂ |
| CH₃ | CH₃ | CH₃CH₂C≡CCH₂ |
| CH₃ | CH₃ | CH₃C≡CCH₂CH₂ |
| CH₃ | CH₃ | CH≡C—(CH₃)CH |
| CH₃ | CH₃ | N≡CCH₂ |
| CH₃ | CH₃ | N≡CCH₂CH₂ |
| CH₃ | CH₃ | N≡CCH₂CH₂CH₂ |
| CH₃ | CH₃ | N≡CCH₂CH₂CH₂CH₂ |
| CH₃ | CH₃ | H |
| CH₃ | CH₃ | C₆H₅—CH₂ |
| CH₃ | CH₃ | 2-F—C₆H₄—CH₂ |
| CH₃ | CH₃ | 3-F—C₆H₄—CH₂ |
| CH₃ | CH₃ | 4-F—C₆H₄—CH₂ |
| CH₃ | CH₃ | 2-Cl—C₆H₄—CH₂ |
| CH₃ | CH₃ | 3-Cl—C₆H₄—CH₂ |
| CH₃ | CH₃ | 4-Cl—C₆H₄—CH₂ |
| CH₃ | CH₃ | 2-Br—C₆H₄—CH₂ |
| CH₃ | CH₃ | 3-Br—C₆H₄—CH₂ |
| CH₃ | CH₃ | 4-Br—C₆H₄—CH₂ |
| CH₃ | CH₃ | 4-I—C₆H₄—CH₂ |
| CH₃ | CH₃ | 2-CH₃—C₆H₄—CH₂ |
| CH₃ | CH₃ | 3-CH₃—C₆H₄—CH₂ |
| CH₃ | CH₃ | 4-CH₃—C₆H₄—CH₂ |
| CH₃ | CH₃ | 4-CF₃—C₆H₄—CH₂ |
| CH₃ | CH₃ | 4-CH₃CH₂—C₆H₄—CH₂ |
| CH₃ | CH₃ | 4-(CH₃)₂CH—C₆H₄—CH₂ |
| CH₃ | CH₃ | 4-CH₃CH₂CH₂—C₆H₄—CH₂ |
| CH₃ | CH₃ | 4-(CH₃)₃C—C₆H₄—CH₂ |
| CH₃ | CH₃ | 2,4-(CH₃)₂—C₆H₃—CH₂ |
| CH₃ | CH₃ | 2,4,6-(CH₃)₃—C₆H₂—CH₂ |
| CH₃ | CH₃ | 2,4-Cl₂—C₆H₃—CH₂ |
| CH₃ | CH₃ | 3,4-Cl₂—C₆H₃—CH₂ |
| CH₃ | CH₃ | 2,5-Cl₂—C₆H₃—CH₂ |
| CH₃ | CH₃ | 3,5-Cl₂—C₆H₃—CH₂ |
| CH₃ | CH₃ | 2,6-Cl₂—C₆H₃—CH₂ |
| CH₃ | CH₃ | 4-CH₃O—C₆H₄—CH₂ |
| CH₃ | CH₃ | 4-CF₃O—C₆H₄—CH₂ |
| CH₃ | CH₃ | 4-CH₃CH₂O—C₆H₄—CH₂ |
| CH₃ | CH₃ | 4-(CH₃)₂CHO—C₆H₄—CH₂ |
| CH₃ | CH₃ | 4-(CH₃)₃CO—C₆H₄—CH₂ |
| CH₃ | CH₃ | 4-CH₃OC(=O)—C₆H₄—CH₂ |
| CH₃ | CH₃ | 4-CH₃CH₂OC(=O)—C₆H₄—CH₂ |
| CH₃ | CH₃ | 4-CH₃CH₂CH₂OC(=O)—C₆H₄—CH₂ |
| CH₃ | CH₃ | 4-(CH₃)₂CHOC(=O)—C₆H₄—CH₂ |
| CH₃ | CH₃ | 4-(CH₃)₃COC(=O)—C₆H₄—CH₂ |
| CH₃ | CH₃ | CH₂Cl—CH₂ |
| CH₃ | CH₃ | CCl=CCH₂ |
| CH₃ | CH₃ | CBr=CCH₂ |
| CH₃ | CH₃CH₂ | CH₃ |
| CH₃ | CH₃CH₂ | CH₃CH₂ |
| CH₃ | CH₃CH₂ | CH₃CH₂CH₂ |
| CH₃ | CH₃CH₂ | (CH₃)₂CH |
| CH₃ | CH₃CH₂ | CH₃CH₂CH₂CH₂ |
| CH₃ | CH₃CH₂ | CH₃CH₂—(CH₃)CH |
| CH₃ | CH₃CH₂ | (CH₃)₂CHCH₂ |
| CH₃ | CH₃CH₂ | (CH₃)₃C |
| CH₃ | CH₃CH₂ | CH₃CH₂CH₂CH₂CH₂ |
| CH₃ | CH₃CH₂ | (CH₃)₂CHCH₂CH₂ |
| CH₃ | CH₃CH₂ | (CH₃)₃CCH₂ |
| CH₃ | CH₃CH₂ | CH₃CH₂CH₂—(CH₃)CH |
| CH₃ | CH₃CH₂ | (CH₃)₂CH—(CH₃)CH |
| CH₃ | CH₃CH₂ | CH₃CH₂CH₂CH₂CH₂CH₂ |
| CH₃ | CH₃CH₂ | CH₂F |
| CH₃ | CH₃CH₂ | CH₂F—CH₂ |
| CH₃ | CH₃CH₂ | CF₃CH₂ |
| CH₃ | CH₃CH₂ | CF₃CH₂CH₂ |
| CH₃ | CH₃CH₂ | CF₃CH₂CH₂CH₂ |
| CH₃ | CH₃CH₂ | CF₃CH₂CH₂CH₂CH₂ |
| CH₃ | CH₃CH₂ | CH₂Cl—CH₂CH₂ |
| CH₃ | CH₃CH₂ | CH₂Br—CH₂CH₂ |
| CH₃ | CH₃CH₂ | CH₂Cl—CH₂CH₂CH₂ |
| CH₃ | CH₃CH₂ | CH₂Br—CH₂CH₂CH₂ |
| CH₃ | CH₃CH₂ | CH₂Cl—CH₂CH₂CH₂CH₂ |
| CH₃ | CH₃CH₂ | CH₂Br—CH₂CH₂CH₂CH₂ |
| CH₃ | CH₃CH₂ | CH₂=CHCH₂ |
| CH₃ | CH₃CH₂ | CH₂=C(CH₃)—CH₂ |
| CH₃ | CH₃CH₂ | (CH₃)₂C=CHCH₂ |
| CH₃ | CH₃CH₂ | CH₃CH=CHCH₂ |
| CH₃ | CH₃CH₂ | CH₂=CHCH₂CH₂ |
| CH₃ | CH₃CH₂ | CH₃CH₂CH=CHCH₂ |
| CH₃ | CH₃CH₂ | CH₃CH=CHCH₂CH₂ |
| CH₃ | CH₃CH₂ | CH₃CH₂CH₂CH=CHCH₂ |
| CH₃ | CH₃CH₂ | CH₃CH₂CH=CHCH₂CH₂ |
| CH₃ | CH₃CH₂ | CHCl=CHCH₂ |
| CH₃ | CH₃CH₂ | CCl₂=CHCH₂ |
| CH₃ | CH₃CH₂ | CHBr=CHCH₂ |
| CH₃ | CH₃CH₂ | CBr₂=CHCH₂ |
| CH₃ | CH₃CH₂ | CH₂=CClCH₂ |
| CH₃ | CH₃CH₂ | CH₂=CBrCH₂ |
| CH₃ | CH₃CH₂ | CH₂=CFCH₂ |
| CH₃ | CH₃CH₂ | CHCl=CClCH₂ |
| CH₃ | CH₃CH₂ | CHBr=CBrCH₂ |
| CH₃ | CH₃CH₂ | CH₃CCl=CHCH₂ |
| CH₃ | CH₃CH₂ | CF₃CCl=CHCH₂ |
| CH₃ | CH₃CH₂ | CClH₂—CH=CHCH₂ |
| CH₃ | CH₃CH₂ | CBrH₂—CH=CHCH₂ |
| CH₃ | CH₃CH₂ | CF₂=CFCH₂ |
| CH₃ | CH₃CH₂ | CH≡CCH₂ |
| CH₃ | CH₃CH₂ | CH₃C≡CCH₂ |
| CH₃ | CH₃CH₂ | CH₃CH₂C≡CCH₂ |

TABLE 1-continued (X represents R⁸O—N)

| R¹ | R² | R⁸ |
|---|---|---|
| CH₃ | CH₃CH₂ | CH₃C≡CCH₂CH₂ |
| CH₃ | CH₃CH₂ | CH≡C—(CH₃)CH |
| CH₃ | CH₃CH₂ | N≡CCH₂ |
| CH₃ | CH₃CH₂ | N≡CCH₂CH₂ |
| CH₃ | CH₃CH₂ | N≡CCH₂CH₂CH₂ |
| CH₃ | CH₃CH₂ | N≡CCH₂CH₂CH₂CH₂ |
| CH₃ | CH₃CH₂ | H |
| CH₃ | CH₃CH₂ | C₆H₅—CH₂ |
| CH₃ | CH₃CH₂ | 2-F—C₆H₄—CH₂ |
| CH₃ | CH₃CH₂ | 3-F—C₆H₄—CH₂ |
| CH₃ | CH₃CH₂ | 4-F—C₆H₄—CH₂ |
| CH₃ | CH₃CH₂ | 2-Cl—C₆H₄—CH₂ |
| CH₃ | CH₃CH₂ | 3-Cl—C₆H₄—CH₂ |
| CH₃ | CH₃CH₂ | 4-Cl—C₆H₄—CH₂ |
| CH₃ | CH₃CH₂ | 2-Br—C₆H₄—CH₂ |
| CH₃ | CH₃CH₂ | 3-Br—C₆H₄—CH₂ |
| CH₃ | CH₃CH₂ | 4-Br—C₆H₄—CH₂ |
| CH₃ | CH₃CH₂ | 4-I—C₆H₄—CH₂ |
| CH₃ | CH₃CH₂ | 2-CH₃—C₆H₄—CH₂ |
| CH₃ | CH₃CH₂ | 3-CH₃—C₆H₄—CH₂ |
| CH₃ | CH₃CH₂ | 4-CH₃—C₆H₄—CH₂ |
| CH₃ | CH₃CH₂ | 4-CF₃—C₆H₄—CH₂ |
| CH₃ | CH₃CH₂ | 4-CH₃CH₂—C₆H₄—CH₂ |
| CH₃ | CH₃CH₂ | 4-(CH₃)₂CH—C₆H₄—CH₂ |
| CH₃ | CH₃CH₂ | 4-CH₃CH₂CH₂—C₆H₄—CH₂ |
| CH₃ | CH₃CH₂ | 4-(CH₃)₃C—C₆H₄—CH₂ |
| CH₃ | CH₃CH₂ | 2,4-(CH₃)₂—C₆H₃—CH₂ |
| CH₃ | CH₃CH₂ | 2,4,6-(CH₃)₃—C₆H₂—CH₂ |
| CH₃ | CH₃CH₂ | 2,4-Cl₂—C₆H₃—CH₂ |
| CH₃ | CH₃CH₂ | 3,4-Cl₂—C₆H₃—CH₂ |
| CH₃ | CH₃CH₂ | 2,5-Cl₂—C₆H₃—CH₂ |
| CH₃ | CH₃CH₂ | 3,5-Cl₂—C₆H₃—CH₂ |
| CH₃ | CH₃CH₂ | 2,6-Cl₂—C₆H₃—CH₂ |
| CH₃ | CH₃CH₂ | 4-CH₃O—C₆H₄—CH₂ |
| CH₃ | CH₃CH₂ | 4-CF₃O—C₆H₄—CH₂ |
| CH₃ | CH₃CH₂ | 4-CH₃CH₂O—C₆H₄—CH₂ |
| CH₃ | CH₃CH₂ | 4-(CH₃)₂CHO—C₆H₄—CH₂ |
| CH₃ | CH₃CH₂ | 4-(CH₃)₃CO—C₆H₄—CH₂ |
| CH₃ | CH₃CH₂ | 4-CH₃OC(=O)—C₆H₄—CH₂ |
| CH₃ | CH₃CH₂ | 4-CH₃CH₂OC(=O)—C₆H₄—CH₂ |
| CH₃ | CH₃CH₂ | 4-CH₃CH₂CH₂OC(=O)—C₆H₄—CH₂ |
| CH₃ | CH₃CH₂ | 4-(CH₃)₂CHOC(=O)—C₆H₄—CH₂ |
| CH₃ | CH₃CH₂ | 4-(CH₃)₃COC(=O)—C₆H₄—CH₂ |
| CH₃ | CH₃CH₂ | CH₂Cl—CH₂ |
| CH₃ | CH₃CH₂ | CCl≡CCH₂ |
| CH₃ | CH₃CH₂ | CBr≡CCH₂ |
| CH₃ | (CH₃)₂CH | CH₃ |
| CH₃ | (CH₃)₂CH | CH₃CH₂ |
| CH₃ | (CH₃)₂CH | CH₃CH₂CH₂ |
| CH₃ | (CH₃)₂CH | (CH₃)₂CH |
| CH₃ | (CH₃)₂CH | CH₃CH₂CH₂CH₂ |
| CH₃ | (CH₃)₂CH | CH₃CH₂—(CH₃)CH |
| CH₃ | (CH₃)₂CH | (CH₃)₂CHCH₂ |
| CH₃ | (CH₃)₂CH | (CH₃)₃C |
| CH₃ | (CH₃)₂CH | CH₃CH₂CH₂CH₂CH₂ |
| CH₃ | (CH₃)₂CH | (CH₃)₂CHCH₂CH₂ |
| CH₃ | (CH₃)₂CH | (CH₃)₃CCH₂ |
| CH₃ | (CH₃)₂CH | CH₃CH₂CH₂—(CH₃)CH |
| CH₃ | (CH₃)₂CH | (CH₃)₂CH—(CH₃)CH |
| CH₃ | (CH₃)₂CH | CH₃CH₂CH₂CH₂CH₂CH₂ |
| CH₃ | (CH₃)₂CH | CH₂F |
| CH₃ | (CH₃)₂CH | CH₂F—CH₂ |
| CH₃ | (CH₃)₂CH | CF₃CH₂ |
| CH₃ | (CH₃)₂CH | CF₃CH₂CH₂ |
| CH₃ | (CH₃)₂CH | CF₃CH₂CH₂CH₂ |
| CH₃ | (CH₃)₂CH | CF₃CH₂CH₂CH₂CH₂ |
| CH₃ | (CH₃)₂CH | CH₂Cl—CH₂CH₂ |
| CH₃ | (CH₃)₂CH | CH₂Br—CH₂CH₂ |
| CH₃ | (CH₃)₂CH | CH₂Cl—CH₂CH₂CH₂ |
| CH₃ | (CH₃)₂CH | CH₂Br—CH₂CH₂CH₂ |
| CH₃ | (CH₃)₂CH | CH₂Cl—CH₂CH₂CH₂CH₂ |
| CH₃ | (CH₃)₂CH | CH₂Br—CH₂CH₂CH₂CH₂ |
| CH₃ | (CH₃)₂CH | CH₂=CHCH₂ |
| CH₃ | (CH₃)₂CH | CH₂=C(CH₃)—CH₂ |
| CH₃ | (CH₃)₂CH | (CH₃)₂C=CHCH₂ |

TABLE 1-continued (X represents R⁸O—N)

| R¹ | R² | R⁸ |
|---|---|---|
| CH₃ | (CH₃)₂CH | CH₃CH=CHCH₂ |
| CH₃ | (CH₃)₂CH | CH₂=CHCH₂CH₂ |
| CH₃ | (CH₃)₂CH | CH₃CH₂CH=CHCH₂ |
| CH₃ | (CH₃)₂CH | CH₃CH=CHCH₂CH₂ |
| CH₃ | (CH₃)₂CH | CH₃CH₂CH₂CH=CHCH₂ |
| CH₃ | (CH₃)₂CH | CH₃CH₂CH=CHCH₂CH₂ |
| CH₃ | (CH₃)₂CH | CHCl=CHCH₂ |
| CH₃ | (CH₃)₂CH | CCl₂=CHCH₂ |
| CH₃ | (CH₃)₂CH | CHBr=CHCH₂ |
| CH₃ | (CH₃)₂CH | CBr₂=CHCH₂ |
| CH₃ | (CH₃)₂CH | CH₂=CClCH₂ |
| CH₃ | (CH₃)₂CH | CH₂=CBrCH₂ |
| CH₃ | (CH₃)₂CH | CH₂=CFCH₂ |
| CH₃ | (CH₃)₂CH | CHCl=CClCH₂ |
| CH₃ | (CH₃)₂CH | CHBr=CBrCH₂ |
| CH₃ | (CH₃)₂CH | CH₃CCl=CHCH₂ |
| CH₃ | (CH₃)₂CH | CF₃CCl=CHCH₂ |
| CH₃ | (CH₃)₂CH | CClH₂CH=CHCH₂ |
| CH₃ | (CH₃)₂CH | CBrH₂CH=CHCH₂ |
| CH₃ | (CH₃)₂CH | CF₂=CFCH₂ |
| CH₃ | (CH₃)₂CH | CH≡CCH₂ |
| CH₃ | (CH₃)₂CH | CH₃C≡CCH₂ |
| CH₃ | (CH₃)₂CH | CH₃CH₂C≡CCH₂ |
| CH₃ | (CH₃)₂CH | CH₃C≡CCH₂CH₂ |
| CH₃ | (CH₃)₂CH | CH≡C—(CH₃)CH |
| CH₃ | (CH₃)₂CH | N≡CCH₂ |
| CH₃ | (CH₃)₂CH | N≡CCH₂CH₂ |
| CH₃ | (CH₃)₂CH | N≡CCH₂CH₂CH₂ |
| CH₃ | (CH₃)₂CH | N≡CCH₂CH₂CH₂CH₂ |
| CH₃ | (CH₃)₂CH | H |
| CH₃ | (CH₃)₂CH | C₆H₅—CH₂ |
| CH₃ | (CH₃)₂CH | 2-F—C₆H₄—CH₂ |
| CH₃ | (CH₃)₂CH | 3-F—C₆H₄—CH₂ |
| CH₃ | (CH₃)₂CH | 4-F—C₆H₄—CH₂ |
| CH₃ | (CH₃)₂CH | 2-Cl—C₆H₄—CH₂ |
| CH₃ | (CH₃)₂CH | 3-Cl—C₆H₄—CH₂ |
| CH₃ | (CH₃)₂CH | 4-Cl—C₆H₄—CH₂ |
| CH₃ | (CH₃)₂CH | 2-Br—C₆H₄—CH₂ |
| CH₃ | (CH₃)₂CH | 3-Br—C₆H₄—CH₂ |
| CH₃ | (CH₃)₂CH | 4-Br—C₆H₄—CH₂ |
| CH₃ | (CH₃)₂CH | 4-I—C₆H₄—CH₂ |
| CH₃ | (CH₃)₂CH | 2-CH₃—C₆H₄—CH₂ |
| CH₃ | (CH₃)₂CH | 3-CH₃—C₆H₄—CH₂ |
| CH₃ | (CH₃)₂CH | 4-CH₃—C₆H₄—CH₂ |
| CH₃ | (CH₃)₂CH | 4-CF₃—C₆H₄—CH₂ |
| CH₃ | (CH₃)₂CH | 4-CH₃CH₂—C₆H₄—CH₂ |
| CH₃ | (CH₃)₂CH | 4-(CH₃)₂CH—C₆H₄—CH₂ |
| CH₃ | (CH₃)₂CH | 4-CH₃CH₂CH₂—C₆H₄—CH₂ |
| CH₃ | (CH₃)₂CH | 4-(CH₃)₃C—C₆H₄—CH₂ |
| CH₃ | (CH₃)₂CH | 2,4-(CH₃)₂—C₆H₃—CH₂ |
| CH₃ | (CH₃)₂CH | 2,4,6-(CH₃)₃—C₆H₂—CH₂ |
| CH₃ | (CH₃)₂CH | 2,4-Cl₂—C₆H₃—CH₂ |
| CH₃ | (CH₃)₂CH | 3,4-Cl₂—C₆H₃—CH₂ |
| CH₃ | (CH₃)₂CH | 2,5-Cl₂—C₆H₃—CH₂ |
| CH₃ | (CH₃)₂CH | 3,5-Cl₂—C₆H₃—CH₂ |
| CH₃ | (CH₃)₂CH | 2,6-Cl₂—C₆H₃—CH₂ |
| CH₃ | (CH₃)₂CH | 4-CH₃O—C₆H₄—CH₂ |
| CH₃ | (CH₃)₂CH | 4-CF₃O—C₆H₄—CH₂ |
| CH₃ | (CH₃)₂CH | 4-CH₃CH₂O—C₆H₄—CH₂ |
| CH₃ | (CH₃)₂CH | 4-(CH₃)₂CHO—C₆H₄—CH₂ |
| CH₃ | (CH₃)₂CH | 4-(CH₃)₃CO—C₆H₄—CH₂ |
| CH₃ | (CH₃)₂CH | 4-CH₃OC(=O)—C₆H₄—CH₂ |
| CH₃ | (CH₃)₂CH | 4-CH₃CH₂OC(=O)—C₆H₄—CH₂ |
| CH₃ | (CH₃)₂CH | 4-CH₃CH₂CH₂OC(=O)—C₆H₄—CH₂ |
| CH₃ | (CH₃)₂CH | 4-(CH₃)₂CHOC(=O)—C₆H₄—CH₂ |
| CH₃ | (CH₃)₂CH | 4-(CH₃)₃COC(=O)—C₆H₄—CH₂ |
| CH₃ | (CH₃)₂CH | CH₂Cl—CH₂ |
| CH₃ | (CH₃)₂CH | CCl≡CCH₂ |
| CH₃ | (CH₃)₂CH | CBr≡CCH₂ |
| CH₃ | (CH₃)₃C | CH₃ |
| CH₃ | (CH₃)₃C | CH₃CH₂ |
| CH₃ | (CH₃)₃C | CH₃CH₂CH₂ |
| CH₃ | (CH₃)₃C | (CH₃)₂CH |
| CH₃ | (CH₃)₃C | CH₃CH₂CH₂CH₂ |
| CH₃ | (CH₃)₃C | CH₃CH₂—(CH₃)CH |

TABLE 1-continued (X represents R⁸O—N)

| R¹ | R² | R⁸ |
|---|---|---|
| CH₃ | (CH₃)₃C | (CH₃)₂CHCH₂ |
| CH₃ | (CH₃)₃C | (CH₃)₃C |
| CH₃ | (CH₃)₃C | CH₃CH₂CH₂CH₂CH₂ |
| CH₃ | (CH₃)₃C | (CH₃)₂CHCH₂CH₂ |
| CH₃ | (CH₃)₃C | (CH₃)₃CCH₂ |
| CH₃ | (CH₃)₃C | CH₃CH₂CH₂—(CH₃)CH |
| CH₃ | (CH₃)₃C | (CH₃)₂CH—(CH₃)CH |
| CH₃ | (CH₃)₃C | CH₃CH₂CH₂CH₂CH₂CH₂ |
| CH₃ | (CH₃)₃C | CH₂F |
| CH₃ | (CH₃)₃C | CH₂F—CH₂ |
| CH₃ | (CH₃)₃C | CF₃CH₂ |
| CH₃ | (CH₃)₃C | CF₃CH₂CH₂ |
| CH₃ | (CH₃)₃C | CF₃CH₂CH₂CH₂ |
| CH₃ | (CH₃)₃C | CF₃CH₂CH₂CH₂CH₂ |
| CH₃ | (CH₃)₃C | CH₂ClCH₂CH₂ |
| CH₃ | (CH₃)₃C | CH₂Br—CH₂CH₂ |
| CH₃ | (CH₃)₃C | CH₂Cl—CH₂CH₂CH₂ |
| CH₃ | (CH₃)₃C | CH₂Br—CH₂CH₂CH₂ |
| CH₃ | (CH₃)₃C | CH₂Cl—CH₂CH₂CH₂CH₂ |
| CH₃ | (CH₃)₃C | CH₂Br—CH₂CH₂CH₂CH₂ |
| CH₃ | (CH₃)₃C | CH₂=CHCH₂ |
| CH₃ | (CH₃)₃C | CH₂=C(CH₃)—CH₂ |
| CH₃ | (CH₃)₃C | (CH₃)₂C=CHCH₂ |
| CH₃ | (CH₃)₃C | CH₃CH=CHCH₂ |
| CH₃ | (CH₃)₃C | CH₂=CHCH₂CH₂ |
| CH₃ | (CH₃)₃C | CH₃CH₂CH=CHCH₂ |
| CH₃ | (CH₃)₃C | CH₃CH=CHCH₂CH₂ |
| CH₃ | (CH₃)₃C | CH₃CH₂CH₂CH=CHCH₂ |
| CH₃ | (CH₃)₃C | CH₃CH₂CH=CHCH₂CH₂ |
| CH₃ | (CH₃)₃C | CHCl=CHCH₂ |
| CH₃ | (CH₃)₃C | CCl₂=CHCH₂ |
| CH₃ | (CH₃)₃C | CHBr=CHCH₂ |
| CH₃ | (CH₃)₃C | CBr₂=CHCH₂ |
| CH₃ | (CH₃)₃C | CH₂=CClCH₂ |
| CH₃ | (CH₃)₃C | CH₂=CBrCH₂ |
| CH₃ | (CH₃)₃C | CH₂=CFCH₂ |
| CH₃ | (CH₃)₃C | CHCl=CClCH₂ |
| CH₃ | (CH₃)₃C | CHBr=CBrCH₂ |
| CH₃ | (CH₃)₃C | CH₃CCl=CHCH₂ |
| CH₃ | (CH₃)₃C | CF₃CCl=CHCH₂ |
| CH₃ | (CH₃)₃C | CClH₂CH=CHCH₂ |
| CH₃ | (CH₃)₃C | CBrH₂CH=CHCH₂ |
| CH₃ | (CH₃)₃C | CF₂=CFCH₂ |
| CH₃ | (CH₃)₃C | CH≡CCH₂ |
| CH₃ | (CH₃)₃C | CH₃C≡CCH₂ |
| CH₃ | (CH₃)₃C | CH₃CH₂C≡CCH₂ |
| CH₃ | (CH₃)₃C | CH₃C≡CCH₂CH₂ |
| CH₃ | (CH₃)₃C | CH≡C—(CH₃)CH |
| CH₃ | (CH₃)₃C | N≡CCH₂ |
| CH₃ | (CH₃)₃C | N≡CCH₂CH₂ |
| CH₃ | (CH₃)₃C | N≡CCH₂CH₂CH₂ |
| CH₃ | (CH₃)₃C | N≡CCH₂CH₂CH₂CH₂ |
| CH₃ | (CH₃)₃C | H |
| CH₃ | (CH₃)₃C | C₆H₅—CH₂ |
| CH₃ | (CH₃)₃C | 2-F—C₆H₄—CH₂ |
| CH₃ | (CH₃)₃C | 3-F—C₆H₄—CH₂ |
| CH₃ | (CH₃)₃C | 4-F—C₆H₄—CH₂ |
| CH₃ | (CH₃)₃C | 2-Cl—C₆H₄—CH₂ |
| CH₃ | (CH₃)₃C | 3-Cl—C₆H₄—CH₂ |
| CH₃ | (CH₃)₃C | 4-Cl—C₆H₄—CH₂ |
| CH₃ | (CH₃)₃C | 2-Br—C₆H₄—CH₂ |
| CH₃ | (CH₃)₃C | 3-Br—C₆H₄—CH₂ |
| CH₃ | (CH₃)₃C | 4-Br—C₆H₄—CH₂ |
| CH₃ | (CH₃)₃C | 4-I—C₆H₄—CH₂ |
| CH₃ | (CH₃)₃C | 2-CH₃—C₆H₄—CH₂ |
| CH₃ | (CH₃)₃C | 3-CH₃—C₆H₄—CH₂ |
| CH₃ | (CH₃)₃C | 4-CH₃—C₆H₄—CH₂ |
| CH₃ | (CH₃)₃C | 4-CF₃—C₆H₄—CH₂ |
| CH₃ | (CH₃)₃C | 4-CH₃CH₂—C₆H₄—CH₂ |
| CH₃ | (CH₃)₃C | 4-(CH₃)₂CH—C₆H₄—CH₂ |
| CH₃ | (CH₃)₃C | 4-CH₃CH₂CH₂—C₆H₄—CH₂ |
| CH₃ | (CH₃)₃C | 4-(CH₃)₃C—C₆H₄—CH₂ |
| CH₃ | (CH₃)₃C | 2,4-(CH₃)₂—C₆H₃—CH₂ |
| CH₃ | (CH₃)₃C | 2,4,6-(CH₃)₃—C₆H₂—CH₂ |
| CH₃ | (CH₃)₃C | 2,4-Cl₂—C₆H₃—CH₂ |
| CH₃ | (CH₃)₃C | 3,4-Cl₂—C₆H₃—CH₂ |
| CH₃ | (CH₃)₃C | 2,5-Cl₂—C₆H₃—CH₂ |
| CH₃ | (CH₃)₃C | 3,5-Cl₂—C₆H₃—CH₂ |
| CH₃ | (CH₃)₃C | 2,6-Cl₂—C₆H₃—CH₂ |
| CH₃ | (CH₃)₃C | 4-CH₃O—C₆H₄—CH₂ |
| CH₃ | (CH₃)₃C | 4-CF₃O—C₆H₄—CH₂ |
| CH₃ | (CH₃)₃C | 4-CH₃CH₂O—C₆H₄—CH₂ |
| CH₃ | (CH₃)₃C | 4-(CH₃)₂CHO—C₆H₄—CH₂ |
| CH₃ | (CH₃)₃C | 4-(CH₃)₃CO—C₆H₄—CH₂ |
| CH₃ | (CH₃)₃C | 4-CH₃OC(=O)—C₆H₄—CH₂ |
| CH₃ | (CH₃)₃C | 4-CH₃CH₂OC(=O)—C₆H₄—CH₂ |
| CH₃ | (CH₃)₃C | 4-CH₃CH₂CH₂OC(=O)—C₆H₄—CH₂ |
| CH₃ | (CH₃)₃C | 4-(CH₃)₂CHOC(=O)—C₆H₄—CH₂ |
| CH₃ | (CH₃)₃C | 4-(CH₃)₃COC(=O)—C₆H₄—CH₂ |
| CH₃ | (CH₃)₃C | CH₂Cl—CH₂ |
| CH₃ | (CH₃)₃C | CCl=CCH₂ |
| CH₃ | (CH₃)₃C | CBr=CCH₂ |
| CH₃CH₂ | CH₃ | CH₃ |
| CH₃CH₂ | CH₃ | CH₃CH₂ |
| CH₃CH₂ | CH₃ | CH₃CH₂CH₂ |
| CH₃CH₂ | CH₃ | (CH₃)₂CH |
| CH₃CH₂ | CH₃ | CH₃CH₂CH₂CH₂ |
| CH₃CH₂ | CH₃ | CH₃CH₂—(CH₃)CH |
| CH₃CH₂ | CH₃ | (CH₃)₂CHCH₂ |
| CH₃CH₂ | CH₃ | (CH₃)₃C |
| CH₃CH₂ | CH₃ | CH₃CH₂CH₂CH₂CH₂ |
| CH₃CH₂ | CH₃ | (CH₃)₂CHCH₂CH₂ |
| CH₃CH₂ | CH₃ | (CH₃)₃CCH₂ |
| CH₃CH₂ | CH₃ | CH₃CH₂CH₂—(CH₃)CH |
| CH₃CH₂ | CH₃ | (CH₃)₂CH—(CH₃)CH |
| CH₃CH₂ | CH₃ | CH₃CH₂CH₂CH₂CH₂CH₂ |
| CH₃CH₂ | CH₃ | CH₂F |
| CH₃CH₂ | CH₃ | CH₂F—CH₂ |
| CH₃CH₂ | CH₃ | CF₃CH₂ |
| CH₃CH₂ | CH₃ | CF₃CH₂CH₂ |
| CH₃CH₂ | CH₃ | CF₃CH₂CH₂CH₂ |
| CH₃CH₂ | CH₃ | CF₃CH₂CH₂CH₂CH₂ |
| CH₃CH₂ | CH₃ | CH₂Cl—CH₂CH₂ |
| CH₃CH₂ | CH₃ | CH₂Br—CH₂CH₂ |
| CH₃CH₂ | CH₃ | CH₂Cl—CH₂CH₂CH₂ |
| CH₃CH₂ | CH₃ | CH₂Br—CH₂CH₂CH₂ |
| CH₃CH₂ | CH₃ | CH₂Cl—CH₂CH₂CH₂CH₂ |
| CH₃CH₂ | CH₃ | CH₂Br—CH₂CH₂CH₂CH₂ |
| CH₃CH₂ | CH₃ | CH₂=CHCH₂ |
| CH₃CH₂ | CH₃ | CH₂=C(CH₃)—CH₂ |
| CH₃CH₂ | CH₃ | (CH₃)₂C=CHCH₂ |
| CH₃CH₂ | CH₃ | CH₃CH=CHCH₂ |
| CH₃CH₂ | CH₃ | CH₂=CHCH₂CH₂ |
| CH₃CH₂ | CH₃ | CH₃CH₂CH=CHCH₂ |
| CH₃CH₂ | CH₃ | CH₃CH=CHCH₂CH₂ |
| CH₃CH₂ | CH₃ | CH₃CH₂CH₂CH=CHCH₂ |
| CH₃CH₂ | CH₃ | CH₃CH₂CH=CHCH₂CH₂ |
| CH₃CH₂ | CH₃ | CHCl=CHCH₂ |
| CH₃CH₂ | CH₃ | CCl₂=CHCH₂ |
| CH₃CH₂ | CH₃ | CHBr=CHCH₂ |
| CH₃CH₂ | CH₃ | CBr₂=CHCH₂ |
| CH₃CH₂ | CH₃ | CH₂=CClCH₂ |
| CH₃CH₂ | CH₃ | CH₂=CBrCH₂ |
| CH₃CH₂ | CH₃ | CH₂=CFCH₂ |
| CH₃CH₂ | CH₃ | CHCl=CClCH₂ |
| CH₃CH₂ | CH₃ | CHBr=CBrCH₂ |
| CH₃CH₂ | CH₃ | CH₃CCl=CHCH₂ |
| CH₃CH₂ | CH₃ | CF₃CCl=CHCH₂ |
| CH₃CH₂ | CH₃ | CClH₂CH=CHCH₂ |
| CH₃CH₂ | CH₃ | CBrH₂CH=CHCH₂ |
| CH₃CH₂ | CH₃ | CF₂=CFCH₂ |
| CH₃CH₂ | CH₃ | CH≡CCH₂ |
| CH₃CH₂ | CH₃ | CH₃C≡CCH₂ |
| CH₃CH₂ | CH₃ | CH₃CH₂C≡CCH₂ |
| CH₃CH₂ | CH₃ | CH₃C≡CCH₂CH₂ |
| CH₃CH₂ | CH₃ | CH≡C—(CH₃)CH |
| CH₃CH₂ | CH₃ | N≡CCH₂ |
| CH₃CH₂ | CH₃ | N≡CCH₂CH₂ |
| CH₃CH₂ | CH₃ | N≡CCH₂CH₂CH₂ |
| CH₃CH₂ | CH₃ | N≡CCH₂CH₂CH₂CH₂ |

TABLE 1-continued (X represents R⁸O—N)

| R¹ | R² | R⁸ |
|---|---|---|
| CH₃CH₂ | CH₃ | H |
| CH₃CH₂ | CH₃ | C₆H₅—CH₂ |
| CH₃CH₂ | CH₃ | 2-F—C₆H₄—CH₂ |
| CH₃CH₂ | CH₃ | 3-F—C₆H₄—CH₂ |
| CH₃CH₂ | CH₃ | 4-F—C₆H₄—CH₂ |
| CH₃CH₂ | CH₃ | 2-Cl—C₆H₄—CH₂ |
| CH₃CH₂ | CH₃ | 3-Cl—C₆H₄—CH₂ |
| CH₃CH₂ | CH₃ | 4-Cl—C₆H₄—CH₂ |
| CH₃CH₂ | CH₃ | 2-Br—C₆H₄—CH₂ |
| CH₃CH₂ | CH₃ | 3-Br—C₆H₄—CH₂ |
| CH₃CH₂ | CH₃ | 4-Br—C₆H₄—CH₂ |
| CH₃CH₂ | CH₃ | 4-I—C₆H₄—CH₂ |
| CH₃CH₂ | CH₃ | 2-CH₃—C₆H₄—CH₂ |
| CH₃CH₂ | CH₃ | 3-CH₃—C₆H₄—CH₂ |
| CH₃CH₂ | CH₃ | 4-CH₃—C₆H₄—CH₂ |
| CH₃CH₂ | CH₃ | 4-CF₃—C₆H₄—CH₂ |
| CH₃CH₂ | CH₃ | 4-CH₃CH₂—C₆H₄—CH₂ |
| CH₃CH₂ | CH₃ | 4-(CH₃)₂CH—C₆H₄—CH₂ |
| CH₃CH₂ | CH₃ | 4-CH₃CH₂CH₂—C₆H₄—CH₂ |
| CH₃CH₂ | CH₃ | 4-(CH₃)₃C—C₆H₄—CH₂ |
| CH₃CH₂ | CH₃ | 2,4-(CH₃)₂—C₆H₃—CH₂ |
| CH₃CH₂ | CH₃ | 2,4,6-(CH₃)₃—C₆H₂—CH₂ |
| CH₃CH₂ | CH₃ | 2,4-Cl₂—C₆H₃—CH₂ |
| CH₃CH₂ | CH₃ | 3,4-Cl₂—C₆H₃—CH₂ |
| CH₃CH₂ | CH₃ | 2,5-Cl₂—C₆H₃—CH₂ |
| CH₃CH₂ | CH₃ | 3,5-Cl₂—C₆H₃—CH₂ |
| CH₃CH₂ | CH₃ | 2,6-Cl₂—C₆H₃—CH₂ |
| CH₃CH₂ | CH₃ | 4-CH₃O—C₆H₄—CH₂ |
| CH₃CH₂ | CH₃ | 4-CF₃O—C₆H₄—CH₂ |
| CH₃CH₂ | CH₃ | 4-CH₃CH₂O—C₆H₄—CH₂ |
| CH₃CH₂ | CH₃ | 4-(CH₃)₂CHO—C₆H₄—CH₂ |
| CH₃CH₂ | CH₃ | 4-(CH₃)₃CO—C₆H₄—CH₂ |
| CH₃CH₂ | CH₃ | 4-CH₃OC(=O)—C₆H₄—CH₂ |
| CH₃CH₂ | CH₃ | 4-CH₃CH₂OC(=O)—C₆H₄—CH₂ |
| CH₃CH₂ | CH₃ | 4-CH₃CH₂CH₂OC(=O)—C₆H₄—CH₂ |
| CH₃CH₂ | CH₃ | 4-(CH₃)₂CHOC(=O)—C₆H₄—CH₂ |
| CH₃CH₂ | CH₃ | 4-(CH₃)₃COC(=O)—C₆H₄—CH₂ |
| CH₃CH₂ | CH₃ | CH₂Cl—CH₂ |
| CH₃CH₂ | CH₃ | CCl=CCH₂ |
| CH₃CH₂ | CH₃ | CBr=CCH₂ |
| CH₃CH₂ | CH₃CH₂ | CH₃ |
| CH₃CH₂ | CH₃CH₂ | CH₃CH₂ |
| CH₃CH₂ | CH₃CH₂ | CH₃CH₂CH₂ |
| CH₃CH₂ | CH₃CH₂ | (CH₃)₂CH |
| CH₃CH₂ | CH₃CH₂ | CH₃CH₂CH₂CH₂ |
| CH₃CH₂ | CH₃CH₂ | CH₃CH₂—(CH₃)CH |
| CH₃CH₂ | CH₃CH₂ | (CH₃)₂CHCH₂ |
| CH₃CH₂ | CH₃CH₂ | (CH₃)₃C |
| CH₃CH₂ | CH₃CH₂ | CH₃CH₂CH₂CH₂CH₂ |
| CH₃CH₂ | CH₃CH₂ | (CH₃)₂CHCH₂CH₂ |
| CH₃CH₂ | CH₃CH₂ | (CH₃)₃CCH₂ |
| CH₃CH₂ | CH₃CH₂ | CH₃CH₂CH₂—(CH₃)CH |
| CH₃CH₂ | CH₃CH₂ | (CH₃)₂CH—(CH₃)CH |
| CH₃CH₂ | CH₃CH₂ | CH₃CH₂CH₂CH₂CH₂CH₂ |
| CH₃CH₂ | CH₃CH₂ | CH₂F |
| CH₃CH₂ | CH₃CH₂ | CH₂F—CH₂ |
| CH₃CH₂ | CH₃CH₂ | CF₃CH₂ |
| CH₃CH₂ | CH₃CH₂ | CF₃CH₂CH₂ |
| CH₃CH₂ | CH₃CH₂ | CF₃CH₂CH₂CH₂ |
| CH₃CH₂ | CH₃CH₂ | CF₃CH₂CH₂CH₂CH₂ |
| CH₃CH₂ | CH₃CH₂ | CH₂Cl—CH₂CH₂ |
| CH₃CH₂ | CH₃CH₂ | CH₂Br—CH₂CH₂ |
| CH₃CH₂ | CH₃CH₂ | CH₂Cl—CH₂CH₂CH₂ |
| CH₃CH₂ | CH₃CH₂ | CH₂Br—CH₂CH₂CH₂ |
| CH₃CH₂ | CH₃CH₂ | CH₂Cl—CH₂CH₂CH₂CH₂ |
| CH₃CH₂ | CH₃CH₂ | CH₂Br—CH₂CH₂CH₂CH₂ |
| CH₃CH₂ | CH₃CH₂ | CH₂=CHCH₂ |
| CH₃CH₂ | CH₃CH₂ | CH₂=C(CH₃)—CH₂ |
| CH₃CH₂ | CH₃CH₂ | (CH₃)₂C=CHCH₂ |
| CH₃CH₂ | CH₃CH₂ | CH₃CH=CHCH₂ |
| CH₃CH₂ | CH₃CH₂ | CH₂=CHCH₂CH₂ |
| CH₃CH₂ | CH₃CH₂ | CH₃CH₂CH=CHCH₂ |
| CH₃CH₂ | CH₃CH₂ | CH₃CH=CHCH₂CH₂ |
| CH₃CH₂ | CH₃CH₂ | CH₃CH₂CH₂CH=CHCH₂ |
| CH₃CH₂ | CH₃CH₂ | CH₃CH₂CH=CHCH₂CH₂ |
| CH₃CH₂ | CH₃CH₂ | CHCl=CHCH₂ |
| CH₃CH₂ | CH₃CH₂ | CCl₂=CHCH₂ |
| CH₃CH₂ | CH₃CH₂ | CHBr=CHCH₂ |
| CH₃CH₂ | CH₃CH₂ | CBr₂=CHCH₂ |
| CH₃CH₂ | CH₃CH₂ | CH₂=CClCH₂ |
| CH₃CH₂ | CH₃CH₂ | CH₂=CBrCH₂ |
| CH₃CH₂ | CH₃CH₂ | CH₂=CFCH₂ |
| CH₃CH₂ | CH₃CH₂ | CHCl=CClCH₂ |
| CH₃CH₂ | CH₃CH₂ | CHBr=CBrCH₂ |
| CH₃CH₂ | CH₃CH₂ | CH₃CCl=CHCH₂ |
| CH₃CH₂ | CH₃CH₂ | CF₃CCl=CHCH₂ |
| CH₃CH₂ | CH₃CH₂ | CClH₂CH=CHCH₂ |
| CH₃CH₂ | CH₃CH₂ | CBrH₂CH=CHCH₂ |
| CH₃CH₂ | CH₃CH₂ | CF₂=CFCH₂ |
| CH₃CH₂ | CH₃CH₂ | CH≡CCH₂ |
| CH₃CH₂ | CH₃CH₂ | CH₃C≡CCH₂ |
| CH₃CH₂ | CH₃CH₂ | CH₃CH₂C≡CCH₂ |
| CH₃CH₂ | CH₃CH₂ | CH₃C≡CCH₂CH₂ |
| CH₃CH₂ | CH₃CH₂ | CH≡C—(CH₃)CH |
| CH₃CH₂ | CH₃CH₂ | N≡CCH₂ |
| CH₃CH₂ | CH₃CH₂ | N≡CCH₂CH₂ |
| CH₃CH₂ | CH₃CH₂ | N≡CCH₂CH₂CH₂ |
| CH₃CH₂ | CH₃CH₂ | N≡CCH₂CH₂CH₂CH₂ |
| CH₃CH₂ | CH₃CH₂ | H |
| CH₃CH₂ | CH₃CH₂ | C₆H₅—CH₂ |
| CH₃CH₂ | CH₃CH₂ | 2-F—C₆H₄—CH₂ |
| CH₃CH₂ | CH₃CH₂ | 3-F—C₆H₄—CH₂ |
| CH₃CH₂ | CH₃CH₂ | 4-F—C₆H₄—CH₂ |
| CH₃CH₂ | CH₃CH₂ | 2-Cl—C₆H₄—CH₂ |
| CH₃CH₂ | CH₃CH₂ | 3-Cl—C₆H₄—CH₂ |
| CH₃CH₂ | CH₃CH₂ | 4-Cl—C₆H₄—CH₂ |
| CH₃CH₂ | CH₃CH₂ | 2-Br—C₆H₄—CH₂ |
| CH₃CH₂ | CH₃CH₂ | 3-Br—C₆H₄—CH₂ |
| CH₃CH₂ | CH₃CH₂ | 4-Br—C₆H₄—CH₂ |
| CH₃CH₂ | CH₃CH₂ | 4-I—C₆H₄—CH₂ |
| CH₃CH₂ | CH₃CH₂ | 2-CH₃—C₆H₄—CH₂ |
| CH₃CH₂ | CH₃CH₂ | 3-CH₃—C₆H₄—CH₂ |
| CH₃CH₂ | CH₃CH₂ | 4-CH₃—C₆H₄—CH₂ |
| CH₃CH₂ | CH₃CH₂ | 4-CF₃—C₆H₄—CH₂ |
| CH₃CH₂ | CH₃CH₂ | 4-CH₃CH₂—C₆H₄—CH₂ |
| CH₃CH₂ | CH₃CH₂ | 4-(CH₃)₂CH—C₆H₄—CH₂ |
| CH₃CH₂ | CH₃CH₂ | 4-CH₃CH₂CH₂—C₆H₄—CH₂ |
| CH₃CH₂ | CH₃CH₂ | 4-(CH₃)₃C—C₆H₄—CH₂ |
| CH₃CH₂ | CH₃CH₂ | 2,4-(CH₃)₂—C₆H₃—CH₂ |
| CH₃CH₂ | CH₃CH₂ | 2,4,6-(CH₃)₃—C₆H₂—CH₂ |
| CH₃CH₂ | CH₃CH₂ | 2,4-Cl₂—C₆H₃—CH₂ |
| CH₃CH₂ | CH₃CH₂ | 3,4-Cl₂—C₆H₃—CH₂ |
| CH₃CH₂ | CH₃CH₂ | 2,5-Cl₂—C₆H₃—CH₂ |
| CH₃CH₂ | CH₃CH₂ | 3,5-Cl₂—C₆H₃—CH₂ |
| CH₃CH₂ | CH₃CH₂ | 2,6-Cl₂—C₆H₃—CH₂ |
| CH₃CH₂ | CH₃CH₂ | 4-CH₃O—C₆H₄—CH₂ |
| CH₃CH₂ | CH₃CH₂ | 4-CF₃O—C₆H₄—CH₂ |
| CH₃CH₂ | CH₃CH₂ | 4-CH₃CH₂O—C₆H₄—CH₂ |
| CH₃CH₂ | CH₃CH₂ | 4-(CH₃)₂CHO—C₆H₄—CH₂ |
| CH₃CH₂ | CH₃CH₂ | 4-(CH₃)₃CO—C₆H₄—CH₂ |
| CH₃CH₂ | CH₃CH₂ | 4-CH₃OC(=O)—C₆H₄—CH₂ |
| CH₃CH₂ | CH₃CH₂ | 4-CH₃CH₂OC(=O)—C₆H₄—CH₂ |
| CH₃CH₂ | CH₃CH₂ | 4-CH₃CH₂CH₂OC(=O)—C₆H₄—CH₂ |
| CH₃CH₂ | CH₃CH₂ | 4-(CH₃)₂CHOC(=O)—C₆H₄—CH₂ |
| CH₃CH₂ | CH₃CH₂ | 4-(CH₃)₃COC(=O)—C₆H₄—CH₂ |
| CH₃CH₂ | CH₃CH₂ | CH₂Cl—CH₂ |
| CH₃CH₂ | CH₃CH₂ | CCl=CCH₂ |
| CH₃CH₂ | CH₃CH₂ | CBr=CCH₂ |
| CH₃CH₂ | (CH₃)₂CH | CH₃ |
| CH₃CH₂ | (CH₃)₂CH | CH₃CH₂ |
| CH₃CH₂ | (CH₃)₂CH | CH₃CH₂CH₂ |
| CH₃CH₂ | (CH₃)₂CH | (CH₃)₂CH |
| CH₃CH₂ | (CH₃)₂CH | CH₃CH₂CH₂CH₂ |
| CH₃CH₂ | (CH₃)₂CH | CH₃CH₂—(CH₃)CH |
| CH₃CH₂ | (CH₃)₂CH | (CH₃)₂CHCH₂ |
| CH₃CH₂ | (CH₃)₂CH | (CH₃)₃C |
| CH₃CH₂ | (CH₃)₂CH | CH₃CH₂CH₂CH₂CH₂ |
| CH₃CH₂ | (CH₃)₂CH | (CH₃)₂CHCH₂CH₂ |
| CH₃CH₂ | (CH₃)₂CH | (CH₃)₃CCH₂ |
| CH₃CH₂ | (CH₃)₂CH | CH₃CH₂CH₂—(CH₃)CH |

TABLE 1-continued (X represents $R^8O$—N)

| $R^1$ | $R^2$ | $R^8$ |
|---|---|---|
| $CH_3CH_2$ | $(CH_3)_2CH$ | $(CH_3)_2CH$—$(CH_3)CH$ |
| $CH_3CH_2$ | $(CH_3)_2CH$ | $CH_3CH_2CH_2CH_2CH_2$ |
| $CH_3CH_2$ | $(CH_3)_2CH$ | $CH_2F$ |
| $CH_3CH_2$ | $(CH_3)_2CH$ | $CH_2F$—$CH_2$ |
| $CH_3CH_2$ | $(CH_3)_2CH$ | $CF_3CH_2$ |
| $CH_3CH_2$ | $(CH_3)_2CH$ | $CF_3CH_2CH_2$ |
| $CH_3CH_2$ | $(CH_3)_2CH$ | $CF_3CH_2CH_2CH_2$ |
| $CH_3CH_2$ | $(CH_3)_2CH$ | $CF_3CH_2CH_2CH_2CH_2$ |
| $CH_3CH_2$ | $(CH_3)_2CH$ | $CH_2Cl$—$CH_2CH_2$ |
| $CH_3CH_2$ | $(CH_3)_2CH$ | $CH_2Br$—$CH_2CH_2$ |
| $CH_3CH_2$ | $(CH_3)_2CH$ | $CH_2Cl$—$CH_2CH_2CH_2$ |
| $CH_3CH_2$ | $(CH_3)_2CH$ | $CH_2Br$—$CH_2CH_2CH_2$ |
| $CH_3CH_2$ | $(CH_3)_2CH$ | $CH_2Cl$—$CH_2CH_2CH_2CH_2$ |
| $CH_3CH_2$ | $(CH_3)_2CH$ | $CH_2Br$—$CH_2CH_2CH_2CH_2$ |
| $CH_3CH_2$ | $(CH_3)_2CH$ | $CH_2$=$CHCH_2$ |
| $CH_3CH_2$ | $(CH_3)_2CH$ | $CH_2$=$C(CH_3)$—$CH_2$ |
| $CH_3CH_2$ | $(CH_3)_2CH$ | $(CH_3)_2C$=$CHCH_2$ |
| $CH_3CH_2$ | $(CH_3)_2CH$ | $CH_3CH$=$CHCH_2$ |
| $CH_3CH_2$ | $(CH_3)_2CH$ | $CH_2$=$CHCH_2CH_2$ |
| $CH_3CH_2$ | $(CH_3)_2CH$ | $CH_3CH_2CH$=$CHCH_2$ |
| $CH_3CH_2$ | $(CH_3)_2CH$ | $CH_3CH$=$CHCH_2CH_2$ |
| $CH_3CH_2$ | $(CH_3)_2CH$ | $CH_3CH_2CH_2CH$=$CHCH_2$ |
| $CH_3CH_2$ | $(CH_3)_2CH$ | $CH_3CH_2CH$=$CHCH_2CH_2$ |
| $CH_3CH_2$ | $(CH_3)_2CH$ | $CHCl$=$CHCH_2$ |
| $CH_3CH_2$ | $(CH_3)_2CH$ | $CCl_2$=$CHCH_2$ |
| $CH_3CH_2$ | $(CH_3)_2CH$ | $CHBr$=$CHCH_2$ |
| $CH_3CH_2$ | $(CH_3)_2CH$ | $CBr_2$=$CHCH_2$ |
| $CH_3CH_2$ | $(CH_3)_2CH$ | $CH_2$=$CClCH_2$ |
| $CH_3CH_2$ | $(CH_3)_2CH$ | $CH_2$=$CBrCH_2$ |
| $CH_3CH_2$ | $(CH_3)_2CH$ | $CH_2$=$CFCH_2$ |
| $CH_3CH_2$ | $(CH_3)_2CH$ | $CHCl$=$CClCH_2$ |
| $CH_3CH_2$ | $(CH_3)_2CH$ | $CHBr$=$CBrCH_2$ |
| $CH_3CH_2$ | $(CH_3)_2CH$ | $CH_3CCl$=$CHCH_2$ |
| $CH_3CH_2$ | $(CH_3)_2CH$ | $CF_3CCl$=$CHCH_2$ |
| $CH_3CH_2$ | $(CH_3)_2CH$ | $CClH_2CH$=$CHCH_2$ |
| $CH_3CH_2$ | $(CH_3)_2CH$ | $CBrH_2CH$=$CHCH_2$ |
| $CH_3CH_2$ | $(CH_3)_2CH$ | $CF_2$=$CFCH_2$ |
| $CH_3CH_2$ | $(CH_3)_2CH$ | $CH$≡$CCH_2$ |
| $CH_3CH_2$ | $(CH_3)_2CH$ | $CH_3C$≡$CCH_2$ |
| $CH_3CH_2$ | $(CH_3)_2CH$ | $CH_3CH_2C$≡$CCH_2$ |
| $CH_3CH_2$ | $(CH_3)_2CH$ | $CH_3C$≡$CCH_2CH_2$ |
| $CH_3CH_2$ | $(CH_3)_2CH$ | $CH$≡$C$—$(CH_3)CH$ |
| $CH_3CH_2$ | $(CH_3)_2CH$ | $N$≡$CCH_2$ |
| $CH_3CH_2$ | $(CH_3)_2CH$ | $N$≡$CCH_2CH_2$ |
| $CH_3CH_2$ | $(CH_3)_2CH$ | $N$≡$CCH_2CH_2CH_2$ |
| $CH_3CH_2$ | $(CH_3)_2CH$ | $N$≡$CCH_2CH_2CH_2CH_2$ |
| $CH_3CH_2$ | $(CH_3)_2CH$ | H |
| $CH_3CH_2$ | $(CH_3)_2CH$ | $C_6H_5$—$CH_2$ |
| $CH_3CH_2$ | $(CH_3)_2CH$ | 2-F—$C_6H_4$—$CH_2$ |
| $CH_3CH_2$ | $(CH_3)_2CH$ | 3-F—$C_6H_4$—$CH_2$ |
| $CH_3CH_2$ | $(CH_3)_2CH$ | 4-F—$C_6H_4$—$CH_2$ |
| $CH_3CH_2$ | $(CH_3)_2CH$ | 2-Cl—$C_6H_4$—$CH_2$ |
| $CH_3CH_2$ | $(CH_3)_2CH$ | 3-Cl—$C_6H_4$—$CH_2$ |
| $CH_3CH_2$ | $(CH_3)_2CH$ | 4-Cl—$C_6H_4$—$CH_2$ |
| $CH_3CH_2$ | $(CH_3)_2CH$ | 2-Br—$C_6H_4$—$CH_2$ |
| $CH_3CH_2$ | $(CH_3)_2CH$ | 3-Br—$C_6H_4$—$CH_2$ |
| $CH_3CH_2$ | $(CH_3)_2CH$ | 4-Br—$C_6H_4$—$CH_2$ |
| $CH_3CH_2$ | $(CH_3)_2CH$ | 4-I—$C_6H_4$—$CH_2$ |
| $CH_3CH_2$ | $(CH_3)_2CH$ | 2-$CH_3$—$C_6H_4$—$CH_2$ |
| $CH_3CH_2$ | $(CH_3)_2CH$ | 3-$CH_3$—$C_6H_4$—$CH_2$ |
| $CH_3CH_2$ | $(CH_3)_2CH$ | 4-$CH_3$—$C_6H_4$—$CH_2$ |
| $CH_3CH_2$ | $(CH_3)_2CH$ | 4-$CF_3$—$C_6H_4$—$CH_2$ |
| $CH_3CH_2$ | $(CH_3)_2CH$ | 4-$CH_3CH_2$—$C_6H_4$—$CH_2$ |
| $CH_3CH_2$ | $(CH_3)_2CH$ | 4-$(CH_3)_2CH$—$C_6H_4$—$CH_2$ |
| $CH_3CH_2$ | $(CH_3)_2CH$ | 4-$CH_3CH_2CH_2$—$C_6H_4$—$CH_2$ |
| $CH_3CH_2$ | $(CH_3)_2CH$ | 4-$(CH_3)_3C$—$C_6H_4$—$CH_2$ |
| $CH_3CH_2$ | $(CH_3)_2CH$ | 2,4-$(CH_3)_2$—$C_6H_3$—$CH_2$ |
| $CH_3CH_2$ | $(CH_3)_2CH$ | 2,4,6-$(CH_3)_3$—$C_6H_2$—$CH_2$ |
| $CH_3CH_2$ | $(CH_3)_2CH$ | 2,4-$Cl_2$—$C_6H_3$—$CH_2$ |
| $CH_3CH_2$ | $(CH_3)_2CH$ | 3,4-$Cl_2$—$C_6H_3$—$CH_2$ |
| $CH_3CH_2$ | $(CH_3)_2CH$ | 2,5-$Cl_2$—$C_6H_3$—$CH_2$ |
| $CH_3CH_2$ | $(CH_3)_2CH$ | 3,5-$Cl_2$—$C_6H_3$—$CH_2$ |
| $CH_3CH_2$ | $(CH_3)_2CH$ | 2,6-$Cl_2$—$C_6H_3$—$CH_2$ |
| $CH_3CH_2$ | $(CH_3)_2CH$ | 4-$CH_3O$—$C_6H_4$—$CH_2$ |
| $CH_3CH_2$ | $(CH_3)_2CH$ | 4-$CF_3O$—$C_6H_4$—$CH_2$ |
| $CH_3CH_2$ | $(CH_3)_2CH$ | 4-$CH_3CH_2O$—$C_6H_4$—$CH_2$ |
| $CH_3CH_2$ | $(CH_3)_2CH$ | 4-$(CH_3)_2CHO$—$C_6H_4$—$CH_2$ |
| $CH_3CH_2$ | $(CH_3)_2CH$ | 4-$(CH_3)_3CO$—$C_6H_4$—$CH_2$ |
| $CH_3CH_2$ | $(CH_3)_2CH$ | 4-$CH_3OC(=O)$—$C_6H_4$—$CH_2$ |
| $CH_3CH_2$ | $(CH_3)_2CH$ | 4-$CH_3CH_2OC(=O)$—$C_6H_4$—$CH_2$ |
| $CH_3CH_2$ | $(CH_3)_2CH$ | 4-$CH_3CH_2CH_2OC(=O)$—$C_6H_4$—$CH_2$ |
| $CH_3CH_2$ | $(CH_3)_2CH$ | 4-$(CH_3)_2CHOC(=O)$—$C_6H_4$—$CH_2$ |
| $CH_3CH_2$ | $(CH_3)_2CH$ | 4-$(CH_3)_3COC(=O)$—$C_6H_4$—$CH_2$ |
| $CH_3CH_2$ | $(CH_3)_2CH$ | $CH_2Cl$—$CH_2$ |
| $CH_3CH_2$ | $(CH_3)_2CH$ | $CCl$≡$CCH_2$ |
| $CH_3CH_2$ | $(CH_3)_2CH$ | $CBr$≡$CCH_2$ |
| $CH_3CH_2$ | $(CH_3)_3C$ | $CH_3$ |
| $CH_3CH_2$ | $(CH_3)_3C$ | $CH_3CH_2$ |
| $CH_3CH_2$ | $(CH_3)_3C$ | $CH_3CH_2CH_2$ |
| $CH_3CH_2$ | $(CH_3)_3C$ | $(CH_3)_2CH$ |
| $CH_3CH_2$ | $(CH_3)_3C$ | $CH_3CH_2CH_2CH_2$ |
| $CH_3CH_2$ | $(CH_3)_3C$ | $CH_3CH_2$—$(CH_3)CH$ |
| $CH_3CH_2$ | $(CH_3)_3C$ | $(CH_3)_2CHCH_2$ |
| $CH_3CH_2$ | $(CH_3)_3C$ | $(CH_3)_3C$ |
| $CH_3CH_2$ | $(CH_3)_3C$ | $CH_3CH_2CH_2CH_2CH_2$ |
| $CH_3CH_2$ | $(CH_3)_3C$ | $(CH_3)_2CHCH_2CH_2$ |
| $CH_3CH_2$ | $(CH_3)_3C$ | $(CH_3)_3CCH_2$ |
| $CH_3CH_2$ | $(CH_3)_3C$ | $CH_3CH_2CH_2$—$(CH_3)CH$ |
| $CH_3CH_2$ | $(CH_3)_3C$ | $(CH_3)_2CH$—$(CH_3)CH$ |
| $CH_3CH_2$ | $(CH_3)_3C$ | $CH_3CH_2CH_2CH_2CH_2$ |
| $CH_3CH_2$ | $(CH_3)_3C$ | $CH_2F$ |
| $CH_3CH_2$ | $(CH_3)_3C$ | $CH_2F$—$CH_2$ |
| $CH_3CH_2$ | $(CH_3)_3C$ | $CF_3CH_2$ |
| $CH_3CH_2$ | $(CH_3)_3C$ | $CF_3CH_2CH_2$ |
| $CH_3CH_2$ | $(CH_3)_3C$ | $CF_3CH_2CH_2CH_2$ |
| $CH_3CH_2$ | $(CH_3)_3C$ | $CF_3CH_2CH_2CH_2CH_2$ |
| $CH_3CH_2$ | $(CH_3)_3C$ | $CH_2Cl$—$CH_2CH_2$ |
| $CH_3CH_2$ | $(CH_3)_3C$ | $CH_2Br$—$CH_2CH_2$ |
| $CH_3CH_2$ | $(CH_3)_3C$ | $CH_2Cl$—$CH_2CH_2CH_2$ |
| $CH_3CH_2$ | $(CH_3)_3C$ | $CH_2Br$—$CH_2CH_2CH_2$ |
| $CH_3CH_2$ | $(CH_3)_3C$ | $CH_2Cl$—$CH_2CH_2CH_2CH_2$ |
| $CH_3CH_2$ | $(CH_3)_3C$ | $CH_2Br$—$CH_2CH_2CH_2CH_2$ |
| $CH_3CH_2$ | $(CH_3)_3C$ | $CH_2$=$CHCH_2$ |
| $CH_3CH_2$ | $(CH_3)_3C$ | $CH_2$=$C(CH_3)$—$CH_2$ |
| $CH_3CH_2$ | $(CH_3)_3C$ | $(CH_3)_2C$=$CHCH_2$ |
| $CH_3CH_2$ | $(CH_3)_3C$ | $CH_3CH$=$CHCH_2$ |
| $CH_3CH_2$ | $(CH_3)_3C$ | $CH_2$=$CHCH_2CH_2$ |
| $CH_3CH_2$ | $(CH_3)_3C$ | $CH_3CH_2CH$=$CHCH_2$ |
| $CH_3CH_2$ | $(CH_3)_3C$ | $CH_3CH$=$CHCH_2CH_2$ |
| $CH_3CH_2$ | $(CH_3)_3C$ | $CH_3CH_2CH_2CH$=$CHCH_2$ |
| $CH_3CH_2$ | $(CH_3)_3C$ | $CH_3CH_2CH$=$CHCH_2CH_2$ |
| $CH_3CH_2$ | $(CH_3)_3C$ | $CHCl$=$CHCH_2$ |
| $CH_3CH_2$ | $(CH_3)_3C$ | $CCl_2$=$CHCH_2$ |
| $CH_3CH_2$ | $(CH_3)_3C$ | $CHBr$=$CHCH_2$ |
| $CH_3CH_2$ | $(CH_3)_3C$ | $CBr_2$=$CHCH_2$ |
| $CH_3CH_2$ | $(CH_3)_3C$ | $CH_2$=$CClCH_2$ |
| $CH_3CH_2$ | $(CH_3)_3C$ | $CH_2$=$CBrCH_2$ |
| $CH_3CH_2$ | $(CH_3)_3C$ | $CH_2$=$CFCH_2$ |
| $CH_3CH_2$ | $(CH_3)_3C$ | $CHCl$=$CClCH_2$ |
| $CH_3CH_2$ | $(CH_3)_3C$ | $CHBr$=$CBrCH_2$ |
| $CH_3CH_2$ | $(CH_3)_3C$ | $CH_3CCl$=$CHCH_2$ |
| $CH_3CH_2$ | $(CH_3)_3C$ | $CF_3CCl$=$CHCH_2$ |
| $CH_3CH_2$ | $(CH_3)_3C$ | $CClH_2CH$=$CHCH_2$ |
| $CH_3CH_2$ | $(CH_3)_3C$ | $CBrH_2CH$=$CHCH_2$ |
| $CH_3CH_2$ | $(CH_3)_3C$ | $CF_2$=$CFCH_2$ |
| $CH_3CH_2$ | $(CH_3)_3C$ | $CH$≡$CCH_2$ |
| $CH_3CH_2$ | $(CH_3)_3C$ | $CH_3C$≡$CCH_2$ |
| $CH_3CH_2$ | $(CH_3)_3C$ | $CH_3CH_2C$≡$CCH_2$ |
| $CH_3CH_2$ | $(CH_3)_3C$ | $CH_3C$≡$CCH_2CH_2$ |
| $CH_3CH_2$ | $(CH_3)_3C$ | $CH$≡$C$—$(CH_3)CH$ |
| $CH_3CH_2$ | $(CH_3)_3C$ | $N$≡$CCH_2$ |
| $CH_3CH_2$ | $(CH_3)_3C$ | $N$≡$CCH_2CH_2$ |
| $CH_3CH_2$ | $(CH_3)_3C$ | $N$≡$CCH_2CH_2CH_2$ |
| $CH_3CH_2$ | $(CH_3)_3C$ | $N$≡$CCH_2CH_2CH_2CH_2$ |
| $CH_3CH_2$ | $(CH_3)_3C$ | H |
| $CH_3CH_2$ | $(CH_3)_3C$ | $C_6H_5$—$CH_2$ |
| $CH_3CH_2$ | $(CH_3)_3C$ | 2-F—$C_6H_4$—$CH_2$ |
| $CH_3CH_2$ | $(CH_3)_3C$ | 3-F—$C_6H_4$—$CH_2$ |
| $CH_3CH_2$ | $(CH_3)_3C$ | 4-F—$C_6H_4$—$CH_2$ |
| $CH_3CH_2$ | $(CH_3)_3C$ | 2-Cl—$C_6H_4$—$CH_2$ |

TABLE 1-continued (X represents $R^8O$—N)

| $R^1$ | $R^2$ | $R^8$ |
|---|---|---|
| $CH_3CH_2$ | $(CH_3)_3C$ | 3-Cl—$C_6H_4$—$CH_2$ |
| $CH_3CH_2$ | $(CH_3)_3C$ | 4-Cl—$C_6H_4$—$CH_2$ |
| $CH_3CH_2$ | $(CH_3)_3C$ | 2-Br—$C_6H_4$—$CH_2$ |
| $CH_3CH_2$ | $(CH_3)_3C$ | 3-Br—$C_6H_4$—$CH_2$ |
| $CH_3CH_2$ | $(CH_3)_3C$ | 4-Br—$C_6H_4$—$CH_2$ |
| $CH_3CH_2$ | $(CH_3)_3C$ | 4-I—$C_6H_4$—$CH_2$ |
| $CH_3CH_2$ | $(CH_3)_3C$ | 2-$CH_3$—$C_6H_4$—$CH_2$ |
| $CH_3CH_2$ | $(CH_3)_3C$ | 3-$CH_3$—$C_6H_4$—$CH_2$ |
| $CH_3CH_2$ | $(CH_3)_3C$ | 4-$CH_3$—$C_6H_4$—$CH_2$ |
| $CH_3CH_2$ | $(CH_3)_3C$ | 4-$CF_3$—$C_6H_4$—$CH_2$ |
| $CH_3CH_2$ | $(CH_3)_3C$ | 4-$CH_3CH_2$—$C_6H_4$—$CH_2$ |
| $CH_3CH_2$ | $(CH_3)_3C$ | 4-$(CH_3)_2CH$—$C_6H_4$—$CH_2$ |
| $CH_3CH_2$ | $(CH_3)_3C$ | 4-$CH_3CH_2CH_2$—$C_6H_4$—$CH_2$ |
| $CH_3CH_2$ | $(CH_3)_3C$ | 4-$(CH_3)_3C$—$C_6H_4$—$CH_2$ |
| $CH_3CH_2$ | $(CH_3)_3C$ | 2,4-$(CH_3)_2$—$C_6H_3$—$CH_2$ |
| $CH_3CH_2$ | $(CH_3)_3C$ | 2,4,6-$(CH_3)_3$—$C_6H_2$—$CH_2$ |
| $CH_3CH_2$ | $(CH_3)_3C$ | 2,4-$Cl_2$—$C_6H_3$—$CH_2$ |
| $CH_3CH_2$ | $(CH_3)_3C$ | 3,4-$Cl_2$—$C_6H_3$—$CH_2$ |
| $CH_3CH_2$ | $(CH_3)_3C$ | 2,5-$Cl_2$—$C_6H_3$—$CH_2$ |
| $CH_3CH_2$ | $(CH_3)_3C$ | 3,5-$Cl_2$—$C_6H_3$—$CH_2$ |
| $CH_3CH_2$ | $(CH_3)_3C$ | 2,6-$Cl_2$—$C_6H_3$—$CH_2$ |
| $CH_3CH_2$ | $(CH_3)_3C$ | 4-$CH_3O$—$C_6H_4$—$CH_2$ |
| $CH_3CH_2$ | $(CH_3)_3C$ | 4-$CF_3O$—$C_6H_4$—$CH_2$ |
| $CH_3CH_2$ | $(CH_3)_3C$ | 4-$CH_3CH_2O$—$C_6H_4$—$CH_2$ |
| $CH_3CH_2$ | $(CH_3)_3C$ | 4-$(CH_3)_2CHO$—$C_6H_4$—$CH_2$ |
| $CH_3CH_2$ | $(CH_3)_3C$ | 4-$(CH_3)_3CO$—$C_6H_4$—$CH_2$ |
| $CH_3CH_2$ | $(CH_3)_3C$ | 4-$CH_3OC(=O)$—$C_6H_4$—$CH_2$ |
| $CH_3CH_2$ | $(CH_3)_3C$ | 4-$CH_3CH_2OC(=O)$—$C_6H_4$—$CH_2$ |
| $CH_3CH_2$ | $(CH_3)_3C$ | 4-$CH_3CH_2CH_2OC(=O)$—$C_6H_4$—$CH_2$ |
| $CH_3CH_2$ | $(CH_3)_3C$ | 4-$(CH_3)_2CHOC(=O)$—$C_6H_4$—$CH_2$ |
| $CH_3CH_2$ | $(CH_3)_3C$ | 4-$(CH_3)_3COC(=O)$—$C_6H_4$—$CH_2$ |
| $CH_3CH_2$ | $(CH_3)_3C$ | $CH_2Cl$—$CH_2$ |
| $CH_3CH_2$ | $(CH_3)_3C$ | $CCl\equiv CCH_2$ |
| $CH_3CH_2$ | $(CH_3)_3C$ | $CBr\equiv CCH_2$ |
| $CF_3$ | $CH_3$ | $CH_3$ |
| $CF_3$ | $CH_3$ | $CH_3CH_2$ |
| $CF_3$ | $CH_3$ | $CH_3CH_2CH_2$ |
| $CF_3$ | $CH_3$ | $(CH_3)_2CH$ |
| $CF_3$ | $CH_3$ | $CH_3CH_2CH_2CH_2$ |
| $CF_3$ | $CH_3$ | $CH_3CH_2$—$(CH_3)CH$ |
| $CF_3$ | $CH_3$ | $(CH_3)_2CHCH_2$ |
| $CF_3$ | $CH_3$ | $(CH_3)_3C$ |
| $CF_3$ | $CH_3$ | $CH_3CH_2CH_2CH_2CH_2$ |
| $CF_3$ | $CH_3$ | $(CH_3)_2CHCH_2CH_2$ |
| $CF_3$ | $CH_3$ | $(CH_3)_3CCH_2$ |
| $CF_3$ | $CH_3$ | $CH_3CH_2CH_2$—$(CH_3)CH$ |
| $CF_3$ | $CH_3$ | $(CH_3)_2CH$—$(CH_3)CH$ |
| $CF_3$ | $CH_3$ | $CH_3CH_2CH_2CH_2CH_2CH_2$ |
| $CF_3$ | $CH_3$ | $CH_2F$ |
| $CF_3$ | $CH_3$ | $CH_2FCH_2$ |
| $CF_3$ | $CH_3$ | $CF_3CH_2$ |
| $CF_3$ | $CH_3$ | $CF_3CH_2CH_2$ |
| $CF_3$ | $CH_3$ | $CF_3CH_2CH_2CH_2$ |
| $CF_3$ | $CH_3$ | $CF_3CH_2CH_2CH_2CH_2$ |
| $CF_3$ | $CH_3$ | $CH_2ClCH_2CH_2$ |
| $CF_3$ | $CH_3$ | $CH_2BrCH_2CH_2$ |
| $CF_3$ | $CH_3$ | $CH_2ClCH_2CH_2CH_2$ |
| $CF_3$ | $CH_3$ | $CH_2BrCH_2CH_2CH_2$ |
| $CF_3$ | $CH_3$ | $CH_2ClCH_2CH_2CH_2CH_2$ |
| $CF_3$ | $CH_3$ | $CH_2BrCH_2CH_2CH_2CH_2$ |
| $CF_3$ | $CH_3$ | $CH_2=CHCH_2$ |
| $CF_3$ | $CH_3$ | $CH_2=C(CH_3)$—$CH_2$ |
| $CF_3$ | $CH_3$ | $(CH_3)_2C=CHCH_2$ |
| $CF_3$ | $CH_3$ | $CH_3CH=CHCH_2$ |
| $CF_3$ | $CH_3$ | $CH_2=CHCH_2CH_2$ |
| $CF_3$ | $CH_3$ | $CH_3CH_2CH=CHCH_2$ |
| $CF_3$ | $CH_3$ | $CH_3CH=CHCH_2CH_2$ |
| $CF_3$ | $CH_3$ | $CH_3CH_2CH_2CH=CHCH_2$ |
| $CF_3$ | $CH_3$ | $CH_3CH_2CH=CHCH_2CH_2$ |
| $CF_3$ | $CH_3$ | $CHCl=CHCH_2$ |
| $CF_3$ | $CH_3$ | $CCl_2=CHCH_2$ |
| $CF_3$ | $CH_3$ | $CHBr=CHCH_2$ |
| $CF_3$ | $CH_3$ | $CBr_2=CHCH_2$ |
| $CF_3$ | $CH_3$ | $CH_2=CClCH_2$ |
| $CF_3$ | $CH_3$ | $CH_2=CBrCH_2$ |
| $CF_3$ | $CH_3$ | $CH_2=CFCH_2$ |
| $CF_3$ | $CH_3$ | $CHCl=CClCH_2$ |
| $CF_3$ | $CH_3$ | $CHBr=CBrCH_2$ |
| $CF_3$ | $CH_3$ | $CH_3CCl=CHCH_2$ |
| $CF_3$ | $CH_3$ | $CF_3CCl=CHCH_2$ |
| $CF_3$ | $CH_3$ | $CClH_2$—$CH=CHCH_2$ |
| $CF_3$ | $CH_3$ | $CBrH_2$—$CH=CHCH_2$ |
| $CF_3$ | $CH_3$ | $CF_2=CFCH_2$ |
| $CF_3$ | $CH_3$ | $CH\equiv CCH_2$ |
| $CF_3$ | $CH_3$ | $CH_3C\equiv CCH_2$ |
| $CF_3$ | $CH_3$ | $CH_3CH_2C\equiv CCH_2$ |
| $CF_3$ | $CH_3$ | $CH_3C\equiv CCH_2CH_2$ |
| $CF_3$ | $CH_3$ | $CH\equiv C$—$(CH_3)CH$ |
| $CF_3$ | $CH_3$ | $N\equiv CCH_2$ |
| $CF_3$ | $CH_3$ | $N\equiv CCH_2CH_2$ |
| $CF_3$ | $CH_3$ | $N\equiv CCH_2CH_2CH_2$ |
| $CF_3$ | $CH_3$ | $N\equiv CCH_2CH_2CH_2CH_2$ |
| $CF_3$ | $CH_3$ | H |
| $CF_3$ | $CH_3$ | $C_6H_5$—$CH_2$ |
| $CF_3$ | $CH_3$ | 2-F—$C_6H_4$—$CH_2$ |
| $CF_3$ | $CH_3$ | 3-F—$C_6H_4$—$CH_2$ |
| $CF_3$ | $CH_3$ | 4-F—$C_6H_4$—$CH_2$ |
| $CF_3$ | $CH_3$ | 2-Cl—$C_6H_4$—$CH_2$ |
| $CF_3$ | $CH_3$ | 3-Cl—$C_6H_4$—$CH_2$ |
| $CF_3$ | $CH_3$ | 4-Cl—$C_6H_4$—$CH_2$ |
| $CF_3$ | $CH_3$ | 2-Br—$C_6H_4$—$CH_2$ |
| $CF_3$ | $CH_3$ | 3-Br—$C_6H_4$—$CH_2$ |
| $CF_3$ | $CH_3$ | 4-Br—$C_6H_4$—$CH_2$ |
| $CF_3$ | $CH_3$ | 4-I—$C_6H_4$—$CH_2$ |
| $CF_3$ | $CH_3$ | 2-$CH_3$—$C_6H_4$—$CH_2$ |
| $CF_3$ | $CH_3$ | 3-$CH_3$—$C_6H_4$—$CH_2$ |
| $CF_3$ | $CH_3$ | 4-$CH_3$—$C_6H_4$—$CH_2$ |
| $CF_3$ | $CH_3$ | 4-$CF_3$—$C_6H_4$—$CH_2$ |
| $CF_3$ | $CH_3$ | 4-$CH_3CH_2$—$C_6H_4$—$CH_2$ |
| $CF_3$ | $CH_3$ | 4-$(CH_3)_2CH$—$C_6H_4$—$CH_2$ |
| $CF_3$ | $CH_3$ | 4-$CH_3CH_2CH_2$—$C_6H_4$—$CH_2$ |
| $CF_3$ | $CH_3$ | 4-$(CH_3)_3C$—$C_6H_4$—$CH_2$ |
| $CF_3$ | $CH_3$ | 2,4-$(CH_3)_2$—$C_6H_3$—$CH_2$ |
| $CF_3$ | $CH_3$ | 2,4,6-$(CH_3)_3$—$C_6H_2$—$CH_2$ |
| $CF_3$ | $CH_3$ | 2,4-$Cl_2$—$C_6H_3$—$CH_2$ |
| $CF_3$ | $CH_3$ | 3,4-$Cl_2$—$C_6H_3$—$CH_2$ |
| $CF_3$ | $CH_3$ | 2,5-$Cl_2$—$C_6H_3$—$CH_2$ |
| $CF_3$ | $CH_3$ | 3,5-$Cl_2$—$C_6H_3$—$CH_2$ |
| $CF_3$ | $CH_3$ | 2,6-$Cl_2$—$C_6H_3$—$CH_2$ |
| $CF_3$ | $CH_3$ | 4-$CH_3O$—$C_6H_4$—$CH_2$ |
| $CF_3$ | $CH_3$ | 4-$CF_3O$—$C_6H_4$—$CH_2$ |
| $CF_3$ | $CH_3$ | 4-$CH_3CH_2O$—$C_6H_4$—$CH_2$ |
| $CF_3$ | $CH_3$ | 4-$(CH_3)_2CHO$—$C_6H_4$—$CH_2$ |
| $CF_3$ | $CH_3$ | 4-$(CH_3)_3CO$—$C_6H_4$—$CH_2$ |
| $CF_3$ | $CH_3$ | 4-$CH_3OC(=O)$—$C_6H_4$—$CH_2$ |
| $CF_3$ | $CH_3$ | 4-$CH_3CH_2OC(=O)$—$C_6H_4$—$CH_2$ |
| $CF_3$ | $CH_3$ | 4-$CH_3CH_2CH_2OC(=O)$—$C_6H_4$—$CH_2$ |
| $CF_3$ | $CH_3$ | 4-$(CH_3)_2CHOC(=O)$—$C_6H_4$—$CH_2$ |
| $CF_3$ | $CH_3$ | 4-$(CH_3)_3COC(=O)$—$C_6H_4$—$CH_2$ |
| $CF_3$ | $CH_3$ | $CH_2Cl$—$CH_2$ |
| $CF_3$ | $CH_3$ | $CCl\equiv CCH_2$ |
| $CF_3$ | $CH_3$ | $CBr\equiv CCH_2$ |
| $CF_3$ | $CH_3CH_2$ | $CH_3$ |
| $CF_3$ | $CH_3CH_2$ | $CH_3CH_2$ |
| $CF_3$ | $CH_3CH_2$ | $CH_3CH_2CH_2$ |
| $CF_3$ | $CH_3CH_2$ | $(CH_3)_2CH$ |
| $CF_3$ | $CH_3CH_2$ | $CH_3CH_2CH_2CH_2$ |
| $CF_3$ | $CH_3CH_2$ | $CH_3CH_2$—$(CH_3)CH$ |
| $CF_3$ | $CH_3CH_2$ | $(CH_3)_2CHCH_2$ |
| $CF_3$ | $CH_3CH_2$ | $(CH_3)_3C$ |
| $CF_3$ | $CH_3CH_2$ | $CH_3CH_2CH_2CH_2CH_2$ |
| $CF_3$ | $CH_3CH_2$ | $(CH_3)_2CHCH_2CH_2$ |
| $CF_3$ | $CH_3CH_2$ | $(CH_3)_3CCH_2$ |
| $CF_3$ | $CH_3CH_2$ | $CH_3CH_2CH_2$—$(CH_3)CH$ |
| $CF_3$ | $CH_3CH_2$ | $(CH_3)_2CH$—$(CH_3)CH$ |
| $CF_3$ | $CH_3CH_2$ | $CH_3CH_2CH_2CH_2CH_2CH_2$ |
| $CF_3$ | $CH_3CH_2$ | $CH_2F$ |
| $CF_3$ | $CH_3CH_2$ | $CH_2F$—$CH_2$ |
| $CF_3$ | $CH_3CH_2$ | $CF_3CH_2$ |
| $CF_3$ | $CH_3CH_2$ | $CF_3CH_2CH_2$ |

TABLE 1-continued (X represents R⁸O—N)

| R¹ | R² | R⁸ |
|---|---|---|
| CF₃ | CH₃CH₂ | CF₃CH₂CH₂CH₂ |
| CF₃ | CH₃CH₂ | CF₃CH₂CH₂CH₂CH₂ |
| CF₃ | CH₃CH₂ | CH₂Cl—CH₂CH₂ |
| CF₃ | CH₃CH₂ | CH₂Br—CH₂CH₂ |
| CF₃ | CH₃CH₂ | CH₂Cl—CH₂CH₂CH₂ |
| CF₃ | CH₃CH₂ | CH₂Br—CH₂CH₂CH₂ |
| CF₃ | CH₃CH₂ | CH₂Cl—CH₂CH₂CH₂CH₂ |
| CF₃ | CH₃CH₂ | CH₂Br—CH₂CH₂CH₂CH₂ |
| CF₃ | CH₃CH₂ | CH₂=CHCH₂ |
| CF₃ | CH₃CH₂ | CH₂=C(CH₃)—CH₂ |
| CF₃ | CH₃CH₂ | (CH₃)₂C=CHCH₂ |
| CF₃ | CH₃CH₂ | CH₃CH=CHCH₂ |
| CF₃ | CH₃CH₂ | CH₂=CHCH₂CH₂ |
| CF₃ | CH₃CH₂ | CH₃CH₂CH=CHCH₂ |
| CF₃ | CH₃CH₂ | CH₃CH=CHCH₂CH₂ |
| CF₃ | CH₃CH₂ | CH₃CH₂CH₂CH=CHCH₂ |
| CF₃ | CH₃CH₂ | CH₃CH₂CH=CHCH₂CH₂ |
| CF₃ | CH₃CH₂ | CHCl=CHCH₂ |
| CF₃ | CH₃CH₂ | CCl₂=CHCH₂ |
| CF₃ | CH₃CH₂ | CHBr=CHCH₂ |
| CF₃ | CH₃CH₂ | CBr₂=CHCH₂ |
| CF₃ | CH₃CH₂ | CH₂=CClCH₂ |
| CF₃ | CH₃CH₂ | CH₂=CBrCH₂ |
| CF₃ | CH₃CH₂ | CH₂=CFCH₂ |
| CF₃ | CH₃CH₂ | CHCl=CClCH₂ |
| CF₃ | CH₃CH₂ | CHBr=CBrCH₂ |
| CF₃ | CH₃CH₂ | CH₃CCl=CHCH₂ |
| CF₃ | CH₃CH₂ | CF₃CCl=CHCH₂ |
| CF₃ | CH₃CH₂ | CClH₂—CH=CHCH₂ |
| CF₃ | CH₃CH₂ | CBrH₂—CH=CHCH₂ |
| CF₃ | CH₃CH₂ | CF₂=CFCH₂ |
| CF₃ | CH₃CH₂ | CH≡CCH₂ |
| CF₃ | CH₃CH₂ | CH₃C≡CCH₂ |
| CF₃ | CH₃CH₂ | CH₃CH₂C≡CCH₂ |
| CF₃ | CH₃CH₂ | CH₃C≡CCH₂CH₂ |
| CF₃ | CH₃CH₂ | CH≡C—(CH₃)CH |
| CF₃ | CH₃CH₂ | N≡CCH₂ |
| CF₃ | CH₃CH₂ | N≡CCH₂CH₂ |
| CF₃ | CH₃CH₂ | N≡CCH₂CH₂CH₂ |
| CF₃ | CH₃CH₂ | N≡CCH₂CH₂CH₂CH₂ |
| CF₃ | CH₃CH₂ | H |
| CF₃ | CH₃CH₂ | C₆H₅—CH₂ |
| CF₃ | CH₃CH₂ | 2-F—C₆H₄—CH₂ |
| CF₃ | CH₃CH₂ | 3-F—C₆H₄—CH₂ |
| CF₃ | CH₃CH₂ | 4-F—C₆H₄—CH₂ |
| CF₃ | CH₃CH₂ | 2-Cl—C₆H₄—CH₂ |
| CF₃ | CH₃CH₂ | 3-Cl—C₆H₄—CH₂ |
| CF₃ | CH₃CH₂ | 4-Cl—C₆H₄—CH₂ |
| CF₃ | CH₃CH₂ | 2-Br—C₆H₄—CH₂ |
| CF₃ | CH₃CH₂ | 3-Br—C₆H₄—CH₂ |
| CF₃ | CH₃CH₂ | 4-Br—C₆H₄—CH₂ |
| CF₃ | CH₃CH₂ | 4-I—C₆H₄—CH₂ |
| CF₃ | CH₃CH₂ | 2-CH₃—C₆H₄—CH₂ |
| CF₃ | CH₃CH₂ | 3-CH₃—C₆H₄—CH₂ |
| CF₃ | CH₃CH₂ | 4-CH₃—C₆H₄—CH₂ |
| CF₃ | CH₃CH₂ | 4-CF₃—C₆H₄—CH₂ |
| CF₃ | CH₃CH₂ | 4-CH₃CH₂—C₆H₄—CH₂ |
| CF₃ | CH₃CH₂ | 4-(CH₃)₂CH—C₆H₄—CH₂ |
| CF₃ | CH₃CH₂ | 4-CH₃CH₂CH₂—C₆H₄—CH₂ |
| CF₃ | CH₃CH₂ | 4-(CH₃)₃C—C₆H₄—CH₂ |
| CF₃ | CH₃CH₂ | 2,4-(CH₃)₂—C₆H₃—CH₂ |
| CF₃ | CH₃CH₂ | 2,4,6-(CH₃)₃—C₆H₂—CH₂ |
| CF₃ | CH₃CH₂ | 2,4-Cl₂—C₆H₃—CH₂ |
| CF₃ | CH₃CH₂ | 3,4-Cl₂—C₆H₃—CH₂ |
| CF₃ | CH₃CH₂ | 2,5-Cl₂—C₆H₃—CH₂ |
| CF₃ | CH₃CH₂ | 3,5-Cl₂—C₆H₃—CH₂ |
| CF₃ | CH₃CH₂ | 2,6-Cl₂—C₆H₃—CH₂ |
| CF₃ | CH₃CH₂ | 4-CH₃O—C₆H₄—CH₂ |
| CF₃ | CH₃CH₂ | 4-CF₃O—C₆H₄—CH₂ |
| CF₃ | CH₃CH₂ | 4-CH₃CH₂O—C₆H₄—CH₂ |
| CF₃ | CH₃CH₂ | 4-(CH₃)₂CHO—C₆H₄—CH₂ |
| CF₃ | CH₃CH₂ | 4-(CH₃)₃CO—C₆H₄—CH₂ |
| CF₃ | CH₃CH₂ | 4-CH₃OC(=O)—C₆H₄—CH₂ |
| CF₃ | CH₃CH₂ | 4-CH₃CH₂OC(=O)—C₆H₄—CH₂ |
| CF₃ | CH₃CH₂ | 4-CH₃CH₂CH₂OC(=O)—C₆H₄—CH₂ |
| CF₃ | CH₃CH₂ | 4-(CH₃)₂CHOC(=O)—C₆H₄—CH₂ |
| CF₃ | CH₃CH₂ | 4-(CH₃)₃COC(=O)—C₆H₄—CH₂ |
| CF₃ | CH₃CH₂ | CH₂Cl—CH₂ |
| CF₃ | CH₃CH₂ | CCl≡CCH₂ |
| CF₃ | CH₃CH₂ | CBr≡CCH₂ |
| CF₃ | (CH₃)₂CH | CH₃ |
| CF₃ | (CH₃)₂CH | CH₃CH₂ |
| CF₃ | (CH₃)₂CH | CH₃CH₂CH₂ |
| CF₃ | (CH₃)₂CH | (CH₃)₂CH |
| CF₃ | (CH₃)₂CH | CH₃CH₂CH₂CH₂ |
| CF₃ | (CH₃)₂CH | CH₃CH₂—(CH₃)CH |
| CF₃ | (CH₃)₂CH | (CH₃)₂CHCH₂ |
| CF₃ | (CH₃)₂CH | (CH₃)₃C |
| CF₃ | (CH₃)₂CH | CH₃CH₂CH₂CH₂CH₂ |
| CF₃ | (CH₃)₂CH | (CH₃)₂CHCH₂CH₂ |
| CF₃ | (CH₃)₂CH | (CH₃)₃CCH₂ |
| CF₃ | (CH₃)₂CH | CH₃CH₂CH₂—(CH₃)CH |
| CF₃ | (CH₃)₂CH | (CH₃)₂CH—(CH₃)CH |
| CF₃ | (CH₃)₂CH | CH₃CH₂CH₂CH₂CH₂CH₂ |
| CF₃ | (CH₃)₂CH | CH₂F |
| CF₃ | (CH₃)₂CH | CH₂F—CH₂ |
| CF₃ | (CH₃)₂CH | CF₃CH₂ |
| CF₃ | (CH₃)₂CH | CF₃CH₂CH₂ |
| CF₃ | (CH₃)₂CH | CF₃CH₂CH₂CH₂ |
| CF₃ | (CH₃)₂CH | CF₃CH₂CH₂CH₂CH₂ |
| CF₃ | (CH₃)₂CH | CH₂Cl—CH₂CH₂ |
| CF₃ | (CH₃)₂CH | CH₂Br—CH₂CH₂ |
| CF₃ | (CH₃)₂CH | CH₂Cl—CH₂CH₂CH₂ |
| CF₃ | (CH₃)₂CH | CH₂Br—CH₂CH₂CH₂ |
| CF₃ | (CH₃)₂CH | CH₂Cl—CH₂CH₂CH₂CH₂ |
| CF₃ | (CH₃)₂CH | CH₂Br—CH₂CH₂CH₂CH₂ |
| CF₃ | (CH₃)₂CH | CH₂=CHCH₂ |
| CF₃ | (CH₃)₂CH | CH₂=C(CH₃)CH₂ |
| CF₃ | (CH₃)₂CH | (CH₃)₂C=CHCH₂ |
| CF₃ | (CH₃)₂CH | CH₃CH=CHCH₂ |
| CF₃ | (CH₃)₂CH | CH₂=CHCH₂CH₂ |
| CF₃ | (CH₃)₂CH | CH₃CH₂CH=CHCH₂ |
| CF₃ | (CH₃)₂CH | CH₃CH=CHCH₂CH₂ |
| CF₃ | (CH₃)₂CH | CH₃CH₂CH₂CH=CHCH₂ |
| CF₃ | (CH₃)₂CH | CH₃CH₂CH=CHCH₂CH₂ |
| CF₃ | (CH₃)₂CH | CHCl=CHCH₂ |
| CF₃ | (CH₃)₂CH | CCl₂=CHCH₂ |
| CF₃ | (CH₃)₂CH | CHBr=CHCH₂ |
| CF₃ | (CH₃)₂CH | CBr₂=CHCH₂ |
| CF₃ | (CH₃)₂CH | CH₂=CClCH₂ |
| CF₃ | (CH₃)₂CH | CH₂=CBrCH₂ |
| CF₃ | (CH₃)₂CH | CH₂=CFCH₂ |
| CF₃ | (CH₃)₂CH | CHCl=CClCH₂ |
| CF₃ | (CH₃)₂CH | CHBr=CBrCH₂ |
| CF₃ | (CH₃)₂CH | CH₃CCl=CHCH₂ |
| CF₃ | (CH₃)₂CH | CF₃CCl=CHCH₂ |
| CF₃ | (CH₃)₂CH | CClH₂—CH=CHCH₂ |
| CF₃ | (CH₃)₂CH | CBrH₂—CH=CHCH₂ |
| CF₃ | (CH₃)₂CH | CF₂=CFCH₂ |
| CF₃ | (CH₃)₂CH | CH≡CCH₂ |
| CF₃ | (CH₃)₂CH | CH₃C≡CCH₂ |
| CF₃ | (CH₃)₂CH | CH₃CH₂C≡CCH₂ |
| CF₃ | (CH₃)₂CH | CH₃C≡CCH₂CH₂ |
| CF₃ | (CH₃)₂CH | CH≡C—(CH₃)CH |
| CF₃ | (CH₃)₂CH | N≡CCH₂ |
| CF₃ | (CH₃)₂CH | N≡CCH₂CH₂ |
| CF₃ | (CH₃)₂CH | N≡CCH₂CH₂CH₂ |
| CF₃ | (CH₃)₂CH | N≡CCH₂CH₂CH₂CH₂ |
| CF₃ | (CH₃)₂CH | H |
| CF₃ | (CH₃)₂CH | C₆H₅—CH₂ |
| CF₃ | (CH₃)₂CH | 2-F—C₆H₄—CH₂ |
| CF₃ | (CH₃)₂CH | 3-F—C₆H₄—CH₂ |
| CF₃ | (CH₃)₂CH | 4-F—C₆H₄—CH₂ |
| CF₃ | (CH₃)₂CH | 2-Cl—C₆H₄—CH₂ |
| CF₃ | (CH₃)₂CH | 3-Cl—C₆H₄—CH₂ |
| CF₃ | (CH₃)₂CH | 4-Cl—C₆H₄—CH₂ |
| CF₃ | (CH₃)₂CH | 2-Br—C₆H₄—CH₂ |
| CF₃ | (CH₃)₂CH | 3-Br—C₆H₄—CH₂ |
| CF₃ | (CH₃)₂CH | 4-Br—C₆H₄—CH₂ |
| CF₃ | (CH₃)₂CH | 4-I—C₆H₄—CH₂ |

TABLE 1-continued (X represents $R^8O-N$)

| $R^1$ | $R^2$ | $R^8$ |
|---|---|---|
| $CF_3$ | $(CH_3)_2CH$ | 2-$CH_3$—$C_6H_4$—$CH_2$ |
| $CF_3$ | $(CH_3)_2CH$ | 3-$CH_3$—$C_6H_4$—$CH_2$ |
| $CF_3$ | $(CH_3)_2CH$ | 4-$CH_3$—$C_6H_4$—$CH_2$ |
| $CF_3$ | $(CH_3)_2CH$ | 4-$CF_3$—$C_6H_4$—$CH_2$ |
| $CF_3$ | $(CH_3)_2CH$ | 4-$CH_3CH_2$—$C_6H_4$—$CH_2$ |
| $CF_3$ | $(CH_3)_2CH$ | 4-$(CH_3)_2CH$—$C_6H_4$—$CH_2$ |
| $CF_3$ | $(CH_3)_2CH$ | 4-$CH_3CH_2CH_2$—$C_6H_4$—$CH_2$ |
| $CF_3$ | $(CH_3)_2CH$ | 4-$(CH_3)_3C$—$C_6H_4$—$CH_2$ |
| $CF_3$ | $(CH_3)_2CH$ | 2,4-$(CH_3)_2$—$C_6H_3$—$CH_2$ |
| $CF_3$ | $(CH_3)_2CH$ | 2,4,6-$(CH_3)_3$—$C_6H_2$—$CH_2$ |
| $CF_3$ | $(CH_3)_2CH$ | 2,4-$Cl_2$—$C_6H_3$—$CH_2$ |
| $CF_3$ | $(CH_3)_2CH$ | 3,4-$Cl_2$—$C_6H_3$—$CH_2$ |
| $CF_3$ | $(CH_3)_2CH$ | 2,5-$Cl_2$—$C_6H_3$—$CH_2$ |
| $CF_3$ | $(CH_3)_2CH$ | 3,5-$Cl_2$—$C_6H_3$—$CH_2$ |
| $CF_3$ | $(CH_3)_2CH$ | 2,6-$Cl_2$—$C_6H_3$—$CH_2$ |
| $CF_3$ | $(CH_3)_2CH$ | 4-$CH_3O$—$C_6H_4$—$CH_2$ |
| $CF_3$ | $(CH_3)_2CH$ | 4-$CF_3O$—$C_6H_4$—$CH_2$ |
| $CF_3$ | $(CH_3)_2CH$ | 4-$CH_3CH_2O$—$C_6H_4$—$CH_2$ |
| $CF_3$ | $(CH_3)_2CH$ | 4-$(CH_3)_2CHO$—$C_6H_4$—$CH_2$ |
| $CF_3$ | $(CH_3)_2CH$ | 4-$(CH_3)_3CO$—$C_6H_4$—$CH_2$ |
| $CF_3$ | $(CH_3)_2CH$ | 4-$CH_3OC(=O)$—$C_6H_4$—$CH_2$ |
| $CF_3$ | $(CH_3)_2CH$ | 4-$CH_3CH_2OC(=O)$—$C_6H_4$—$CH_2$ |
| $CF_3$ | $(CH_3)_2CH$ | 4-$CH_3CH_2CH_2OC(=O)$—$C_6H_4$—$CH_2$ |
| $CF_3$ | $(CH_3)_2CH$ | 4-$(CH_3)_2CHOC(=O)$—$C_6H_4$—$CH_2$ |
| $CF_3$ | $(CH_3)_2CH$ | 4-$(CH_3)_3COC(=O)$—$C_6H_4$—$CH_2$ |
| $CF_3$ | $(CH_3)_2CH$ | $CH_2Cl$—$CH_2$ |
| $CF_3$ | $(CH_3)_2CH$ | $CCl=CCH_2$ |
| $CF_3$ | $(CH_3)_2CH$ | $CBr=CCH_2$ |
| $CF_3$ | $(CH_3)_3C$ | $CH_3$ |
| $CF_3$ | $(CH_3)_3C$ | $CH_3CH_2$ |
| $CF_3$ | $(CH_3)_3C$ | $CH_3CH_2CH_2$ |
| $CF_3$ | $(CH_3)_3C$ | $(CH_3)_2CH$ |
| $CF_3$ | $(CH_3)_3C$ | $CH_3CH_2CH_2CH_2$ |
| $CF_3$ | $(CH_3)_3C$ | $CH_3CH_2$—$(CH_3)CH$ |
| $CF_3$ | $(CH_3)_3C$ | $(CH_3)_2CHCH_2$ |
| $CF_3$ | $(CH_3)_3C$ | $(CH_3)_3C$ |
| $CF_3$ | $(CH_3)_3C$ | $CH_3CH_2CH_2CH_2CH_2$ |
| $CF_3$ | $(CH_3)_3C$ | $(CH_3)_2CHCH_2CH_2$ |
| $CF_3$ | $(CH_3)_3C$ | $(CH_3)_3CCH_2$ |
| $CF_3$ | $(CH_3)_3C$ | $CH_3CH_2CH_2$—$(CH_3)CH$ |
| $CF_3$ | $(CH_3)_3C$ | $(CH_3)_2CHCH_2$—$(CH_3)CH$ |
| $CF_3$ | $(CH_3)_3C$ | $CH_3CH_2CH_2CH_2CH_2CH_2$ |
| $CF_3$ | $(CH_3)_3C$ | $CH_2F$ |
| $CF_3$ | $(CH_3)_3C$ | $CH_2F$—$CH_2$ |
| $CF_3$ | $(CH_3)_3C$ | $CF_3CH_2$ |
| $CF_3$ | $(CH_3)_3C$ | $CF_3CH_2CH_2$ |
| $CF_3$ | $(CH_3)_3C$ | $CF_3CH_2CH_2CH_2$ |
| $CF_3$ | $(CH_3)_3C$ | $CF_3CH_2CH_2CH_2CH_2$ |
| $CF_3$ | $(CH_3)_3C$ | $CH_2Cl$—$CH_2CH_2$ |
| $CF_3$ | $(CH_3)_3C$ | $CH_2Br$—$CH_2CH_2$ |
| $CF_3$ | $(CH_3)_3C$ | $CH_2Cl$—$CH_2CH_2CH_2$ |
| $CF_3$ | $(CH_3)_3C$ | $CH_2Br$—$CH_2CH_2CH_2$ |
| $CF_3$ | $(CH_3)_3C$ | $CH_2Cl$—$CH_2CH_2CH_2CH_2$ |
| $CF_3$ | $(CH_3)_3C$ | $CH_2BrCH_2CH_2CH_2CH_2$ |
| $CF_3$ | $(CH_3)_3C$ | $CH_2=CHCH_2$ |
| $CF_3$ | $(CH_3)_3C$ | $CH_2=C(CH_3)$—$CH_2$ |
| $CF_3$ | $(CH_3)_3C$ | $(CH_3)_2C=CHCH_2$ |
| $CF_3$ | $(CH_3)_3C$ | $CH_3CH=CHCH_2$ |
| $CF_3$ | $(CH_3)_3C$ | $CH_2=CHCH_2CH_2$ |
| $CF_3$ | $(CH_3)_3C$ | $CH_3CH_2CH=CHCH_2$ |
| $CF_3$ | $(CH_3)_3C$ | $CH_3CH=CHCH_2CH_2$ |
| $CF_3$ | $(CH_3)_3C$ | $CH_3CH_2CH_2CH=CHCH_2$ |
| $CF_3$ | $(CH_3)_3C$ | $CH_3CH_2CH=CHCH_2CH_2$ |
| $CF_3$ | $(CH_3)_3C$ | $CHCl=CHCH_2$ |
| $CF_3$ | $(CH_3)_3C$ | $CCl_2=CHCH_2$ |
| $CF_3$ | $(CH_3)_3C$ | $CHBr=CHCH_2$ |
| $CF_3$ | $(CH_3)_3C$ | $CBr_2=CHCH_2$ |
| $CF_3$ | $(CH_3)_3C$ | $CH_2=CClCH_2$ |
| $CF_3$ | $(CH_3)_3C$ | $CH_2=CBrCH_2$ |
| $CF_3$ | $(CH_3)_3C$ | $CH_2=CFCH_2$ |
| $CF_3$ | $(CH_3)_3C$ | $CHCl=CClCH_2$ |
| $CF_3$ | $(CH_3)_3C$ | $CHBr=CBrCH_2$ |
| $CF_3$ | $(CH_3)_3C$ | $CH_3CCl=CHCH_2$ |
| $CF_3$ | $(CH_3)_3C$ | $CF_3CCl=CHCH_2$ |
| $CF_3$ | $(CH_3)_3C$ | $CClH_2CH=CHCH_2$ |
| $CF_3$ | $(CH_3)_3C$ | $CBrH_2CH=CHCH_2$ |
| $CF_3$ | $(CH_3)_3C$ | $CF_2=CFCH_2$ |
| $CF_3$ | $(CH_3)_3C$ | $CH=CCH_2$ |
| $CF_3$ | $(CH_3)_3C$ | $CH_3C=CCH_2$ |
| $CF_3$ | $(CH_3)_3C$ | $CH_3CH_2C=CCH_2$ |
| $CF_3$ | $(CH_3)_3C$ | $CH_3C=CCH_2CH_2$ |
| $CF_3$ | $(CH_3)_3C$ | $CH=C$—$(CH_3)CH$ |
| $CF_3$ | $(CH_3)_3C$ | $N=CCH_2$ |
| $CF_3$ | $(CH_3)_3C$ | $N=CCH_2CH_2$ |
| $CF_3$ | $(CH_3)_3C$ | $N=CCH_2CH_2CH_2$ |
| $CF_3$ | $(CH_3)_3C$ | $N=CCH_2CH_2CH_2CH_2$ |
| $CF_3$ | $(CH_3)_3C$ | H |
| $CF_3$ | $(CH_3)_3C$ | $C_6H_5$—$CH_2$ |
| $CF_3$ | $(CH_3)_3C$ | 2-F—$C_6H_4$—$CH_2$ |
| $CF_3$ | $(CH_3)_3C$ | 3-F—$C_6H_4$—$CH_2$ |
| $CF_3$ | $(CH_3)_3C$ | 4-F—$C_6H_4$—$CH_2$ |
| $CF_3$ | $(CH_3)_3C$ | 2-Cl—$C_6H_4$—$CH_2$ |
| $CF_3$ | $(CH_3)_3C$ | 3-Cl—$C_6H_4$—$CH_2$ |
| $CF_3$ | $(CH_3)_3C$ | 4-Cl—$C_6H_4$—$CH_2$ |
| $CF_3$ | $(CH_3)_3C$ | 2-Br—$C_6H_4$—$CH_2$ |
| $CF_3$ | $(CH_3)_3C$ | 3-Br—$C_6H_4$—$CH_2$ |
| $CF_3$ | $(CH_3)_3C$ | 4-Br—$C_6H_4$—$CH_2$ |
| $CF_3$ | $(CH_3)_3C$ | 4-I—$C_6H_4$—$CH_2$ |
| $CF_3$ | $(CH_3)_3C$ | 2-$CH_3$—$C_6H_4$—$CH_2$ |
| $CF_3$ | $(CH_3)_3C$ | 3-$CH_3$—$C_6H_4$—$CH_2$ |
| $CF_3$ | $(CH_3)_3C$ | 4-$CH_3$—$C_6H_4$—$CH_2$ |
| $CF_3$ | $(CH_3)_3C$ | 4-$CF_3$—$C_6H_4$—$CH_2$ |
| $CF_3$ | $(CH_3)_3C$ | 4-$CH_3CH_2$—$C_6H_4$—$CH_2$ |
| $CF_3$ | $(CH_3)_3C$ | 4-$(CH_3)_2CH$—$C_6H_4$—$CH_2$ |
| $CF_3$ | $(CH_3)_3C$ | 4-$CH_3CH_2CH_2$—$C_6H_4$—$CH_2$ |
| $CF_3$ | $(CH_3)_3C$ | 4-$(CH_3)_3C$—$C_6H_4$—$CH_2$ |
| $CF_3$ | $(CH_3)_3C$ | 2,4-$(CH_3)_2$—$C_6H_3$—$CH_2$ |
| $CF_3$ | $(CH_3)_3C$ | 2,4,6-$(CH_3)_3$—$C_6H_2$—$CH_2$ |
| $CF_3$ | $(CH_3)_3C$ | 2,4-$Cl_2$—$C_6H_3$—$CH_2$ |
| $CF_3$ | $(CH_3)_3C$ | 3,4-$Cl_2$—$C_6H_3$—$CH_2$ |
| $CF_3$ | $(CH_3)_3C$ | 2,5-$Cl_2$—$C_6H_3$—$CH_2$ |
| $CF_3$ | $(CH_3)_3C$ | 3,5-$Cl_2$—$C_6H_3$—$CH_2$ |
| $CF_3$ | $(CH_3)_3C$ | 2,6-$Cl_2$—$C_6H_3$—$CH_2$ |
| $CF_3$ | $(CH_3)_3C$ | 4-$CH_3O$—$C_6H_4$—$CH_2$ |
| $CF_3$ | $(CH_3)_3C$ | 4-$CF_3O$—$C_6H_4$—$CH_2$ |
| $CF_3$ | $(CH_3)_3C$ | 4-$CH_3CH_2O$—$C_6H_4$—$CH_2$ |
| $CF_3$ | $(CH_3)_3C$ | 4-$(CH_3)_2CHO$—$C_6H_4$—$CH_2$ |
| $CF_3$ | $(CH_3)_3C$ | 4-$(CH_3)_3CO$—$C_6H_4$—$CH_2$ |
| $CF_3$ | $(CH_3)_3C$ | 4-$CH_3OC(=O)$—$C_6H_4$—$CH_2$ |
| $CF_3$ | $(CH_3)_3C$ | 4-$CH_3CH_2OC(=O)$—$C_6H_4$—$CH_2$ |
| $CF_3$ | $(CH_3)_3C$ | 4-$CH_3CH_2CH_2OC(=O)$—$C_6H_4$—$CH_2$ |
| $CF_3$ | $(CH_3)_3C$ | 4-$(CH_3)_2CHOC(=O)$—$C_6H_4$—$CH_2$ |
| $CF_3$ | $(CH_3)_3C$ | 4-$(CH_3)_3COC(=O)$—$C_6H_4$—$CH_2$ |
| $CF_3$ | $(CH_3)_3C$ | $CH_2Cl$—$CH_2$ |
| $CF_3$ | $(CH_3)_3C$ | $CCl=CCH_2$ |
| $CF_3$ | $(CH_3)_3C$ | $CBr=CCH_2$ |
| $(CH_3)_2CH$ | $CH_3$ | H |
| $(CH_3)_2CH$ | $CH_3$ | $CH_3$ |
| $(CH_3)_2CH$ | $CH_3$ | $CH_3CH_2$ |
| $(CH_3)_2CH$ | $CH_3$ | $CH_3CH_2CH_2$ |
| $(CH_3)_2CH$ | $CH_3$ | $CH_2F$ |
| $(CH_3)_2CH$ | $CH_3$ | $CF_3CH_2$ |
| $(CH_3)_2CH$ | $CH_3$ | $CF_3CH_2CH_2$ |
| $(CH_3)_2CH$ | $CH_3$ | $CH_2ClCH_2$ |
| $(CH_3)_2CH$ | $CH_3$ | $CH_2=CHCH_2$ |
| $(CH_3)_2CH$ | $CH_3$ | $CH=CCH_2$ |
| $(CH_3)_2CH$ | $CH_3$ | $CH_3C=CCH_2$ |
| $(CH_3)_2CH$ | $CH_3$ | $N=CCH_2$ |
| $(CH_3)_3C$ | $CH_3$ | H |
| $(CH_3)_3C$ | $CH_3$ | $CH_3$ |
| $(CH_3)_3C$ | $CH_3$ | $CH_3CH_2$ |
| $(CH_3)_3C$ | $CH_3$ | $CH_3CH_2CH_2$ |
| $(CH_3)_3C$ | $CH_3$ | $CH_2F$ |
| $(CH_3)_3C$ | $CH_3$ | $CF_3CH_2$ |
| $(CH_3)_3C$ | $CH_3$ | $CF_3CH_2CH_2$ |
| $(CH_3)_3C$ | $CH_3$ | $CH_2Cl$—$CH_2$ |
| $(CH_3)_3C$ | $CH_3$ | $CH_2=CHCH_2$ |
| $(CH_3)_3C$ | $CH_3$ | $CH=CCH_2$ |

TABLE 1-continued (X represents R⁸O—N)

| R¹ | R² | R⁸ |
|---|---|---|
| $(CH_3)_3C$ | $CH_3$ | $CH_3C\equiv CCH_2$ |
| $(CH_3)_3C$ | $CH_3$ | $N\equiv CCH_2$ |

TABLE 2

(X represents an oxygen atom)

| R¹ | R² |
|---|---|
| $CH_3$ | $CH_3$ |
| $CH_3$ | $CH_3CH_2$ |
| $CH_3$ | $(CH_3)_2CH$ |
| $CH_3$ | $(CH_3)_3C$ |
| $CH_3CH_2$ | $CH_3$ |
| $CH_3CH_2$ | $CH_3CH_2$ |
| $CH_3CH_2$ | $(CH_3)_2CH$ |
| $CH_3CH_2$ | $(CH_3)_3C$ |
| $CH_3CH_2$ | $CH_3$ |
| $CH_3CH_2$ | $CH_3CH_2$ |
| $CH_3CH_2$ | $(CH_3)_2CH$ |
| $CH_3CH_2$ | $(CH_3)_3C$ |
| $(CH_3)_3C$ | $CH_3$ |
| $(CH_3)_3C$ | $CH_3CH_2$ |
| $(CH_3)_3C$ | $(CH_3)_2CH$ |
| $(CH_3)_3C$ | $(CH_3)_3C$ |
| $(CH_3)_2CH$ | $CH_3$ |
| $(CH_3)_2CH$ | $CH_3CH_2$ |
| $(CH_3)_2CH$ | $(CH_3)_2CH$ |
| $(CH_3)_2CH$ | $(CH_3)_3C$ |
| $CF_3$ | $CH_3$ |
| $CF_3$ | $CH_3CH_2$ |
| $CF_3$ | $(CH_3)_2CH$ |
| $CF_3$ | $(CH_3)_3C$ |

The noxious arthropods against which the compound of the present invention has activity may include insect pests and acarine pests, and concretely described below:

Hemiptera:
  Delphacidae such as *Laodelphax striatellus, Nilaparvata lugens, Sogatella furcifera* and the like,
  Deltocephalidae such as *Nephotettix cincticeps, Nephotettix virescens* and the like,
  Aphididae such as *Aphis gossypii, Myzus persicae* and the like,
  Pentatomidae such as *Nezara antennata, Riptortus clavetus* and the like,
  Aleyrodidae such as *Trialeurodes vaporariorum, Bemisia argentifolii* and the like,
  Coccidae such as *Aonidiella aurantii, Comstockaspis perniciosa, Unaspis citri, Ceroplastes rubens, Icerya purchasi* and the like,
  Tingidae,
  Psyllidae, and the like;

Lepidoptera:
  Pyralidae such as *Chilo suppressalis, Cnaphalocrocis medinalis, Notarcha derogata, Plodia interpunctella* and the like,
  Noctuidae such as *Spodoptera litura, Pseudaletia separata, Thoricoplusia* spp., *Heliothis* spp., *Helicoverpa* spp. and the like,
  Pieridae such as *Pieris rapae* and the like,
  Tortricidae such as *Adoxophyes* spp., *Grapholita molesta, Cydia pomonella* and the like,
  Carposinidae such as *Carposina niponensis* and the like,
  Lyonetiidae such as *Lyonetia* spp. and the like,
  Lymantriidae such as *Lymantria* spp., *Euproctis* spp., and the like,
  Yponomeutidae such as *Plutella xylostella* and the like,
  Gelechiidae such as *Pectinophora gossypiella* and the like,
  Arctiidae such as *Hyphantria cunea* and the like,
  Tineidae such as *Tinea translucens, Tineola bisselliella* and the like;

Diptera:
  Calicidae such as *Culex pipiens pallens, Culex tritaeniorhynchus, Culex quinquefasciatus* and the like,
  *Aedes* spp. such as *Aedes aegypti, Aedes albopictus* and the like,
  Anopheles such as *Anopheles sinensis* and the like,
  Chironomidae,
  Muscidae such as *Musca domestica, Muscina stabulans* and the like,
  Calliphoridae,
  Sarcophagidae,
  Fanniidae,
  Anthomyiidae such as *Delia platura, Delia antiqua* and the like,
  Tephritidae,
  Drosophilidae,
  Psychodidae,
  Tabanidae,
  Simuliidae,
  Stomoxyidae,
  Agromyzidae, and the like;

Coleoptera:
  *Diabrotica* spp. such as *Diabrotica virgifera virgifera, Diabrotica undecimpunctata howardi* and the like,
  Scarabaeidae such as *Anomala cuprea, Anomala rufocuprea* and the like,
  Curculionidae such as *Sitophilus zeamais, Lissorhoptrus oryzophilus, Callosobruchuys chienensis* and the like,
  Tenebrionidae such as *Tenebrio molitor, Tribolium castaneum* and the like,
  Chrysomelidae such as *Aulacophora femoralis, Phyllotreta striolata, Leptinotarsa decemlineata* and the like,
  Anobiidae,
  *Epilachna* spp. such as *Epilachna vigintioctopunctata* and the like,
  Lyctidae,
  Bostrychidae,
  Cerambycidae,
  *Paederus fuscipes;*

Blattodea:
  *Blattella germanica, Periplaneta fulginosa, Periplaneta americana, Periplaneta brunnea, Blatta orientalis* and the like;

Thysanoptera:
  *Thrips palmi, Thrips tahaci, Frankliniella occidentalis* and the like;

Hymenoptera:
  Formicidae such as *Monomorium pharaonis*, Vespidae, bethylid wasp, Tenthredinidae such as *Athalia japonica*, and the like;

Orthoptera:
  Gryllotalpidae, Acrididae, and the like;

Aphaniptera:
  *Ctenocephalides felis, Ctenocephalides canis, Pulex irritans, Xenopsylla cheopis*, and the like;

Anoplura:
  *Pediculus humanus corporis, Phthirus pubis, Haematopinus eurysternus, Dalmalinia ovis*, and the like;

Isoptera:
  *Reticulitermes speratus, Coptotermes formosanus*, and the like;

Acarina:
  Tetranychidae such as *Tetranychus urticae, Panonychus citri, Oligonychus* spp., and the like,
  Eriophyidae such as *Aculops pelekassi* and the like,
  Tarsonemidae such as *Polyphagotarsonemus latus*, and the like,
  Tenuipalpidae,
  Tuckerellidae,
  Ixodidae such as *Haemaphysalis longicornis, Haemaphysalis flava, Dermacentor taiwanicus, Ixodes ovatus, Ixodes persulcatus, Boophilus microplus, Rhipicephalus sanguineus*, and the like,
  Acaridae such as *Tyrophagus putrescentiae*, and the like,
  Epidermoptidae such as *Dermatophagoides farinae, Dermatophagoides ptrenyssnus*, and the like,
  Cheyletidae such as *Cheyletus eruditus, Cheyletus malaccensis, Cheyletus moorei*, and the like,
  Dermanyssidae.

The noxious arthropods controlling composition of the present invention contains the compound of the present invention and an inert carrier. Generally, it is a preparation obtained by mixing the compound of the present invention and a solid carrier, a liquid carrier, a gaseous carrier and/or bait for poison bait, and if necessary, adding a surfactant and other adjuvant for formulation. The formulation includes an oil solution, an emulsion, a flowable formulation, a wettable powder, a granule, a powder, a microcapsule, and the like. These formulations can be converted to use into a poison bait, a sheet. In the noxious arthropods controlling composition of the present invention, the compound of the present invention is usually contained in an amount of 0.01% to 95% by weight.

The solid carrier for formulation includes, for example, a fine power and a granule of clays (e.g., kaolin clay, diatomite, bentonite, Fubasami clay, acid clay, etc.), synthetic hydrated silicon oxide, talc, ceramic, other inorganic minerals (e.g., sericite, quartz, sulfur, activated carbon, calcium carbonate, hydrated silica) or chemical fertilizers (e.g., ammonium sulfate, ammonium phosphate, ammonium nitrate, urea, ammonium chloride).

The liquid carrier for formulation includes, for example, water, alcohols (e.g., methanol, ethanol, isopropyl alcohol, butanol, hexanol, benzyl alcohol, ethylene glycol, propylene glycol, phenoxyethanol), ketones (e.g., acetone, methyl ethyl ketone, cyclohexanone), aromatic hydrocarbons (e.g., toluene, xylene, ethylbenzen, dodecylbenzen, phenylxylylethane, methylnaphthalene), aliphatic hydrocarbons (e.g., hexane, cyclohexane, kerosine, light oil), esters (e.g., ethyl acetate, butyl acetate, isopropyl mylistate, ethyl oleate, diisopropyl adipate, diisobutyl adipate, propyleneglycol monomethyl ether acetate), nitriles (e.g., acetonitrile, isobutyronitrile), ethers (e.g., diisopropyl ether, 1,4-dioxane, ethylene glycol dimethyl ether, diethylene glycol dimethyl ether, diethylene glycol monomethyl ether, propylene glycol monomethyl ether, dipropylene glycol monomethylether, 3-methoxy-3-methyl-1-butanol), acid amides (e.g., N,N-dimethylformamide, N,N-dimethylacetamide), halogenated hydrocarbons (e.g., dichloromethane, trichloroethane, carbontetrachloride), sulfoxides (e.g., dimethylsulfoxide), and vegetable oils (e.g., soy bean oil, cotton seed oil).

The gaseous carrier for formulation includes, for example, fluorocarbons, butane gas, liquefied petroleum gas (LPG), dimethyl ether, and carbon dioxide.

The surfactant for formulation includes, for example, non-ionic surfactant, such as polyoxyethylene alkyl ether, polyoxyethylene alkylaryl ether, polyethyleneglycol fatty acid ester; anionic surfactant, such as alkylsulfonic acid salts, alkylbenzenesulfonic acid salts, alkylsurfic acid salts.

The other adjuvant for formulation includes, for example, binders, dispersants and stabilizers, and specifically for example, casein, gelatin, polysaccharides (e.g., starch, gum arabic, cellulose derivatives, alginic acid), lignin derivatives, bentonite, synthetic water-soluble polymers (e.g., polyvinyl alcohol, polyvinylpyrrolidone, polyacrylic acid), PAP (isopropyl acid phosphate), BHT (2,6-di-t-butyl-4-methylphenol), BHA (a mixture of 2-t-butyl-4-methoxyphenol and 3-t-butyl-4-methoxyphenol).

The method for controlling noxious arthropods of the present invention is applying the compound of the present invention to arthropods directly and/or habitats of arthropods (e.g., plant, soil, indoor, in-body of animals, and so on). The compound of the present invention is usually used as the noxious arthropods controlling composition.

When the noxious arthropods controlling composition of the present invention is used for a control of arthropods in agriculture and forestry, the application amount is usually 1 to 10,000 g as the compound of the present invention per 10,000 $m^2$. The emulsions, wettable powders and flowable formulations of the noxious arthropods controlling composition of the present invention are usually applied after dilution with water to have an active ingredient concentration of 0.01 to 10,000 ppm, while powders and granules are usually applied as such.

These preparations and the dilutions of the preparation may be sprayed directly to arthropods or the plants to be protected from arthropods. The arthropods living in a soil can be controlled by treating the soil with these preparations.

Furthermore, the reginous preparations processed to sheets or strip form can be applied by a method such as winding around plants, stretching in the vicinity of plants and laying on the soil surface at the plant bottom.

When the noxious arthropods controlling composition of the present invention is used for a control of noxious arthropods in indoor (e.g., fly, mesquite, cockroach), the application amount is usually 0.01 to 1,000 mg as the compound of the present invention per 1 $m^2$ in case of application for plane surface, and 0.01 to 500 mg as the compound of the present invention per 1 $m^3$ in case of application for space. The emulsions, wettable powders and flowable formulations are usually applied after dilution with water to have an active ingredient concentration of 0.1 to 1,000 ppm, while oil solutions, aerosols, smoking agents and poison baits are usually applied as such.

The noxious arthropods controlling composition of the present invention can contain other noxious arthropods controlling compositions, nematocides, fungicides, herbicides, plant growth regulators, synergists, fertilizers, soil conditioners, animal feeds, and the like.

The active ingredients of noxious arthropods controlling composition and nematocides include, for example, organophosphorus compounds such as Fenitrothion, Fenthion, Pyridaphenthion, Diazinon, Chlorpyriphos, Chlorpyriphos-methyl, Acephate, Methidathion, Disulfoton, DDVP, Sulprofos, Cyanophos, Dioxabenzofos, Dimethoate, Phenthoate, Malathion, Trichlorfon, Azinphos-methyl, Monocrotophos Ethion Profenofos, Methyl-parathion, and Isoxathion; carbamate compounds such as BPMC, Benfuracarb, Propoxur, Carbosulfan, Carbaril, Methomyl, Ethiofencarb, Aldicarb, Oxamyl, Fenothiocarb, Thiodicarb, and Alanycarb; pyrethroid compounds such as Etofenprox, Fenvalerate, Esfenvalerate, Fenpropathrin, Cypermethrin, alfa-Cypermethrin, zeta-Cypermethrin, Permethrin, Cyhalothrin, lambda-Cyhalothrin, delta-Cyhalothrin, Cyfluthrin, beta-Cyfluthrin, Cycloprothrin, Fluvalinate, Flucythrinate, Bifenthrin, Acrinathrin, Traromethrin and Silafluofen; neonicotinoid compounds such as Acetamiprid, Nitenpyram, Thiamethoxiam and Thialoprid; Nereistoxin derivatives such as Cartap, Thiocyclam, and Bensultap; chlorinated hydrocarbon compounds such as Endosulfan, gamma-BHC, and 1,1-bis(chlorophenyl)-2,2,2-trichloroethanol; benzoylphenylurea compounds such as Chlorfluazuron, Teflubenzuron, Fulphenoxron, and Lufenuron; phenylhydrazide compounds such as Tebufenozide, Chromafenozide, Methoxyfenozide and Halofenozide; formamidine derivatives such as Amitraz and Chlordimeform; thiourea derivatives such as Diafenthiuron; Buprofezin; Chlorfenapyr; Spinosad and derivatives thereof, Emamectin benzoate; Indoxacarb; Pymetrozine; phenylpyrazole derivatives; Bromopropylate; Tetradifon; Chinomethionat; Propargite; Fenbutatin oxide; Cyhexatin; Hexathiazox; Clofentezine; Pyridaben; Fenpyroximate; Tebufenpyrad; Pyrimidifen; Fenazaquin; Bifenazate; Acequinocyl; Spirodiclofen; Spiromesifen; polynactin complexes [e.g., tetranactin, dinactin, trinactin]; Milbemectin; Avermectin; Azadilactin.

The present invention will be further illustrated by the following production examples, formulation examples, and test examples; however, the present invention is not limited to these examples.

The following describes the production examples for the present compounds.

PRODUCTION EXAMPLE 1

200 mg of the compound of formula (i):

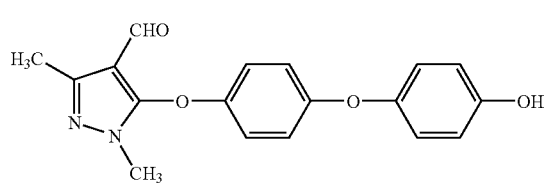

(i)

was dissolved in 3 ml of N,N-dimethylformamide, 100 mg of potassium carbonate and 100 mg of 1,1,3-trichloropropene were added to the mixture, and the mixture was stirred at 70° C. for one hour. The reaction mixture was cooled to room temperature, water and 10% hydrochloric acid were added thereto, and extracted with ethyl acetate. The organic layer was washed with water and saturated brine, dried over magnesium sulfate, and concentrated under reduced pressure. The residue was subjected to silica gel column chromatography to obtain 190 mg of the compound of formula (1):

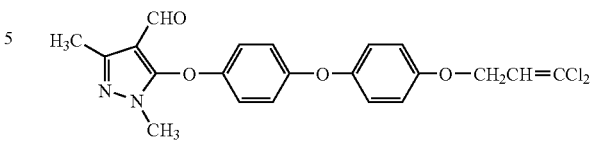

(1)

(hereinafter, referred as the present compound (1)).
$^1$H-NMR (CDCl$_3$, TMS) δ (ppm): 9.51 (1H, s), 6.83-6.97 (8H, m), 6.16 (1H, t), 4.64 (2H, d), 3.66 (3H, s), 2.45 (3H, s)

PRODUCTION EXAMPLE 2

440 mg of the compound of formula (ii):

(ii)

was dissolved in 5 ml of N,N-dimethylformamide, 220 mg of potassium carbonate and 210 mg of 1,1,3-trichloropropene were added to the mixture, and the mixture was stirred at 70° C. for one hour. The reaction mixture was cooled to room temperature, water and 10% hydrochloric acid were added thereto, and extracted with ethyl acetate. The organic layer was washed with water and saturated brine, dried over magnesium sulfate, and concentrated under reduced pressure. The residue was subjected to silica gel column chromatography to obtain 480 mg of the compound of formula (2):

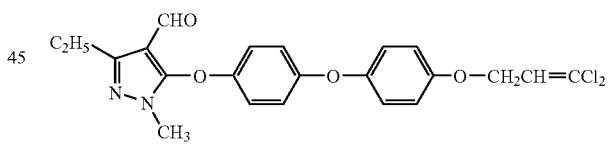

(2)

(hereinafter, referred as the present compound (2)).
$^1$H-NMR (CDCl$_3$, TMS) δ (ppm): 9.53 (1H, s), 6.86-6.98 (8H, m), 6.16 (1H, t), 3.66 (3H, s), 2.85 (2H, q), 1.26 (3H, t)

PRODUCTION EXAMPLE 3

200 mg of the present compound (1) was dissolved in 5 ml of pyridine, 45 mg of methoxyamine hydrochloric acid salt was added to the mixture under ice-cooling, and the mixture was stirred at room temperature for two hours. The reaction mixture was concentrated under reduced pressure. Water and 10% hydrochloric acid were added to the residue, and extracted with ethyl acetate. The organic layer was washed with water and saturated brine, dried over magnesium sulfate, and concentrated under reduced pressure. The residue was subjected to silica gel column chromatography to obtain 200 mg of the compound of formula (3):

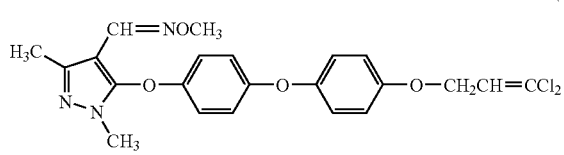
(3)

(hereinafter, referred as the present compound (3)).
$^1$H-NMR (CDCl$_3$, TMS) δ (ppm): 7.74 (1H, s), 6.16-6.96 (8H, m), 6.16 (1H, t), 4.64 (2H, d), 3.81 (3H, s), 3.62 (3H, s), 2.38 (3H, s)

PRODUCTION EXAMPLE 4

By using 50 mg of ethoxyamine hydrochloric acid salt instead of methoxyamine hydrochloric acid salt according to Production Example 3 was obtained 170 mg of the compound of formula (4):

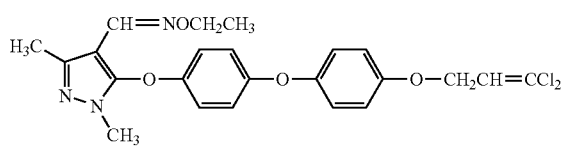
(4)

(hereinafter, referred as the present compound (4)).
$^1$H-NMR (CDCl$_3$, TMS) δ (ppm): 7.75 (1H, s), 6.83-6.95 (8H, m), 6.15 (1H, t), 4.63 (2H, d), 4.04 (2H, q), 3.61 (3H, s), 2.37 (3H, s), 1.21 (3H, t)

PRODUCTION EXAMPLE 5

By using 62 mg of isopropoxyamine hydrochloric acid salt instead of methoxyamine hydrochloric acid salt according to Production Example 3 was obtained 140 mg of the compound of formula (5):

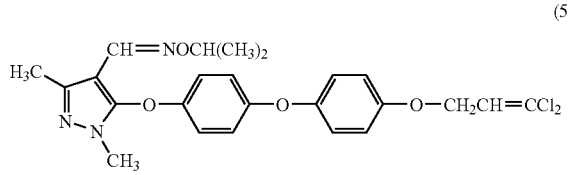
(5)

(hereinafter, referred as the present compound (5)).
$^1$H-NMR (CDCl$_3$, TMS) δ (ppm): 7.77 (1H, s), 6.82-6.98 (8H, m), 6.15 (1H, t), 5.37 (1H, q), 4.63 (2H, d), 3.61 (3H, s), 2.37 (3H, s), 1.73 (6H, d)

PRODUCTION EXAMPLE 6

By using 248 mg the present compound (1) and 80 mg of tert-butoxyamine hydrochloric acid salt instead of methoxyamine hydrochloric acid salt according to Production Example 3 was obtained 270 mg of the compound of formula (6):

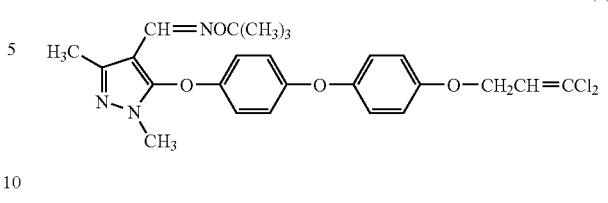
(6)

(hereinafter, referred as the present compound (6)).
$^1$H-NMR (CDCl$_3$, TMS) δ (ppm): 7.76 (1H, s), 6.82-6.99 (8H, m), 6.16 (1H, t), 4.63 (2H, d), 3.62 (3H, s), 2.38 (3H, s), 1.21 (9H, s)

PRODUCTION EXAMPLE 7

By using 77 mg of pentyloxyamine hydrochloric acid salt instead of methoxyamine hydrochloric acid salt according to Production Example 3 was obtained 130 mg of the compound of formula (7):

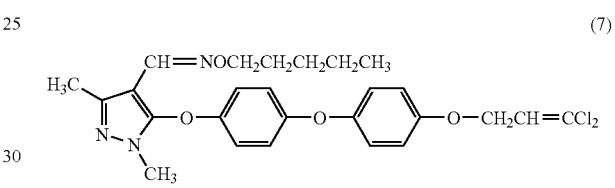
(7)

(hereinafter, referred as the present compound (7)).
$^1$H-NMR (CDCl$_3$, TMS) δ (ppm): 7.76 (1H, s), 6.83-6.95 (8H, m), 6.16 (1H, t), 4.64 (2H, d), 3.98 (2H, t), 3.61 (3H, s), 2.37 (3H, s), 1.58 (2H, br), 1.30-1.32 (5H, m), 0.89 (3H, t)

PRODUCTION EXAMPLE 8

By using 60 mg of 2-propynyloxyamine hydrochloric acid salt instead of methoxyamine hydrochloric acid salt according to Production Example 3 was obtained 140 mg of the compound of formula (8):

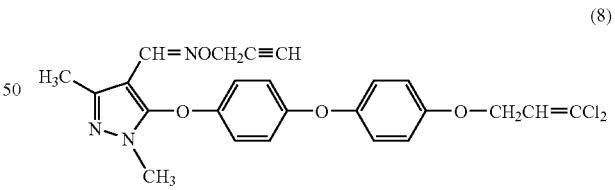
(8)

(hereinafter, referred as the present compound (8)).
$^1$H-NMR (CDCl$_3$, TMS) δ (ppm): 7.80 (1H, s), 6.84-6.96 (8H, m), 6.16 (1H, t), 4.64 (2H, d), 4.60 (1H, s), 3.62 (3H, s), 2.44 (3H, s)

PRODUCTION EXAMPLE 9

By using 55 mg of allyloxyamine hydrochloric acid salt instead of methoxyamine hydrochloric acid salt according to Production Example 3 was obtained 200 mg of the compound of formula (9):

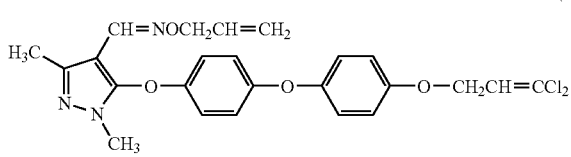
(9)

(hereinafter, referred as the present compound (9)).

1H-NMR (CDCl$_3$, TMS) δ (ppm): 7.79 (1H, s), 6.83-6.95 (8H, m), 6.15 (1H, t), 5.90-5.97 (1H, m), 5.16-5.28 (2H, m), 4.64 (2H, d), 4.50 (2H, d), 3.61 (3H, s)

PRODUCTION EXAMPLE 10

By using 100 mg of 3,3-dichloro-2-propenyloxyamine hydrochloric acid salt instead of methoxyamine hydrochloric acid salt according to Production Example 3 was obtained 130 mg of the compound of formula (10):

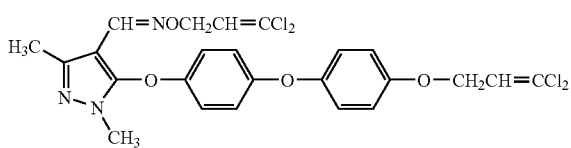
(10)

(hereinafter, referred as the present compound (10)).

$^1$H-NMR (CDCl$_3$, TMS) δ (ppm): 7.75 (1H, s), 6.83-6.95 (8H, m), 6.15 (1H, t), 6.03 (1H, t), 4.64 (2H, d), 4.57 (2H, d), 3.62 (3H, s), 2.36 (3H, s)

PRODUCTION EXAMPLE 11

By using 75 mg of benzyloxyamine hydrochloric acid salt instead of methoxyamine hydrochloric acid salt according to Production Example 3 was obtained 165 mg of the compound of formula (11):

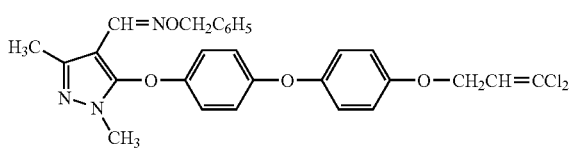
(11)

(hereinafter, referred as the present compound (11)).

$^1$H-NMR (CDCl$_3$, TMS) δ (ppm): 7.80 (1H, s), 7.28-7.32 (5H, m), 6.81-6.95 (8H, m), 6.16 (1H, t), 5.02 (2H, s), 4.63 (2H, d), 3.60 (3H, s), 2.35 (3H, s)

PRODUCTION EXAMPLE 12

By using 55 mg of (E)-2-butenyloxyamine hydrochloric acid salt instead of methoxyamine hydrochloric acid salt according to Production Example 3 was obtained 90 mg of the compound of formula (12):

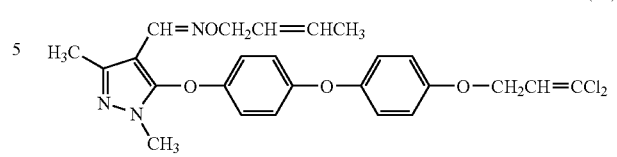
(12)

(hereinafter, referred as the present compound (12)).

$^1$H-NMR (CDCl$_3$, TMS) δ (ppm): 7.77 (1H, s), 6.83-6.96 (8H, m), 6.16 (1H, t), 5.60-6.17 (2H, m), 4.64 (2H, d), 4.42 (2H, d), 3.62 (3H, s), 2.37 (3H, q) 1.71 (3H, d)

PRODUCTION EXAMPLE 13

190 mg of the present compound (2) was dissolved in 5 ml of pyridine, 43 mg of methoxyamine hydrochloric acid salt was added to the mixture under ice-cooling, and the mixture was stirred at room temperature for two hours. The reaction mixture was concentrated under reduced pressure. Water and 10% hydrochloric acid were added to the residue, and extracted with ethyl acetate. The organic layer was washed with water and saturated brine, dried over magnesium sulfate, and concentrated under reduced pressure. The residue was subjected to silica gel column chromatography to obtain 150 mg of the compound of formula (13):

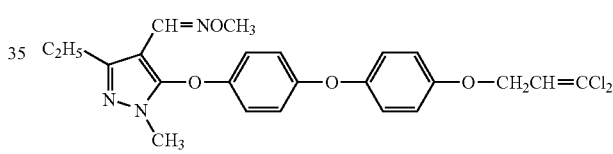
(13)

(hereinafter, referred as the present compound (13)).

$^1$H-NMR (CDCl$_3$, TMS) δ (ppm): 7.74 (1H, s), 6.83-6.95 (8H, m), 6.16 (1H, t), 4.64 (2H, d), 3.80 (3H, s), 3.62 (3H, s), 2.78 (2H, q), 1.27 (3H, t)

PRODUCTION EXAMPLE 14

By using 180 mg of the present compound (2) and 50 mg of ethoxyamine hydrochloric acid salt instead of methoxyamine hydrochloric acid salt according to Production Example 3 was obtained 160 mg of the compound of formula (14):

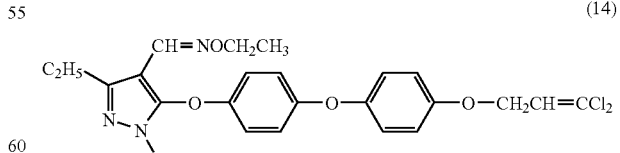
(14)

(hereinafter, referred as the present compound (14)).

$^1$H-NMR (CDCl$_3$, TMS) δ (ppm): 7.77 (1H, s), 6.83-6.95 (8H, m), 6.16 (1H, t), 4.64 (2H, d), 4.04 (2H, q), 3.62 (3H, s), 2.77 (2H, q), 1.19-1.28 (6H, m)

PRODUCTION EXAMPLE 15

190 mg of the compound of formula (iii):

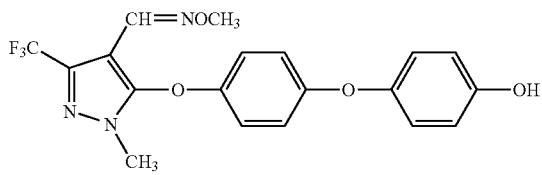

(iii)

was dissolved in 2 ml of N,N-dimethylformamide, 80 mg of potassium carbonate and 80 mg of 1,1,3-trichloropropene were added to the mixture, and the mixture was stirred at 80° C. for one hour. The reaction mixture was cooled to room temperature, water and 10% hydrochloric acid were added thereto, and extracted with ethyl acetate. The organic layer was washed with water and saturated brine, dried over magnesium sulfate, and concentrated under reduced pressure. The residue was subjected to silica gel column chromatography to obtain 150 mg of the compound of formula (15):

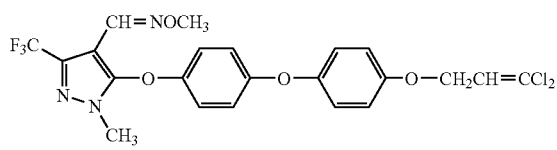

(15)

(hereinafter, referred as the present compound (15)).

$^1$H-NMR (CDCl$_3$, TMS) δ (ppm): 7.84 (1H, s), 6.85-6.95 (8H, m), 6.16 (1H, t), 4.64 (2H, d), 3.78 (3H, s), 3.71 (3H, s)

PRODUCTION EXAMPLE 16

170 mg of the compound of the formula (iv):

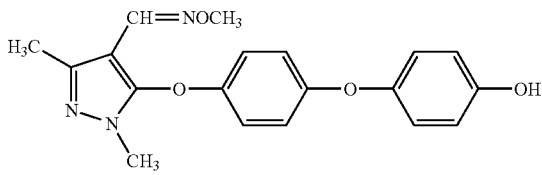

(iv)

was dissolved in 3 ml of N,N-dimethylformamide, 80 mg of potassium carbonate and 70 mg of 1,3-dichloro-2-butene were added to the mixture, and the mixture was stirred at 80° C. for one hour. The reaction mixture was cooled to room temperature, water and 10% hydrochloric acid were added thereto, and extracted with ethyl acetate. The organic layer was washed with water and saturated brine, dried over magnesium sulfate, and concentrated under reduced pressure. The residue was subjected to silica gel column chromatography to obtain 160 mg of the compound of formula (16):

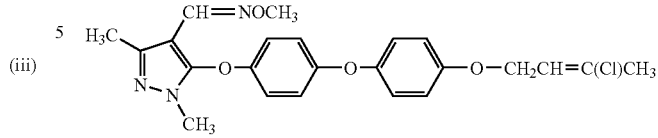

(16)

(hereinafter, referred as the present compound (16)).

$^1$H-NMR (CDCl$_3$, TMS) δ (ppm): 7.73 (1H, s), 6.82-6.96 (8H, m), 5.76 (1H, t), 4.66 (2H, d), 4.48 (3H, s), 3.61 (3H, s), 2.38 (3H, s), 2.17 (3H, s)

PRODUCTION EXAMPLE 17

By using 60 mg of 1,3-dichloropropene instead of 1,3-dichloro-2-butene according to Production Example 16 was obtained 130 mg of the compound of formula (17):

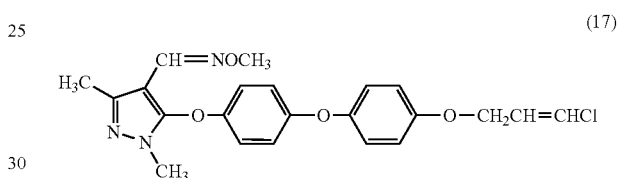

(17)

(hereinafter, referred as the present compound (17)).

$^1$H-NMR (CDCl$_3$, TMS) δ (ppm): 7.74 (1H, s), 6.83-6.95 (8H, m), 6.37-6.40 (1H, m), 6.13-6.19 (1H, m), 4.50 (2H, d), 3.80 (3H, s), 3.61 (3H, s), 2.38 (3H, s)

PRODUCTION EXAMPLE 18

114 mg of the present compound (1) was dissolved in 3 ml of pyridine, 25 mg of hydroxylamine hydrochloric acid salt was added to the mixture under ice-cooling, and the mixture was stirred at room temperature for thirty minutes. The reaction mixture was concentrated under reduced pressure. Water and 10% hydrochloric acid were added to the residue, and extracted with ethyl acetate. The organic layer was washed with water and saturated brine, dried over magnesium sulfate, and concentrated under reduced pressure. The residue was subjected to silica gel column chromatography to obtain 80 mg of the compound of formula (18):

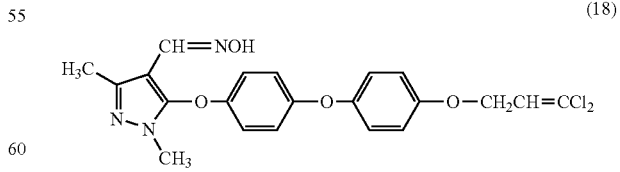

(18)

(hereinafter, referred as the present compound (18)).

$^1$H-NMR (CDCl$_3$, TMS) δ (ppm): 7.83 (1H, s), 7.08 (1H, s), 6.84-6.96 (8H, m), 6.16 (1H, t), 4.64 (2H, d), 3.61 (3H, s), 2.36 (3H, s)

PRODUCTION EXAMPLE 19

By using 370 mg of the present compound (1) and 110 mg of propoxyamine hydrochloric acid salt instead of methoxyamine hydrochloric acid salt according to Production Example 3 was obtained 400 mg of the compound of formula (19):

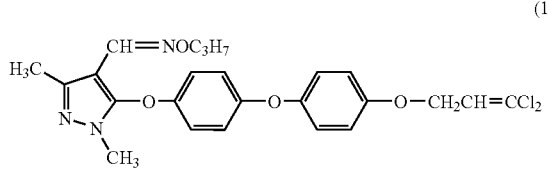

(19)

(hereinafter, referred as the present compound (19)).
$^1$H-NMR (CDCl$_3$, TMS) δ (ppm): 0.90 (3H, t), 1.61 (2H, m), 2.37 (3H, s), 3.62 (3H, s), 3.94 (2H, t), 4.64 (2H, d), 6.16 (1H, t), 6.83-6.96 (8H, m), 7.77 (1H, s)

PRODUCTION EXAMPLE 20

By using 150 mg of the present compound (1) and 60 mg of neopentyloxyamine hydrochloric acid salt instead of methoxyamine hydrochloric acid salt according to Production Example 3 was obtained 130 mg of the compound of formula (20):

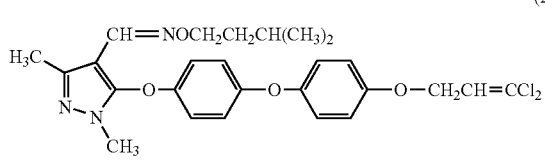

(20)

(hereinafter, referred as the present compound (20)).
$^1$H-NMR (CDCl$_3$, TMS) δ (ppm): 0.90 (6H, d), 1.46-1.70 (3H, m), 2.37 (3H, s), 3.61 (3H, s), 4.02 (2H, t), 4.64 (2H, d), 6.16 (1H, t), 6.82-6.96 (8H, m), 7.75 (1H, s)

PRODUCTION EXAMPLE 21

By using 150 mg of the present compound (1) and 60 mg of 3-methyl-2-butenyloxyamine hydrochloric acid salt instead of methoxyamine hydrochloric acid salt according to Production Example 3 was obtained 150 mg of the compound of formula (21):

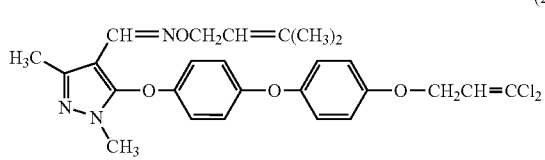

(21)

(hereinafter, referred as the present compound (21)).
$^1$H-NMR (CDCl$_3$, TMS) δ (ppm): 1.70 (3H, s), 1.75 (3H, s), 2.37 (3H, s), 3.61 (3H, s), 4.50 (2H, d), 4.63 (2H, d), 5.38 (1H, m), 6.16 (1H, t), 6.82-6.96 (8H, m), 7.77 (1H, s)

PRODUCTION EXAMPLE 22

By using 150 mg of the present compound (1) and 50 mg of 1-methyl-2-propynyloxyamine hydrochloric acid salt instead of methoxyamine hydrochloric acid salt according to Production Example 3 was obtained 110 mg of the compound of formula (22):

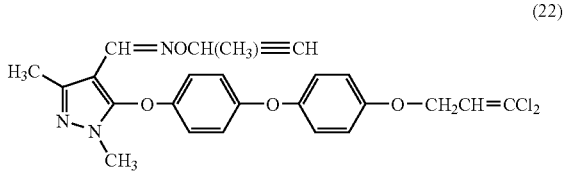

(22)

(hereinafter, referred as the present compound (22)).
$^1$H-NMR (CDCl$_3$, TMS) δ (ppm): 1.46 (3H, d), 2.38 (3H, s), 2.43 (1H, d), 3.62 (3H, s), 4.63 (2H, d), 4.79 (1H, m), 6.16 (1H, t), 6.83-6.96 (8H, m), 7.79 (1H, s)

PRODUCTION EXAMPLE 23

By using 150 mg of the present compound (1) and 50 mg of 1-methylpropoxyamine hydrochloric acid salt instead of methoxyamine hydrochloric acid salt according to Production Example 3 was obtained 170 mg of the compound of formula (23):

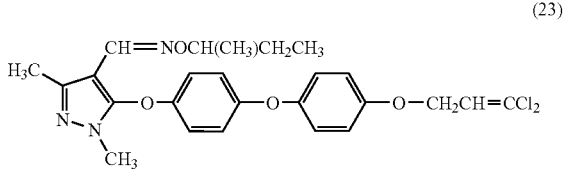

(23)

(hereinafter, referred as the present compound (23)).
$^1$H-NMR (CDCl$_3$, TMS) δ (ppm): 0.88 (3H, t), 1.15 (3H, d), 1.41-1.64 (2H, m), 2.37 (3H, s), 3.62 (3H, s), 4.04 (1H, m), 4.63 (2H, d), 6.16 (1H, t) 6.83-6.96 (8H, m), 7.76 (1H, s)

PRODUCTION EXAMPLE 24

By using 150 mg of the present compound (1) and 70 mg of 1,2-dimethylpropoxyamine hydrochloric acid salt instead of methoxyamine hydrochloric acid salt according to Production Example 3 was obtained 160 mg of the compound of formula (24):

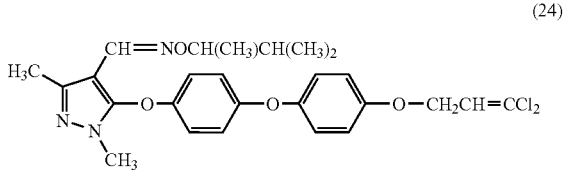

(24)

(hereinafter, referred as the present compound (24)).
$^1$H-NMR (CDCl$_3$, TMS) δ (ppm): 0.83 (3H, d), 0.88 (3H, d), 1.11 (3H, d), 1.82 (1H, m), 2.37 (3H, s), 3.62 (3H, s), 3.89 (1H, m), 4.64 (2H, d), 6.16 (1H, t), 6.82-6.96 (8H, m), 7.76 (1H, s)

PRODUCTION EXAMPLE 25

By using 150 mg of the present compound (1) and 50 mg of 2-fluoroethoxyamine hydrochloric acid salt instead of methoxyamine hydrochloric acid salt according to Production Example 3 was obtained 130 mg of the compound of formula (25):

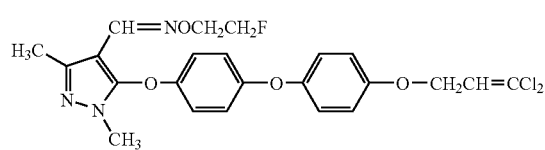

(25)

(hereinafter, referred as the present compound (25)).
$^1$H-NMR (CDCl$_3$, TMS) δ (ppm): 2.36 (3H, s), 3.62 (3H, s), 4.21 (2H, dt), 4.56 (2H, dt), 4.64 (2H, d), 6.16 (1H, t), 6.82-6.97 (8H, m), 7.83 (1H, s)

PRODUCTION EXAMPLE 26

By using 150 mg of the present compound (1) and 70 mg of 3,3,3-trifluoropropoxyamine hydrochloric acid salt instead of methoxyamine hydrochloric acid salt according to Production Example 3 was obtained 140 mg of the compound of formula (26):

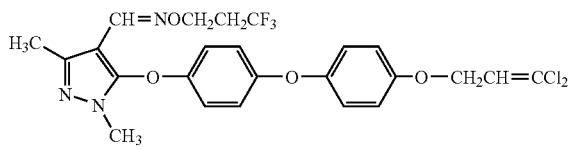

(26)

(hereinafter, referred as the present compound (26)).
$^1$H-NMR (CDCl$_3$, TMS) δ (ppm): 2.36 (5H, m), 3.63 (3H, s), 4.19 (2H, t), 4.64 (2H, d), 6.16 (1H, t), 6.83-6.96 (8H, m), 7.77 (1H, s)

PRODUCTION EXAMPLE 27

By using 150 mg of the present compound (1) and 70 mg of 4,4,4-trifluorobutoxyamine hydrochloric acid salt instead of methoxyamine hydrochloric acid salt according to Production Example 3 was obtained 120 mg of the compound of formula (27):

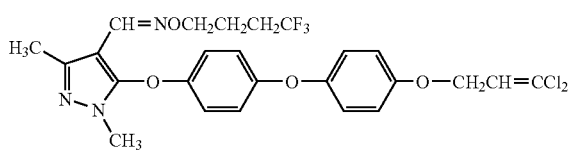

(27)

(hereinafter, referred as the present compound (27)).
$^1$H-NMR (CDCl$_3$, TMS) δ (ppm): 1.86 (2H, m), 2.12 (2H, m), 2.36 (3H, s), 3.62 (3H, s), 4.03 (2H, t), 4.64 (2H, d), 6.16 (1H, t), 6.82-6.96 (8H, m) 7.77 (1H, s)

PRODUCTION EXAMPLE 28

By using 150 mg of the present compound (1) and 70 mg of 3-chloro-2-propenyloxyamine hydrochloric acid salt instead of methoxyamine hydrochloric acid salt according to Production Example 3 was obtained 160 mg of the compound of formula (28):

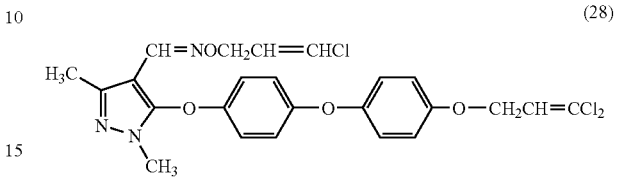

(28)

(hereinafter, referred as the present compound (28)) as the mixture of diastereomers.
$^1$H-NMR (CDCl$_3$, TMS) δ (ppm): 2.36 (1.5H, s), 2.36 (1.5H, s), 3.62 (3H, s), 4.45 (1H, dd), 4.64 (2H, d), 4.70 (1H, dd), 5.94 (0.5H, m), 6.04 (0.5H, m), 6.16 (2H, m), 6.83-6.96 (8H, m), 7.76 (0.5H, s), 7.77 (0.5H, s)

PRODUCTION EXAMPLE 29

By using 150 mg of the present compound (1) and 110 mg of 3,3-dibromo-2-propenyloxyamine hydrochloric acid salt instead of methoxyamine hydrochloric acid salt according to Production Example 3 was obtained 220 mg of the compound of formula (29):

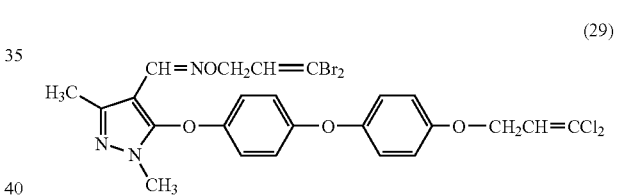

(29)

(hereinafter, referred as the present compound (29)).
$^1$H-NMR (CDCl$_3$, TMS) δ (ppm): 2.36 (3H, s), 3.62 (3H, s), 4.48 (2H, d), 4.64 (2H, d), 6.16 (1H, t), 6.59 (1H, t), 6.83-6.97 (8H, m), 7.76 (1H, s)

PRODUCTION EXAMPLE 30

By using 150 mg of the present compound (1) and 60 mg of butoxyamine hydrochloric acid salt instead of methoxyamine hydrochloric acid salt according to Production Example 3 was obtained 160 mg of the compound of formula (30):

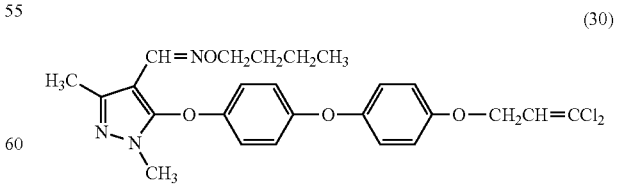

(30)

(hereinafter, referred as the present compound (30)).
$^1$H-NMR (CDCl$_3$, TMS) δ (ppm): 0.91 (3H, t), 1.35 (2H, m), 1.56 (2H, m), 2.37 (3H, s), 3.62 (3H, s), 4.00 (2H, t), 4.64 (2H, d), 6.16 (1H, t), 6.82-6.96 (8H, m), 7.76 (1H, s)

PRODUCTION EXAMPLE 31

200 mg of the present compound (18) was dissolved in 2 ml of N,N-dimethylformamide, 120 mg of potassium carbonate and 110 mg of bromoacetonitrile were added to the mixture, and the mixture was stirred at 40° C. for five hours. The reaction mixture was cooled to room temperature, the reaction mixture added to dilute hydrochloric acid, and extracted with ethyl acetate. The organic layer was washed with water and saturated brine, dried over magnesium sulfate, and concentrated under reduced pressure. The residue was subjected to silica gel column chromatography to obtain 80 mg of the compound of formula (31):

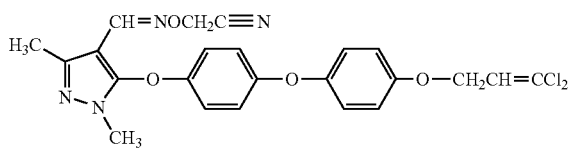

(31)

(hereinafter, referred as the present compound (31)).
$^1$H-NMR (CDCl$_3$, TMS) δ (ppm): 2.38 (3H, s), 3.63 (3H, s), 4.63 (4H, m), 6.16 (1H, t), 6.85-6.98 (8H, m), 7.82 (1H, s)

PRODUCTION EXAMPLE 32

By using 3.50 g of the present compound (1) and 1.35 g of 2,2,2-trifluoroethoxyamine hydrochloric acid salt instead of methoxyamine hydrochloric acid salt according to Production Example 3 was obtained 3.85 g of the compound of formula (32):

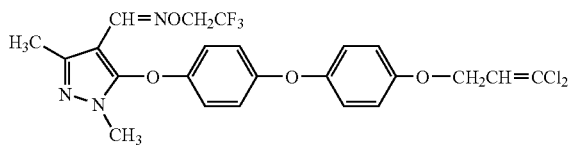

(32)

(hereinafter, referred as the present compound (32)).
$^1$H-NMR (CDCl$_3$, TMS) δ (ppm): 2.36 (3H, s), 3.62 (3H, s), 4.34 (2H, q), 4.64 (2H, d), 6.16 (1H, t), 6.82-6.97 (8H, m), 7.83 (1H, s)

PRODUCTION EXAMPLE 33

150 mg of the present compound (18) was dissolved in 2 ml of N,N-dimethylformamide, 90 mg of potassium carbonate and 90 mg of 1-bromo-2-methylpropane were added to the mixture, and the mixture was stirred at 70° C. for ten hours. The reaction mixture was cooled to room temperature, the reaction mixture was added to dilute hydrochloric acid, and extracted with ethyl acetate. The organic layer was washed with water and saturated brine, dried over magnesium sulfate, and concentrated under reduced pressure. The residue was subjected to silica gel column chromatography to obtain 40 mg of the compound of formula (33):

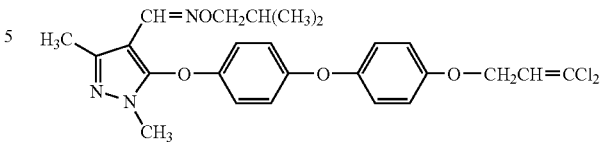

(33)

(hereinafter, referred as the present compound (33)).
$^1$H-NMR (CDCl$_3$, TMS) δ (ppm): 0.88 (6H, d), 1.90 (1H, m), 2.37 (3H, s), 3.62 (3H, s), 3.76 (2H, d), 4.64 (2H, d), 6.16 (1H, t), 6.83-6.96 (8H, m) 7.77 (1H, s)

PRODUCTION EXAMPLE 34

90 mg of sodium hydride (60% oil suspension) was suspended in 5 ml of hexane, and 460 mg of 5-chloro-1,3-dimethyl-1H-pyrazole-4-carbaldehyde was added to the mixture at room temperature. Afterward 500 mg of the compound of formula (v):

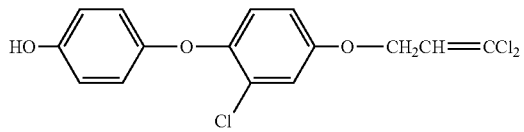

(v)

was added dropwise to the mixture under reflux condition, and the mixture was stirred five hours under reflux condition. Saturated ammonium chloride aqueous solution was added to the reaction mixture, and extracted with ethyl acetate. The organic layer was washed with dilute hydrochloric acid, water and saturated brine, dried over magnesium sulfate, and concentrated under reduced pressure. The residue was subjected to silica gel column chromatography to obtain 260 mg of the compound of the formula (34):

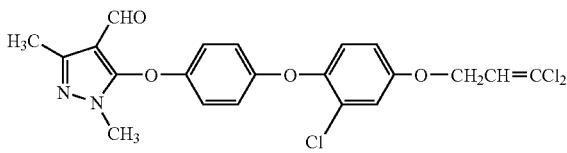

(34)

(hereinafter, referred as the present compound (34)).
$^1$H-NMR (CDCl$_3$, TMS) δ (ppm): 2.45 (3H, s), 3.65 (3H, s), 4.64 (2H, d), 6.15 (1H, t), 6.78-7.01 (7H, m), 9.51 (1H, s)

PRODUCTION EXAMPLE 35

150 mg of the present compound (34) was dissolved in 2 ml of pyridine, 40 mg of 2-propynyloxyamine hydrochloric acid salt was added to the mixture under ice-cooling, and the mixture was stirred at room temperature for five hours. The reaction mixture was concentrated under reduced pressure. Dilute hydrochloric acid were added to the residue, and extracted with ethyl acetate. The organic layer was washed with water and saturated brine, dried over magnesium sulfate, and concentrated under reduced pressure. The residue was subjected to silica gel column chromatography to obtain 150 mg of the compound of formula (35):

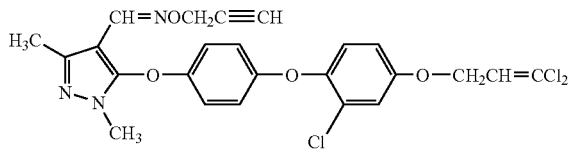

(35)

(hereinafter, referred as the present compound (35)).

$^1$H-NMR (CDCl$_3$, TMS) δ (ppm): 2.36 (3H, s), 2.43 (1H, t), 3.62 (3H, s), 4.59 (2H, d), 4.63 (2H, d), 6.15 (1H, t), 6.76-7.01 (7H, m), 7.80 (1H, s)

PRODUCTION EXAMPLE 36

200 mg of the present compound (18) was dissolved in 2 ml of N,N-dimethylformamide, 80 mg of potassium carbonate and 60 mg of 2,3-dichloropropene were added to the mixture at room temperature, and the mixture was stirred at 70° C. for ten hours. The reaction mixture was cooled to room temperature, added to dilute hydrochloric acid, and extracted with ethyl acetate. The organic layer was washed with water and saturated brine, dried over magnesium sulfate, and concentrated under reduced pressure. The residue was subjected to silica gel column chromatography to obtain 130 mg of the compound of formula (36):

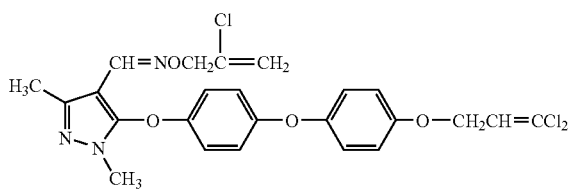

(36)

(hereinafter, referred as the present compound (36)).

$^1$H-NMR (CDCl$_3$, TMS) δ (ppm): 2.35 (3H, s), 3.62 (3H, s), 4.52 (2H, s), 4.64 (2H, d), 5.33 (1H, s), 5, 35 (1H, s), 6.16 (1H, t), 6.82-6.97 (8H, m), 7.84 (1H, s)

PRODUCTION EXAMPLE 37

200 mg of the present compound (18) was dissolved in 2 ml of N,N-dimethylformamide, 90 mg of potassium carbonate and 110 mg of 2-chloroethyl methansulfonate were added to the mixture at room temperature, and the mixture was stirred at 70° C. for ten hours. The reaction mixture was cooled to room temperature, added to dilute hydrochloric acid, and extracted with ethyl acetate. The organic layer was washed with water and saturated brine, dried over magnesium sulfate, and concentrated under reduced pressure. The residue was subjected to silica gel column chromatography to obtain 90 mg of the compound of formula (37):

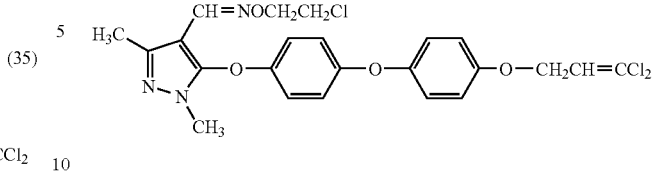

(37)

(hereinafter, referred as the present compound (37)).

$^1$H-NMR (CDCl$_3$, TMS) δ (ppm): 2.35 (3H, s), 3.60 (2H, t), 3.63 (3H, s), 4.18 (2H, t), 4.64 (2H, d), 6.16 (1H, t), 6.83-6.98 (8H, m), 7.82 (1H, s)

PRODUCTION EXAMPLE 38

270 mg of the compound of the formula (vi):

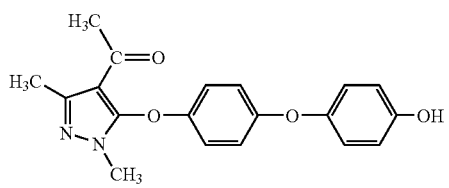

(vi)

was dissolved in 2 ml of N,N-dimethylformamide, 150 mg of potassium carbonate and 140 mg of 1,1,3-trichloropropene were added to the mixture, and the mixture was stirred at room temperature for ten hours. The reaction mixture was cooled, added to dilute hydrochloric acid, and extracted with ethyl acetate. The organic layer was washed with water and saturated brine, dried over magnesium sulfate, and concentrated under reduced pressure. The residue was subjected to silica gel column chromatography to obtain 350 mg of the compound of formula (38):

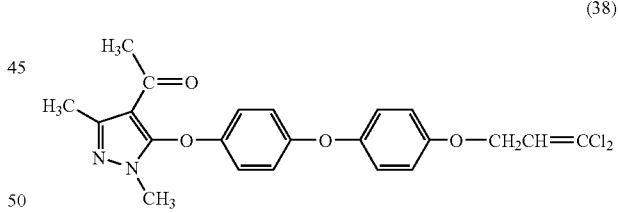

(38)

(hereinafter, referred as the present compound (38)).

$^1$H-NMR (CDCl$_3$, TMS) δ (ppm): 2.25 (3H, s), 2.47 (3H, s), 3.57 (3H, s), 4.64 (2H, d), 6.16 (1H, t), 6.81-6.97 (8H, m)

PRODUCTION EXAMPLE 39

160 mg of the present compound (38) was dissolved in 2 ml of pyridine, 50 mg of 2-propynyloxyamine hydrochloric acid salt was added to the mixture at room temperature, and the mixture was stirred at room temperature for ten hours. The reaction mixture was concentrated under reduced pressure. Dilute hydrochloric acid were added to the residue, and extracted with ethyl acetate. The organic layer was washed with water and saturated brine, dried over magnesium sulfate, and concentrated under reduced pressure. The residue was subjected to silica gel column chromatography to obtain 170 mg of the compound of formula (39):

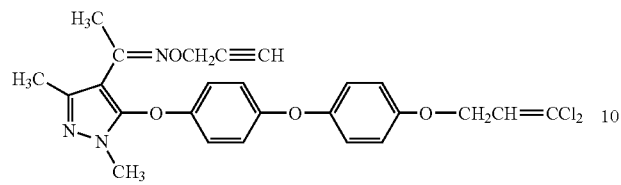

(hereinafter, referred as the present compound (39)).

$^1$H-NMR (CDCl$_3$, TMS) δ (ppm): 2.00 (3H, s), 2.39 (3H, s), 2.43 (1H, t), 3.58 (3H, s), 4.64 (2H, d), 4.65 (2H, d), 6.16 (1H, t), 6.77-6.97 (8H, m)

PRODUCTION EXAMPLE 40

300 mg of the present compound (18) was dissolved in 3 ml of N,N-dimethylformamide, 100 mg of potassium carbonate and 110 mg of 1-bromo-2-butyne were added to the mixture at room temperature, and the mixture was stirred at 40° C. for ten hours. The reaction mixture was cooled to room temperature, added to dilute hydrochloric acid, and extracted with ethyl acetate. The organic layer was washed with water and saturated brine, dried over magnesium sulfate, and concentrated under reduced pressure. The residue was subjected to silica gel column chromatography to obtain 250 mg of the compound of formula (40):

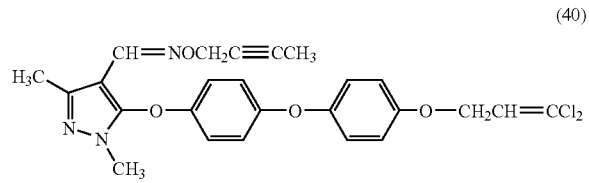

(hereinafter, referred as the present compound (40)).

$^1$H-NMR (CDCl$_3$, TMS) δ (ppm): 1.85 (3H, t), 2.37 (3H, s), 3.62 (3H, s), 4.57 (2H, q), 4.64 (2H, d), 6.16 (1H, t), 6.83-6.97 (8H, m), 7.79 (1H, s)

Next, the following describes the reference production examples for the intermediates of the present invention

REFERENCE PRODUCTION EXAMPLE 1

330 mg of the compound of formula (i) was dissolved in 3 ml of pyridine, 100 mg of methoxyamine hydrochloric acid salt was added thereto at ice-cooling, and the mixture was stirred at room temperature for two hours. The reaction mixture was concentrated under reduced pressure. Water and 10% hydrochloric acid were added to the residue, and extracted with ethyl acetate. The organic layer was washed with water and saturated brine, dried over magnesium sulfate, and concentrated under reduced pressure. The residue was subjected to silica gel column chromatography to obtain 290 mg of the compound of formula (iv).

$^1$H-NMR (CDCl$_3$, TMS) δ (ppm): 7.74 (1H, s), 6.80-6.90 (8H, m), 5.97 (1H, s), 3.81 (3H, s), 3.61 (3H, s), 2.39 (3H, s)

REFERENCE PRODUCTION EXAMPLE 2

240 mg of the compound of formula (vii)

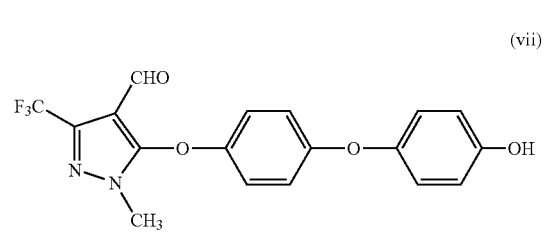

was dissolved in 3 ml of pyridine, 64 mg of methoxyamine hydrochloric acid salt was added thereto at ice-cooling, and the mixture was stirred at room temperature for two hours. The reaction mixture was concentrated under reduced pressure. Water and 10% hydrochloric acid were added to the residue, and extracted with ethyl acetate. The organic layer was washed with water and saturated brine, dried over magnesium sulfate, and concentrated under reduced pressure. The residue was subjected to silica gel column chromatography to obtain 260 mg of the compound of formula (iii).

$^1$H-NMR (CDCl$_3$, TMS) δ (ppm): 7.83 (1H, s), 6.79-7.11 (8H, m), 5.28 (1H, br), 3.78 (3H, s), 3.70 (3H, s)

REFERENCE PRODUCTION EXAMPLE 3

300 mg of 4,4'-dihydroxydiphenyl ether was dissolved in 5 ml of N,N-dimethylformamide, 120 mg of sodium hydride (60% oil suspension) was added thereto under ice-cooling, the mixture was stirred at room temperature for ten minutes. Afterward, 230 mg of 5-chloro-1,3-dimethyl-1H-pyrazole-4-carboaldehyde in 3 ml of N,N-dimethylformamide was added dropwise at 70° C. under stirring over ten minutes, stirred at 70° C. for two hours. The reaction mixture was cooled to room temperature, water and 10% hydrochloric acid were added thereto, and extracted with ethyl acetate. The organic layer was washed with water and saturated brine, dried over magnesium sulfate, and concentrated under reduced pressure. The residue was subjected to silica gel column chromatography to obtain 260 mg of the compound of formula (i).

$^1$H-NMR (CDCl$_3$, TMS) δ (ppm): 9.50 (1H, s), 6.76-6.99 (8H, m), 5.44 (1H, br), 3.66 (3H, s), 2.45 (3H, s)

REFERENCE PRODUCTION EXAMPLE 4

500 mg of 4,4'-dihydroxydiphenyl ether was dissolved in 5 ml of N,N-dimethylformamide, 200 mg of sodium hydride (60% oil suspension) was added thereto under ice-cooling, the mixture was stirred at room temperature for ten minutes. Afterward, 410 mg of 5-chloro-3-ethyl-1-methyl-1H-pyrazole-4-carboaldehyde in 5 ml of N,N-dimethylformamide was added dropwise at 70° C. under stirring over ten minutes, stirred at 70° C. for two hours. The reaction mixture was cooled to room temperature, water and 10% hydrochloric acid were added thereto, and extracted with ethyl acetate. The organic layer was washed with water and saturated brine, dried over magnesium sulfate, and concentrated under reduced pressure. The residue was subjected to silica gel column chromatography to obtain 460 mg of the compound of formula (ii).

$^1$H-NMR (CDCl$_3$, TMS) δ (ppm): 9.51 (1H, s), 6.79-6.94 (8H, m), 5.44 (1H, s), 3.66 (3H, s), 2.86 (2H, q), 1.27 (3H, t)

REFERENCE PRODUCTION EXAMPLE 5

570 mg of 4,4'-dihydroxydiphenyl ether was dissolved in 5 ml of N,N-dimethylformamide, 170 mg of sodium hydride (60% oil suspension) was added thereto under ice-cooling, the mixture was stirred at room temperature for ten minutes. Afterward, 570 mg of 5-chloro-1-methyl-3-trifluoromethyl-1H-pyrazole-4-carboaldehyde in 5 ml of N,N-dimethylformamide was added dropwise at 70° C. under stirring over ten minutes, stirred at 70° C. for two hours. The reaction mixture was cooled to room temperature, water and 10% hydrochloric acid were added thereto, and extracted with ethyl acetate. The organic layer was washed with water and saturated brine, dried over magnesium sulfate, and concentrated under reduced pressure. The residue was subjected to silica gel column chromatography to obtain 440 mg of the compound of formula (vii).

$^1$H-NMR (CDCl$_3$, TMS) δ (ppm): 9.66 (1H, s), 6.79-6.93 (8H, m), 4.95 (1H, s), 3.81 (3H, s)

REFERENCE PRODUCTION EXAMPLE 6

560 mg of 4,4'-dihydroxydiphenyl ether was dissolved in 10 ml of N,N-dimethylformamide, 140 mg of sodium hydride (60% oil suspension) was added thereto under ice-cooling, the mixture was stirred at 70° C. for one hour. Afterward, 400 mg of 1-(5-chloro-1,3-dimethyl-1H-pyrazo-4-yl)ethanone in 5 ml of N,N-dimethylformamide was added dropwise at 70° C. under stirring over fifteen minutes, stirred at 70° C. for six hours. The reaction mixture was cooled to room temperature, diluted hydrochloric acid was added thereto, and extracted with ethyl acetate. The organic layer was washed with water and saturated brine, dried over magnesium sulfate, and concentrated under reduced pressure. The residue was subjected to silica gel column chromatography to obtain 340 mg of the compound of formula (vi).

$^1$H-NMR (CDCl$_3$, TMS) δ (ppm): 2.26 (3H, s), 2.47 (3H, s), 3.57 (3H, s), 5.22 (1H, s), 6.79-6.95 (8H, m)

The following describes formulation examples wherein parts represent parts by weight.

FORMULATION EXAMPLE 1

10 parts of each of the present compounds (1) to (40) is dissolved in the mixture of 35 parts of xylene and 35 parts of N,N-dimethylformamide, and 14 parts of polyoxyethylene styryl phenyl ether and 6 parts of calcium dodecylbenzenesulfonate are added thereto, followed by well stirring and mixing, to give 10% emulsion for each compound.

FORMULATION EXAMPLE 2

20 parts of each of the present compounds (1) to (40) is added to a mixture containing 4 parts of sodium laurylsulfate, 2 parts of calcium lignin sulfonate, 20 parts of synthetic hydrated silicone oxide fine powder, and 54 parts of diatomaceous earth, followed by well stirring and mixing, to give 20% wettable powder for each compound.

FORMULATION EXAMPLE 3

To 2 parts of each of the present compounds (1) to (40) are added 1 part of synthetic hydrated silicon oxide fine powder, 2 parts of calcium lignin sulfonate, 30 parts of bentonite, and 65 parts of kaolin clay, followed by well stirring and mixing, and an appropriate amount of water is added to this mixture, followed by further stirring, granulation with a granulator, and air drying, to give 2% granule for each compound.

FORMULATION EXAMPLE 4

1 part of each of the present compounds (1) to (40) is dissolved in an appropriate amount of acetone, and 5 parts of synthetic hydrated silicon oxide fine powder, 0.3 part of PAP, and 93.7 parts of Fubasami clay are well stirring and mixing, and acetone is removed by evaporation from the mixture, to give 1% powder for each compound.

FORMULATION EXAMPLE 5

10 parts of each of the present compounds (1) to (40), 35 parts of white carbon containing 50 parts of polyoxyethylene alkyl ether sulfate ammonium salt, and 55 parts of water are mixed and pulverized by the wet grinding method to give 10% flowable formulation for each compound.

FORMULATION EXAMPLE 6

0.1 part of each of the present compounds (1) to (40) is dissolved in a mixture of 5 parts of xylene and 5 parts of trichloroethane, and the resulting solution is mixed with 89.9 parts of deodorized kerosine to give 0.1% oil solution for each compound.

FORMULATION EXAMPLE 7

10 mg of each of the present compounds (1) to (40) is dissolved in 0.5 ml of acetone, the solution is applied to 5 g of powdery solid animal food (powdery solid animal food for bleeding CE-2; a product of CLEA Japan, Inc.) and mixed uniformly, and acetone is removed by evaporation from the mixture, to give poison bait for each compound.

The following test example will demonstrate the noxious arthropods controlling activity of the compound of the present invention.

TEST EXAMPLE 1

Each of the present compounds (2) to (15), (17) to (33), (36) to (40) and the comparative compound described below was formulated according to Formulation Example 5, and each formulations was diluted with water so that the concentration of the present compound or the comparative compound came to 500 ppm.

About twenty female adults of *Tetranychus urticae* were set free on brush bean (*Phaseolus vulgaris*) in the primary leaf stage, which had been potted in a plastic cup for 7 days after the seeding. After 1 day, a 30 ml of the diluted formulation described-above was sprayed over the plant. On the 8th and 13th day after the application, the numbers of lived *Tetranychus urticae* on the leaf of brush bean plant were examined, and the Controlling Rates were calculated by the following scheme.

Controlling Rate=100×{1−(a number of lived *Tetranychus urticae* in the treatment)/(a number of lived *Tetranychus urticae* in the non-treatment)}

As the result, in the treatment of the present compound (2) to (15), (17) to (33), and (36) to (40), all of the Controlling rates were not less than 90% on 8th day and 13th day after the application. In the treatment of the comparative compound, the Controlling rate was less than 30% on 8th day and 13th day after the application.

Comparative Compound

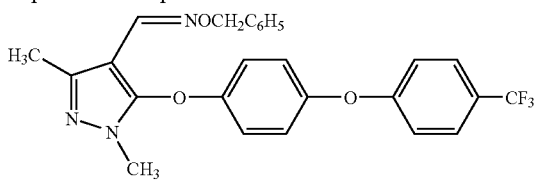

which is disclosed as the Compound No. 189 in the Japan unexamined Patent Publication S63-183564, p. 21.

TEST EXAMPLE 2

Each of the present compounds (3), (4), (6) to (10), (12) to (33), (36), (37), (39) and (40) was formulated according to Formulation Example 5, and each formulation was diluted with water so that the concentration of the present compound came to 500 ppm.

On the bottom of a polyethylene cup having a diameter of 5.5 cm, 9 g of a artificial bait (Silkmate 2S; produced by Nosan Corporation) was laid, and 1 ml of the diluted formulation described-above was added dropwise on the artificial bait. Thirty first-instar larvae of *Adoxophyes orana* were set free in the polyethylene cup. After 7 days, the numbers of the surviving *Adoxophyes orana* were examined to obtain the rate of dead pests.

As the result, in the treatment of the present compound (3), (4), (6) to (10), (12) to (33), (36), (37), (39) and (40), all of the rate of dead pests were not less than 90%.

INDUSTRIAL APPLICABILITY

By using the compound of the present invention, noxious arthropods can be controlled.

The invention claimed is:

1. A pyrazole compound of formula (a):

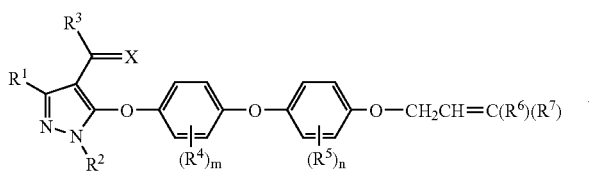

(a)

wherein $R^1$ represents C1-C4 alkyl or trifluoromethyl, $R^2$ represents C1-C4 alkyl, $R^3$ represents hydrogen or C1-C6 alkyl; $R^4$ represents halogen, C1-C3 alkyl, C1-C3 alkoxy, C1-C3 haloalkyl or C1-C3 haloalkoxy, m represents 0 to 4 integer, each of $R^4$s is same or different when m is 2 to 4 integer; $R^5$ represents halogen, C1-C3 alkyl, C1-C3 alkoxy, C1-C3 haloalkyl or C1-C3 haloalkoxy, n represents 0 to 4 integer, each of $R^5$s is same or different when n is 2 to 4 integer; $R^6$ and $R^7$ are same or different and represents hydrogen, halogen or methyl, X represents oxygen or $R^8O$—N; $R^8$ represents hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyanoalkyl or benzyl (wherein the benzyl may be substituted with halogen, C1-C4 alkyl, C1-C4 alkoxy, C2-C5 alkoxycarbonyl, trifluoromethyl or trifluoro methoxy).

2. The pyrazole compound according to claim 1, wherein $R^3$ is hydrogen in the formula (a).

3. The pyrazole compound according to claim 1, wherein $R^3$ is C1-C6 alkyl in the formula (a).

4. The pyrazole compound according to any one of claims 1 to 3, wherein X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyanoalkyl or benzyl (wherein the benzyl may be substituted with halogen, C1-C4 alkyl, C1-C4 alkoxy, C2-C5 alkoxycarbonyl, trifluoromethyl or trifluoro methoxy) in the formula (a).

5. The pyrazole compound according to any one of claims 1 to 3, wherein X is $R^8O$—N, and $R^8$ is hydrogen, C1-C6 alkyl, C1-C6 haloalkyl, C3-C6 alkenyl, C3-C6 haloalkenyl, C3-C6 alkynyl, C3-C6 haloalkynyl or C2-C5 cyanoalkyl in the formula (a).

6. The pyrazole compound according to any one of claims 1 to 3, wherein X is $R^8O$—N, and $R^8$ is a benzyl (wherein the benzyl may be substituted with halogen, C1-C4 alkyl, C1-C4 alkoxy, C2-C5 alkoxycarbonyl, trifluoromethyl or trifluoro methoxy) in the formula (a).

7. The pyrazole compound according to any one of claims 1 to 3, wherein X is oxygen in the formula (a).

8. The pyrazole compound according to claim 1, wherein $R^6$ is halogen in the formula (a).

9. The pyrazole compound according to claim 1, wherein $R^6$ and $R^7$ are halogen in the formula (a).

10. The pyrazole compound according to claim 1, wherein $R^6$ and $R^7$ are chlorine in the formula (a).

11. The pyrazole compound according to claim 1, wherein $R^4$ and $R^5$ are halogen, C1-C3 alkyl, C1-C3 alkoxy or trifluoromethyl, and m and n is 0 to 2 integer in the formula (a).

12. A noxious arthropods controlling composition comprising an effective amount of the pyrazole compound according to claim 1.

13. A method for controlling noxious arthropods comprising applying an effective amount of the pyrazole compound according to claim 1 to noxious arthropods or habitat of noxious arthropods.

14. A compound of formula (b):

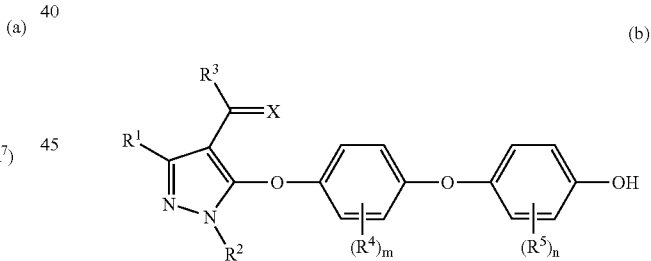

(b)

wherein $R^1$ represents C1-C4 alkyl or trifluoromethyl, $R^2$ represents C1-C4 alkyl, $R^3$ represents hydrogen or C1-C6 alkyl; $R^4$ represents halogen, C1-C3 alkyl, C1-C3 alkoxy, C1-C3 haloalkyl or C1-C3 haloalkoxy, m represents 0 to 4 integer, each of $R^4$s is same or different when m is 2 to 4 integer; $R^5$ represents halogen, C1-C3 alkyl, C1-C3 alkoxy, C1-C3 haloalkyl or C1-C3 haloalkoxy, n represents 0 to 4 integer, each of $R^5$s is same or different when n is 2 to 4 integer; X represents oxygen or $R^8O$—N; $R^8$ represents hydrogen, C1-C6 alkyl, C1-C6 haloalkyl, C3-C6 alkenyl, C3-C6 haloalkenyl, C3-C6 alkynyl, C3-C6 haloalkynyl, C2-C5 cyano alkyl or benzyl (wherein the benzyl may be substituted with halogen, C1-C4 alkyl, C1-C4 alkoxy, C2-C5 alkoxycarbonyl, trifluoromethyl or trifluoro methoxy).

* * * * *